US011260050B2

(12) United States Patent
Moran

(10) Patent No.: US 11,260,050 B2
(45) Date of Patent: Mar. 1, 2022

(54) COMBINATION OF COTININE PLUS ANTIOXIDANT FOR TREATMENT-RESISTANT DEPRESSION AND CORRECTION OF ASTROCYTES FUNCTIONAL DEFICIT INDUCED BY DEPRESSION AND OTHER NEUROPATHOLOGICAL

(71) Applicant: UNIVERSIDAD SAN SEBASTIAN, Concepcion (CL)

(72) Inventor: Valentina Echeverria Moran, Largo, FL (US)

(73) Assignees: UNITED STATES GOVERNMENT AS REPRESENTED BY THE DEPARTMENT OF VETERANS AFFAIRS, Washington, DC (US); UNIVERSIDAD SAN SEBASTIAN, Concepcion (CL)

( * ) Notice: Subject to any disclaimer, the term of this patent is extended or adjusted under 35 U.S.C. 154(b) by 0 days.

(21) Appl. No.: 16/486,498

(22) PCT Filed: Feb. 16, 2018

(86) PCT No.: PCT/IB2018/000306
§ 371 (c)(1),
(2) Date: Aug. 15, 2019

(87) PCT Pub. No.: WO2018/150276
PCT Pub. Date: Aug. 23, 2018

(65) Prior Publication Data
US 2020/0000790 A1 Jan. 2, 2020

Related U.S. Application Data
(60) Provisional application No. 62/459,736, filed on Feb. 16, 2017.

(51) Int. Cl.
| | | |
|---|---|---|
| *A61K 31/4439* | (2006.01) | |
| *A61P 39/06* | (2006.01) | |
| *A61P 25/28* | (2006.01) | |
| *A61P 25/22* | (2006.01) | |
| *A61P 25/24* | (2006.01) | |
| *A61K 9/00* | (2006.01) | |
| *A61K 9/127* | (2006.01) | |
| *A61K 31/202* | (2006.01) | |
| *A61K 35/612* | (2015.01) | |

(52) U.S. Cl.
CPC ........ *A61K 31/4439* (2013.01); *A61K 9/0043* (2013.01); *A61K 9/0053* (2013.01); *A61K 9/127* (2013.01); *A61K 31/202* (2013.01); *A61K 35/612* (2013.01); *A61P 25/22* (2018.01); *A61P 25/24* (2018.01); *A61P 25/28* (2018.01); *A61P 39/06* (2018.01)

(58) Field of Classification Search
CPC .............. A61K 31/4439; A61K 9/0043; A61K 9/0053; A61K 9/127; A61K 31/202; A61K 35/612; A61P 39/06; A61P 25/28; A61P 25/22; A61P 25/24
See application file for complete search history.

(56) References Cited

U.S. PATENT DOCUMENTS

| | | |
|---|---|---|
| 3,870,794 A | 3/1975 | Hutchinson et al. |
| 4,938,949 A | 7/1990 | Borch et al. |
| 5,187,169 A | 2/1993 | Lippiello et al. |
| 5,612,357 A | 3/1997 | Keenan et al. |
| 5,776,956 A | 7/1998 | Rolf |
| 5,889,029 A | 3/1999 | Rolf |
| 6,218,383 B1 | 4/2001 | Bencherif |
| 8,273,731 B2 | 9/2012 | Heldman |
| 9,801,865 B2 | 10/2017 | Moran |
| 10,238,641 B2 | 3/2019 | Echeverria Moran |
| 10,307,411 B2 | 6/2019 | Echeverria Moran |

(Continued)

FOREIGN PATENT DOCUMENTS

| | | |
|---|---|---|
| EP | 1337855 B1 | 8/2003 |
| WO | WO 2008/103818 A1 | 8/2008 |

(Continued)

OTHER PUBLICATIONS

Burgess and Echeverria (2010) "Raf Inhibitors as Therapeutic Agents Against Neurodegenerative Diseases," *CNS & Neurological Disorders—Drug Targets* 9: 120-127.
Colquhoun, et al. (1997) "Pharmacology of neuronal nicotinic acetylcholine receptor subtypes." *Adv Pharmacol* 39: 191-220.
Fabel, et al. (2003) "VEGF is necessary for exercsie-induced adult hippocampal neurogenesis." *Eur J Neurosci* 18: 2803-2812.
Felmingham, et al. (2009) "Duration of posttraumatic stress disorder predicts hippocampal grey matter loss." *Neuroreport* 20: 1402-1406.

(Continued)

*Primary Examiner* — Snigdha Maewall
(74) *Attorney, Agent, or Firm* — Ballard Spahr LLP

(57) ABSTRACT

The present invention relates to a method of a) treating any of depression induced by chronic stress; depression in a subject afflicted with PTSD; anxiety induced by chronic stress; anxiety in a subject afflicted with PTSD; cognitive impairment induced by chronic stress; altered morphology and/or reduced number of GFAP+ cells in hippocampus and/or frontal cortex induced by chronic stress; working memory impairment in a subject afflicted with PTSD; b) inhibiting or reversing loss of GFAP+ cells in hippocampus and/or frontal cortex induced by chronic stress; c) decreasing consolidation of contextual fear memory in a subject afflicted with PTSD; d) enhancing extinction of fear memory in a subject afflicted with PTSD; or e) increasing calcineurin A expression in a subject afflicted with PTSD using a combination of cotinine and an antioxidant.

20 Claims, 29 Drawing Sheets

(56) References Cited

U.S. PATENT DOCUMENTS

| | | | |
|---|---|---|---|
| 2003/0166554 | A1 | 9/2003 | Cohen et al. |
| 2004/0223909 | A1 | 11/2004 | Montalto et al. |
| 2004/0242698 | A1 | 12/2004 | Hughes |
| 2007/0066665 | A1 | 3/2007 | Yang et al. |
| 2008/0108574 | A1* | 5/2008 | Barlow .................. A61K 45/06 514/10.7 |
| 2010/0104504 | A1* | 4/2010 | Echeverria Moran ....................... A61K 51/0455 424/1.11 |
| 2010/0234349 | A1 | 9/2010 | Olsen et al. |
| 2010/0247653 | A1 | 9/2010 | Laulenschlager |
| 2014/0274968 | A1* | 9/2014 | Berge ...................... A23L 33/00 514/120 |
| 2015/0164841 | A1* | 6/2015 | Hoem ........................ C11B 3/12 514/560 |
| 2018/0092896 | A1 | 4/2018 | Echeverria Moran |
| 2019/0167653 | A1 | 6/2019 | Echeverria Moran |

FOREIGN PATENT DOCUMENTS

| | | |
|---|---|---|
| WO | WO 2016/070181 A1 | 5/2016 |
| WO | WO 2018/150276 | 8/2018 |

OTHER PUBLICATIONS

Femenia T, et al. (2012) "Dysfunctional hippocampal activity affects emotion and cognition in mood disorders" *Brain Res* 1476:58-70.

Feng, et al. (2015) "FGF2 alleviates PTSD symptoms in rats by restoring GLAST function in astrocytes via the JAK/STAT pathway." *Eur Neuropsychopharmacol.* 25: 1287-1299.

Fernandes BS, et al. (2011) "Brain-derived neurotrophiC factor as a state-marker of mood episodes in bipolar disorders: a systematic review and meta-regression analysis" *J Psychiatr Res* 45(8):995-1004.

Ferraz, et al. (2011) "Chronic omega-3 fatty acids supplementation promotes beneficial effects on anxiety, cognitive and depressive-like behaviors in rats subjected to a restraint stress protocol." *Behav Brain Res* 219: 116-122.

Filipovic, et al. (2011) "Volume changes of corpus striatum, thalamus, hippocampus and lateral ventricles in posttraumatic stress disorder (PTSD) patients suffering from headaches and without therapy." *Cent Eur Neurosurg* 72: 133-137.

Filippis (2011) "Neural stem cell-mediated therapy for rare brain diseases: perspectives in the near future for LSDs and MNDs." *Histol Histopathol* 26: 1093-1109.

Forster, et al. (2016) "Nucleotides protect rat brain astrocytes against hydrogen peroxide toxicity and induce antioxidant defense via P2Y receptors." *Neurochem Int* 94: 57-66.

Foster TC, et al. (2001) "Calcineurin links Ca2+ 20 dysregulation with brain aging" *J Neurosci* 21 (11):4066-4073.

Franklin, et al. (2001) "The Mouse Brain in Stereotaxic Coordinates," Academic Press, San Diego, CA.

Fournier, et al. (2012) "Role of vascular endothelial growth factor in adult hippocampal neurogenesis: implications for the pathophysiology and treatment of depression." *Behav Brain Res* 227: 440-449.

Froeliger, B. et al. (2009) "Effects of nicotine on novelty detection and memory recognition performance: double-blind, placebo-controlled studies of smokers and nonsmokers." *Psychopharmacology.* 205:625-33.

Fuchs, et al. (2006) "Remodeling of neuronal networks by stress." *Front Biosci* 11: 2746-2758.

Fuller, et al. (2010) "Activated astroglia during chronic inflammation in Alzheimer's disease—do they neglecte their neurosupportive roles?" *Mutat Res* 690: 40-49.

Fuxe, et al. (1979) "On the action of nicotine and cotinine on central 5-hydroxytryptamine neurons." *Pharmacol Biochem Behav.* 10: 671-677.

Gahring, L.C. et al. (2003) "Nicotine-induced neuroprotection against N-methyl-aspartic-acid or betaamyloid peptide occur through independent mechanisms distinguished by pro-inflammatory cytokines." *J Neurochem.* 87:1125-36.

Gallinat, J. et al. (2006) "Smoking and structural brain deficits: a volumetric MR investigation." *Eur J Neurosci.* 24:1744-50.

Gao, et al. (2014) "Evaluation of nicotine and cotinine analogs as potential neuroprotective agents for Alzheimer's disease." *Bioorg Med Chem Lett* 24: 1472-1478.

Garfinkel SN, et al. (2014) "Impaired contextual modulation of memories in PTSD: an fMRI and psychophysiological study of extinction retention and fear renewal" *J Neurosci* 34(40):13435-13443.

Garzon, et al. (2016) "Novel Approaches in Astrocyte Protection: from Experimental Methods to Computational Approaches." *J Mol Neurosci* 58: 483-492.

Ghashghaei, et al. (2007) "Reinduction of ErbB2 in astrocytes promotes radial glial progenitor identity in adult cerebral cortex." *Genes Dev* 21: 3258-3271.

Gibbs, et al. (2006) "Inhibition of glycogenolysis in astrocytes interrupts memory consolidation in young chickens." *Glia* 54: 214-222.

Gonul, et al. (2011) "Association of the brain-derived neurotrophic factor Val66Met polymorphism with hippocampus volumes in drug-free depressed patients." *World J Biol Psychiatry* 12:110-118.

Gonzalez-Giraldo, et al. (2017) "Tibolone Preserves Mitochondrial Functionality and Cell Morphology in Astrocytic Cells Treated with Palmitic Acid." *Mol Neurobiol,* DOI 10.1007/s12035-017-0667-3.

Graef IA, et al. (2003) "Neurotrophins and netrins require calcineurin/NFAT signaling to stimulate outgrowth of embryonic axons" *Cell* 113 (5):657-670.

Grayson, et al. (2015) "Assessment of disease-related cognitive impairments using the novel object recognition (NOR) task in rodents." *Behav Brain Res* 285: 176-193.

Grizzell JA, et al. (2014) "Cotinine reduces depressive-like behavior, working memory deficits, and synaptic loss associated with chronic stress in mice" *Behav Brain Res* 268:55-65.

Grizzell JA, et al. (2017) "Cotinine improves visual recognition memory and decreases cortical Tau phosphorylation in the Tg6799 mice" *Prog Neuropsychopharmacol Biol Psychiatry* 78:75-81.

Grizzell, et al. (2014) "Cotinine reduces depressive-like behavior and hippocampal vascular endothelial growth factor downregulation after forced swim stress in mice." *Behav Neurosci* 128: 713-721.

Grizzell, et al. (2014) "New insights into the mechanisms of action of cotinine and its distinctive effects from nicotine." *Neurochem Res* 40: 2032-2046.

Grizzell, V., et al., (2015) "New Insights into the Mechanisms of Action of Cotinine and 10 its Distinctive Effects from Nicotine," *Neurochem Res,* 40: 2032-2046.

Groth RD, et al. (2003) "Brain-derived neurotrophic factor activation of NFAT 10 (nuclear factor of activated T-cells)-dependent transcription: a role for the transcription factor NFATc4 in neurotrophin-mediated gene expression" *J Neurosci* 23(22):8125-8134.

Gu Z, et al. (2012) "Cholinergic coordination of presynaptic and postsynaptic activity induces timing-dependent hippocampal synaptic plasticity" *J Neurosci* 32 (36):12337-12348.

Gundersen BB,et al. (2013) "Increased Hippocampal Neurogenesis and Accelerated Response to Antidepressants in Mice with Specific Deletion of CREB in the Hippocampus: Role of cAMP Response-Element Modulator tau" *J Neurosci* 33 (34):13673-13685.

Guo-Ross, et al. (1999) "Decrease of glial fibrillary acidic protein in rat frontal cortex following aluminum treatment." *J Neurochem* 73: 1609-1614.

Hall J, et al. (2001) "Fear memory retrieval induces CREB phosphorylation and Fos expression within the amygdala" *Eur J Neurosci* 13(7): 1453-1458.

Halldin, C. et al. (1992) "(S)- and (R)-[11C]Nicotine and the Metabolite (R/S)-[11C]Cotinine. Preparation, Metabolite Studies and In Vivo Distribution in the Human Brain Using PET." *Nucl Med Biol.* 19(8):871-80.

(56) References Cited

OTHER PUBLICATIONS

Hammond, D.K. et al. (1991) "Metabolism of nicotine by rat liver cytochromes P-450. Assessment utilizing monoclonal antibodies to nicotine and cotinine." *Drug Metab Dispos.* 19(4):804-8.
Hamada, M. et al. (2005) "Nicotine Regulates DARPP-32 (Dopamine- and cAMP-Regulated Phosphoprotein of 32 kDa) Phosphorylation at Multiple Sites in Neostriatal Neurons." *J Pharm Exp Therap.* 315(2):872-8.
Hanson and Frey, 2nd, (2007) "Strategies for intranasal delivery of therapeutics for the prevention and treatment of neuroAIDS." *J Neuroimmune Pharmacol* 2: 81-86.
Hanson LR, et al. (2012) "Intranasal delivery of growth differentiation factor to the central nervous system" *Drug Deliv* 19(3): 149-154.
Hanson, L.R., Frey, W.H., 2nd, (2008) "Intranasal delivery bypasses the blood-brain barrier to target therapeutic agents to the central nervous system and treat neurodegenerative disease." *BMC Neurosci* 9 Suppl 3: S5.
Hatsukami D, et al. (1992) "Smokeless tobacco abstinence effects and nicotine gum dose" *Psychopharmacology* 106(1 ):60-66.
Hatsukami D, et al. (1998) "Cotinine: effects with and without nicotine" *Psychopharmacology* 135(2): 141-150.
Hatsukami D, et al. (1998) "Effects of cotinine on cigarette self-administration" *Psychopharmacology* 138(2):184-189.
Hatsukami DK, et al. (1997) "Safety of cotinine in humans: physiologic, subjective, and cognitive effects" *Pharmacol Biochem Behav* 57(4):643-650.
Hawkins, K.A. and Cougle, J.R. (2013) "The effects of nicotine on intrusive memories in nonsmokers." *Exp Clin Psychopharmacol.* 21(6):434-42.
Hayase (2011) "Depression-related anhedonic behaviors caused by immobilization stress: a comparison with nicotine-induced depression-like behavioral alterations and effects of nicotine and/or 'antidepressant' drugs." *J Toxicol Sci* 36: 31-41.
Haydon and Nedergaard (2014) "How do astrocytes participate in neural plasticity?" *Cold Spring Harb Perspect Biol* 7: a020438.
Head, et al. (2004) "Down syndrome and beta-amyloid deposition" *Curr. Opin. Neurol.* 17: 95-100.
Heinrichs, et al. (2013) "Repeated valproate treatment facilitates fear extinction under specific stimulus conditions." *Neurosci Lett* 552: 108-113.
Hellstrom-Lindahl, E. et al. (2004) "Nicotine reduces A beta in the brain and cerebral vessels of APPsw mice." *Eur J Neurosci.* 19:2703-10.
Hennessy, et al. (2015) "Astrocytes Are Primed by Chronic Neurodegeneration to Produce Exaggerated Chemokine and Cell Infiltration Responses to Acute Stimulation with the Cytokines IL-lbeta and TNF-alpha." *J Neurosci* 35: 8411-8422.
Hensley K, et al. (2006) "On the relation of oxidative stress to neuroinflammation: lessons learned from the G93A-SOD1 mouse model of amyotrophic lateral sclerosis" *Antioxid Redox Signal* 8 (11-12):2075-2087.
Hess, B. et al. (1997) "LINGS: A linear constraint solver for molecular simulations." *J Comput Chem.* 18:1463-72.
Hien DA, et al. (2015) "Combining seeking safety with sertraline for PTSD and alcohol use disorders: A randomized controlled trial" *J Consult Clin Psychol* 83 (2):359-369.
Hoge, C.W. et al. (2004) "Combat duty in Iraq and Afghanistan, mental health problems, and barriers to care." *N Engl J Med.* 351:13-22.
Hogg, S. (1996) "A review of the validity and variability of the elevated plus-maze as an animal model of anxiety." *Pharmacol Biochem Behav* 54: 21-30.
Hong, D.P. et al. (2009) "Smoking and Parkinson's disease: does nicotine affect alpha-synuclein fibrillation?" *Biochim Biophys Acta.* 1794:282-90.
Honsek, et al. (2012) "Astrocyte calcium signals at Schaffer collateral to CA1 pyramidal cell synapses correlate with the No. of activated synapses but not with synaptic strength." *Hippocampus* 22: 29-42.

"How is Chemotherapy Given?" Chemocare.com, Feb. 1, 2013.
Hovatta I, et al. (2010) "Oxidative stress in anxiety and comorbid disorders" *Neurosci Res* 68 (4):261-275.
Hsiao, K. et al. (1996) "Correlative memory deficits, Abeta elevation, and amyloid plaques in transgenic mice." *Science.* 274:99-102.
Iarkov, et al. (2016) "Post-treatment with cotinine improved memory and decreased depressive-like behavior after chemotherapy in rats." *Cancer Chemother Pharmacol* 78: 1033-1039.
Imbe, et al. (2012) "Chronic restraint stress decreases glial fibrillary acidic protein and glutamate transporter in the periaqueductal gray matter." *Neuroscience* 223: 209-218.
Jaggi, et al. (2011) "A review on animal models for screening potential anti-stress agents." *Neurol Sci* 32: 993-1005.
Jak, et al. (2016) "Neurocognition in PTSD: Treatment Insights and Implications." *Curr Top Behav Neurosci.*
Javidi, H., Yadollahie, M. (2012) "Post-traumatic Stress Disorder." *Int J Occup Environ Med* 3: 2-9.
Joels, H., et al. (2004) "Effects of chronic stress on structure and cell function in rat hippocampus and hypothalamus" *Stress*, 7: 221-231.
Jones et al. (1992) "Effects of acute subcutaneous nicotine on attention, information processing and short term memory in Alzheimer's disease" *Psychopharmacology* 108(4): 485-494.
Jun H, et al. (2012) "Functional role of adult hippocampal neurogenesis as a therapeutic strategy for mental disorders" *Neural Plast* 2012: 854285.
Kabadi, et al. (2014) "CR8, a novel inhibitor of CDK, limits microglial activation, astrocytosis, neuronal loss, and neurologic dysfunction after experimental traumatic brain injury." *J Cereb Blood Flow Metab* 34: 502-513.
Kalaitzakis, M.E. et al. (2008) "Striatal β-Amyloid Deposition in Parkinson Disease with Dementia." *J Neuropathol Exp Neurol.* 67(2): 155-61.
Kamo T, et al. (2016) "Dosage, effectiveness, and safety of sertraline treatment for posttraumatic stress disorder in a Japanese clinical setting: a retrospective study" *BMC Psychiatry* 16(1):434.
Karperien and Jelinek (2015) "Fractal, multifractal, and lacunarity analysis of microglia in tissue engineering." *Front Bioeng Biotechnol* 3: 51.
Karperien, et al. (2013) "Quantitating the subtleties of microglial morphology with fractal analysis." *Front Cell Neurosci* 7: 3.
Kassem, et al. (2013) "Stress-induced grey matter loss determined by MRI is primarily due to loss of dendrites and their synapses." *Mol Neurobiol* 47: 645-661.
Kessler, R.C. (2000) "Posttraumatic stress disorder: the burden to the individual and to society." *J Clin Psychiatry.* 61 (Suppl 5):4-12.
Kessler, R.C. et al. (2005) "Prevalence, severity, and comorbidity of 12-month DSM-IV disorders in the National Comorbidity Survey Replication." *Arch Gen Psychiatry.* 62:617-27.
Kidd PM (2007) "Omega-3 DHA and EPA for cognition, behavior, and mood: clinical findings and structural-functional synergies with cell membrane phospholipids" *Altern Med Rev* 12(3):207-227.
Kim MS, et al. (2014) "Nerve growth factor (NGF) regulates activity of nuclear factor of activated T-cells (NFAT) in neurons via the phosphatidylinositol 3-kinase (PI3K)-Akt-glycogen synthase kinase 313 (GSK3f3) pathway" *J Biol Chem* 289(45):31349-31360.
Kim, et al. (2015) "The RAGE receptor and its ligands are highly expressed in astrocytes in a grade-dependant manner in the striatum and subependymal layer in Huntington's disease." *J Neurochem* 134: 927-942.
Kingsbury TJ, et al. (2007) "Calcineurin activity is required for depolarization-induced, CREB-dependent gene transcription in cortical neurons" *J Neurochem* 103 (2):761-770.
Kirschner, D.A. et al. (2008) "Fiber diffraction as a screen for amyloid inhibitors." *Curr Alzheimer Res.* 5:288-307.
Kirtley A, et al. (2010) "The exclusive induction of extinction is gated by BDNF" *Learn Mem* 17(12):612-619.
Kleen, et al. (2006) "Chronic stress impairs spatial memory and motivation for reward without disrupting motor ability and motivation to explore." *Behav Neurosci* 120: 842-851.
Knox, D et al. (2012) "Single prolonged stress disrupts retention of extinguished fear in rats." *Learn Mem.* 19(2):43-9.

(56) References Cited

OTHER PUBLICATIONS

Koch SB, et al. (2016) "Intranasal Oxytocin Administration Dampens Amygdala Reactivity towards Emotional Faces in Male and Female PTSD Patients" *Neuropsychopharmacology* 41 (6): 1495-1504.
Koek RJ, et al. (2016) "Treatment-refractory posttraumatic stress disorder (TRPTSD): a review and framework for the future" *Prog Neuropsychopharmacol Biol Psychiatry* 70:170-218.
Koenen KC, et al. (2017) "Post-traumatic stress disorder and cardiometabolic disease: improving causal inference to inform practice." Psychol Med 47(2):209-225.
Koppelmans, et al. (2012) "Global and focal white matter integrity in breast cancer survivors 20 years after adjuvant chemotherapy." *Hum Brain Mapp* 35: 889-899.
Koppelmans, et al. (2013) "Late effects of adjuvant chemotherapy for adult onset non-CNS cancer; cognitive impairment, brain structure and risk of dementia." *Crit Rev Oncol Hematol* 88: 87-101.
Kretzschmar, et al. (1985) "Measurement of GFAP in hepatic encephalopathy by ELISA and transblots." *J Neuropathol Exp Neurol* 44: 459-471.
Kudo, Y. et al. (2007) "2-(242-Dimethylaminothiazol-5-yflethenyl)-6-(2-[fluoro]ethoxy)benzoxazole: a novel PET agent for in vivo detection of dense amyloid plaques in Alzheimer's disease patients." *J Nucl Med.* 48:553-61.
Kutlu, M.G. and Gould, T.J. (2014) "Acute nicotine delays extinction of contextual fear in mice." *Behav Brain Res.* 263:133-7.
Kutlu, M.G. et al. (2014) "The effects of acute nicotine on contextual safety discrimination" *J Psychopharmacol.* 28(11):1064-70.
Kutlu, et al. (2016) "Impairment of contextual fear extinction by chronic nicotine and withdrawal from chroic nicotine is associated with hipocampal nAChR upregulation" Neuropharmacology 109: 341-8.
Kwantes JM, et al. (2015) "A brief review of krill oil history, research, and the commercial market" *J Diet Suppl* 12(1):23-35.
Lapiz-Bluhm, M.D. and Peterson, A.L. (2014) "Neurobehavioral mechanisms of traumatic stress in posttraumatic stress disorder." *Curr Top Behav Neurosci.* 18:161-90.
Laugharne, et al. (2016) "Amygdala Volumetric Change Following Psychotherapy for Posttraumatic Stress Disorder." *J Neuropsychiatry Clin Neurosci*, appineuropsych16010006.
Lee, et al. (2009) "Induction of Neuronal Vascual Endothelial Growth Factor Expression by cAMP in the Dentate Gyrus of the Hippocampus is Required for Antidepressant-Like Behaviors." *The Journal of Neuroscience* 29: 8493-8505.
Lee, et al. (2014) "Astrocytes contribute to gamma oscillations and recognition memory." *Proc Natl Acad Sci USA* 111: E3343-3352.
Lee, et al. (2017) "Cannabidiol regulation of emotion and emotional memory processing: relevance for treating anxiety-related and substance abuse disorders." *Br J Pharmacol.* 174(19): 3242-3256.
Lee, H., et al. (2013) "Glutamine deficiency in the prefrontal cortex increases depressive-like behaviours in male mice" *J Psychiatry Neurosci* 38: 183-191.
Lesage, et al. (2012) "The Reinforcement Threshold for Nicotine as a Target for Tobacco Control." *Drug Alcohol Depend* 125: 1-7.
Leventopoulos, D., et al. (2007) "Long-term effects of early life deprivation on brain glia in Fischer rats" *Brain Res*, 1142: 119-126.
Levin, E.D. (2002) "Nicotinic receptor subtypes and cognitive function." *J Neurobiol.* 53:633-40.
Li, et al. (2011) "Astrocytes: implications for neuroinflammatory pathogenesis of Alzheimer's disease." *Curr Alzheimer Res* 8: 67-80.
Liberzon I, et al. (2006) "Neuroimaging studies of emotional responses in PTSD" *Ann NY Acad Sci* 1071:87-109.
Lin CH, et al. (2003) "The similarities and diversities of signal pathways leading to consolidation of conditioning and consolidation of extinction of fear memory" *J Neurosci* 23(23):8310-8317.
Lin CH, et al. (2003) "Identification of calcineurin as a key signal in the extinction of fear memory" *J Neurosci* 23(5): 1574-1579.
Lin CH, et al. (2003) "Involvement of a calcineurin cascade in amygdala depotentiation and quenching of fear memory" Mol Pharmacol 63(1):44-52.

Liu, et al. (2015) "Activation of alpha7 nicotinic acetylcholine receptors protects astrocytes against oxidative stress-induced apoptosis: implications for Parkinson's disease." Neuropharmacology 91: 87-96.
Lindahl, E et al. (2001) "GROMACS 3.0: a package for molecular simulation and trajectory analysis." J Mol Model. 7:306-17.
Livak, et al. (2001) "Analysis of relative gene expression data using real-time quantitative PCR and the 2(-Delta Delta C(T)) Method." Methods 25: 402-8.
Lucassen, et al. (2006) "Stress, depression and hippocampal apoptosis." *CNS Neurol Disord Drug Targets* 5: 531-546.
Luine (2016) "Estradiol: Mediator of memories, spine density and cognitive resilience to stress in female rodents." *The Journal of steroid biochemistry and molecular biology* 160: 189-195.
Lunn, et al. (2009) "Vascular endothelial growth factor prevents G93A-SOD1-induced motor neuron degeneration." *Developmental neurobiology* 69: 871-884.
Lynns, et al. (2012) "Fluoxetine counteracts the cognitive and cellular effects of 5-fluorouracil in the rat hippocampus by a mechanism of prevention rather than recovery." *PLoS ONE* 7: e30010.
Magarinos, et al. (1997) "Chronic stress alters synaptic terminal structure in hippocampus." *Proc Natl Acad Sci U S A* 94: 14002-14008.
Magarinos, et al. (2011) "Effect of brain-derived neurotrophic factor haploinsufficiency on stress-induced remodeling of hippocampal neurons." *Hippocampus* 21: 253-264.
Mahan AL, Ressler KJ (2012) "Fear conditioning, synaptic plasticity and the amygdala: implications for posttraumatic stress disorder" *Trends Neurosci* 35(1):24-35.
Mansuy IM (2003) "Calcineurin in memory and bidirectional plasticity" *Biochem Biophys Res Commun* 311 (4):1195-1208.
Maren S, et al. (2013) "The contextual brain: implications for fear conditioning, extinction and psychopathology" *Nat Rev Neurosci* 14(6):417-428.
McEwen (1997) "Prevention of stress-induced morphological and cognitive consequences." *Eur Neuropsychopharmacol* 7 Suppl 3: S323-328.
McHugh, et al. (2012) "Anger in PTSD: is there a need for a concept of PTSD-related posttraumatic anger?" *Clin Psychol Rev* 12: 93-10d.
Mendoza C, et al. (2016) "Role of neuroinflammation and sex hormones in war-related PTSD" *Mol Cell Endocrinol* 434:266-277.
Meneses G, et al. (2017) "Intranasal delivery of dexamethasone efficiently controls LPS-induced murine neuroinflammation" *Clin Exp Immunol* 190(3):304-314.
Meng, et al. (2016) "Trauma-specific Grey Matter Alterations in PTSD." *Sci Rep* 6: 33748.
Merchant, C. et al. (1999) "The influence of smoking on the risk of Alzheimer's disease" *Neurology* 52:1408-12.
Mika, G.J., et al. (2012) "Chronic Stress Impairs Prefrontal Cortex-Dependent Response Inhibition and Spatial Working Memory," *Behav Neurosci* 126(5): 605-619.
Milad, M.R. et al. (2006) "Fear Extinction in Rats: Implications for Human Brain Imaging and Anxiety Disorders." *Biol Psychol.* 73:61-71.
Moller, et al. (2015) "Two Phase III randomised double-blind studies of fixed-dose TC-5214 (dexmecamylamine) adjunct to ongoing antidepressant therapy in patients with major depressive disorder and an inadequate response to prior antidepressant therapy." *World J Biol Psychiatry* 16: 483-501.
Moore, S.A. et al. (2004) "Both the 0-(+) and L-(−) enantiomers of nicotine inhibit Abeta aggregation and cytotoxicity" *Biochemistry* 43:819-26.
Moran VE (2012) "Cotinine: Beyond that Expected, More than a Biomarker of Tobacco Consumption" *Front Pharmacol* 3:173.
Moreira, et al. (2016) "Impact of Chronic Stress Protocols in Learning and Memory in Rodents: Systematic Review and Meta-Analysis." *PLoS One* 11: e0163245.
Morris, G.M. et al. (1998) "Automated Docking Using a Lamarckian Genetic Algorithm and Empirical Binding Free Energy Function." *J Comput Chem.* 19:1639-62.

(56) References Cited

OTHER PUBLICATIONS

Abidin, et al., (2004) "The effect of chronic restraint stress on spatial learning and memory: relation to oxidant stress," *Int J Neurosci*, 114: 683-699.
Admon, et al. (2013) "Stress-induced reduction in hippocampal volume and connectivity with the ventromedial prefrontal cortex are related to maladaptive responses to stressful military service." *Hum Brain Mapp* 34: 2808-2816.
Ahearn EP, et al. (2011) "A review of atypical antipsychotic medications for posttraumatic stress disorder" *Int Clin Psychopharmacol* 26(4): 193-200.
Ahi J, et al. (2004) "The role of hippocampal signaling cascades in consolidation of fear memory" *Behav Brain Res* 149(1): 17-31.
Ahmed-Leitao, et al. (2016) "Hippocampal and amygdala volumes in adults with posttraumatic stress disorder secondary to childhood abuse or maltreatment: A systematic review." *Psychiatry Res* 256: 33-43.
Alcala-Barraza SR, et al. (2010) "Intranasal delivery of neurotrophic factors BDNF, CNTF, EPO, and NT-4 to the CNS" *J Drug Target* 18(3): 179-190.
Antunes and Biala (2012) "The novel object recognition memory: neurobiology, test procedure, and its modifications." *Cogn Process* 13: 93-110.
Apfel, et al. (2011) "Hippocampal volume differences in Gulf War veterans with current versus lifetime posttraumatic stress disorder symptoms." *Biol Psychiatry* 69: 541-548.
Arnson Y, et al. (2007) Physical activity protects male patients with post-traumatic stress disorder from developing severe fibromyalgia *Clin Exp Rheumatol* 25(4):529-533.
Babb, et al. (1996) "Astrocytes may contribute to the latent period in progressive neuron loss, axon sprouting, and chronic seizuures in rat kainate hippocampal epilespy." *Epilepsy Res Suppl* 12: 343-354.
Balsera, et al. (2014) "Chaicones as positive allosteric modulators of alpha7 nicotinic acetylcholine receptors: a new target for a privileged structure." *Eur J Med Chem* 86: 724-739.
Bandyopadhyaya, G. et al. (2008) "Protective role of curcumin against nicotine-induced genotoxicity on rat liver under restricted dietary protein." *Eur J Pharmacol*. 588(2-3):151-7.
Barbieri, et al. (1986) "Nicotine, cotinine, and anabasine inhibit aromatase in human trophoblast in vitro." *J Clin Invest* 77: 1727-1733.
Barreto GE, et al. (2015) "Nicotine-Derived Compounds as Therapeutic Tools Against Post-Traumatic Stress Disorder" *Curr Pharm Des* 21(25):3589-3595.
Barros MP, et al. (2014) "Neuroprotective properties of the marine carotenoid astaxanthin and omega-3 fatty acids, and perspectives for the natural combination of both in krill oil" *Nutrients* 6(3):1293-1317.
Bauer, et al. (2001) "Restraint stress is associated with changesin glucocorticoid immunoregulation." *Physiol Behav* 73: 525-532.
Belzung, et al. (2001) "Measuring normal and pathological anxiety-like behaviour in mice: a review." *Behav Brain Res* 125: 141-149.
Benarroch, E.E. (2005) "Neuron-astrocyte interactions: partnership for normal function and disease in the central nervous system." *Mayo Clin Proc* 80: 1326-1338.
Bencherif, et al. (2014) "Alpha? neuronal nicotinic receptor: a pluripotent target for diseases of the central nervous system." *CNS Neurol Disord Drug Targets* 13: 836-845.
Benedict C, et al. (2011) "Intranasal insulin as a therapeutic option in the treatment of cognitive impairments" *Exp Gerontol* 46(2-3): 112-115.
Bennett and Lagopoulos (2014) "Stress and trauma: BDNF control of dendritic-spine formation and regression." *Prog Neurobiol* 112: 80-99.
Benowitz NL, et al. (1989) "Inverse relation between serum cotinine concentration and blood pressure in cigarette smokers" *Circulation* 80(5):1309-1312.
Berendsen, H.J.C. et al. (1995) "GROMACS: A message-passing parallel molecular dynamics implementation." *Comput Phys Commun*. 91:43-56.

Bernardinelli, et al. (2014) "Astrocyte-synapse structural plasticity." *Neural Plast* 2014: 232105.
Bewernick BH, et al. (2013) "Chronic depression as a model disease for cerebral aging" *Dialogues Clin Neurosci* 15(1):77-85.
Blecharz-Klin K, et al. (2012) "Effect of intranasal manganese administration on neurotransmission and spatial learning in rats" *Toxicol Appl Pharmacol* 265 (1):1-9.
Bonne, et al. (2001) "Longitudinal MRI study of hippocampal volume in trauma survivors with PTSD." *Am J Psychiatry* 158: 1248-1251.
Boscarino, J.E. (2006) "Posttraumatic stress disorder and mortality among U.S. Army veterans 30 years after military service." *Annal Epidemiol*. 16(4):248-56.
Bowman ER, Me KH, Jr. (1962) "Studies on the metabolism of (-)-cotinine in the human" *J Pharmacol Exp Ther* 135:306-311.
Bowman, et al. (2002) "Effects of chronic restraint stress and estradiol on open field activity, spatial memory, and monoaminergic neurotransmitters in ovariectomized rats." *Neuroscience* 113: 401-410.
Boyle, et al. (2007) "Anger and Depression Predict Increases in C3 over a 10-Year Period." *Brain Behav Immun* 21: 816-823.
Bozon B, et al. (2003) "A requirement for the immediate early gene zif268 in reconsolidation of recognition memory after retrieval" *Neuron* 40(4):695-701.
Bozon B, et al. (2003) "MAPK, CREB and zif268 are all required for the consolidation of recognition memory" *Philos Trans R Soc Lond B Biol Sci* 358(1432): 805-814.
Broide, et al. (1999) "The alpha7 nicotinic acetylcholine receptor in neuronal plasticity." *Mol Neurobiol* 20: 1-16.
Briggs, C.A. et al. (1995) "Human alpha 7 nicotinic acetylcholine receptor responses to novel ligands." *Neuropharmacology*. 34:583-90.
Brown AD, et al. (2009) "Cardiovascular abnormalities in patients with major depressive disorder: autonomic mechanisms and implications for treatment" *CNS Drugs* 10(7):583-602.
Buccafusco, J.J. et al. (2007) "Disconnection between activation and desensitization of autonomic nicotinic receptors by nicotine and cotinine." *Neurosci Lett*. 413:68-71.
Buhmann CB, et al. (2016) "The effect of flexible cognitive-behavioural therapy and medical treatment, including antidepressants on post-traumatic stress disorder and depression in traumatised refugees: pragmatic randomised controlled clinical trial" *Br J Psychiatry* 208(3):252-259.
Bunea R, et al. (2004) Evaluation of the effects of Neptune Krill Oil on the clinical course of hyperlipidemia. *Altern Med Rev* 9(4):420-428.
Burgess, et al. (2011) "Cotinine inhibits amyloid-β peptide neurotoxicity and oligomerization" *Clinical Toxicology* S6: 003.
Burghardt NS, et al. (2013) "Acute and chronic effects of selective serotonin reuptake inhibitor treatment on fear conditioning: implications for underlying fear circuits" *Neuroscience* 247:253-272.
Burri L, Johnsen L (2015) "Krill products: an overview of animal studies" *Nutrients* 7 (5):3300-3321.
Buynitsky, et al. (2009) "Restraint stress in biobehavioral research: Recent developments." *Neurosci Biobehav Rev* 33: 1089-1098.
Calhoun, P.S. et al. (2002) "Medical service utilization by veterans seeking help for posttraumatic stress disorder." *Am J Psychiatry*. 159(12):2081-6.
Cannich A, et al. (2004) "CB1 cannabinoid receptors modulate kinase and phosphatase activity during extinction of conditioned fear in mice" *Learn Mem* 11 (5):625-632.
Cao et al. (2004) "VEGF links hippocampal activity with neurogenesis, learning and memory." *Nat Genet* 36: 827-835.
Castagne V, et al. (2011) "Rodent models of depression: forced swim and tail suspension behavioral despair tests in rats and mice" *Curr. Protoc Neurosci Chapter* 8:Unit8 10A.
Chapman CD, et al. (2013) "Intranasal treatment of central nervous system dysfunction in humans" *Pharm Res* 30(10):2475-2484.
Chaturvedi RK, et al. (2008) "Mitochondrial approaches for neuroprotection" *Ann N Y Acad Sci* 1147:395-412.

(56) References Cited

OTHER PUBLICATIONS

Cherian, K.L., et al., (2009) "Chronic prenatal restraint stress induced memory impairment in passive avoidance task in post weaned male and female Wistar rats," *Indian J Exp Biol,* 47: 893-899.
Chiba, T., et al., (2012) "Chronic restraint stress causes anxiety- and depression-like behaviors, downregulates glucocorticoid receptor expression, and attenuates glutamate release induced by brain-derived neurotrophic factor in the prefrontal cortex," *Prog Neuropsychopharmacol Biol Psychiatry*, 39: 112-119.
Christie, et al. (2012) "Impaired cognitive function and hippocampabl neurogenesis following cancer chemotherapy." *Clin Cancer Res* 18: 1954-1965.
Chromy, B.A. et al. (2003) "Self-assembly of Aβ(1-42) into globular neurotoxins." *Biochemistry*. 42:12749-60.
Clemens, et al. (2009) "The addition of five minor tobacco alkaloids increases nicotine-induced hyperactivity, sensitization and intravenous self-administration in rats." *International J Neuropsychopharmacology* 12: 1355-1366.
Cobb, et al. (2016) "Density of GFAP-immunoreactive astrocytes is decreased in left hippocampi in major depressive disorder." *Neuroscience* 316: 209-220.
Colvonen, et al. (2017) "Pretreatment biomarkers predicting PTSD psychotherapy outcomes: A systemic review." *Neurosci Biobehav Rev* 75: 140-156.
Conrad, et al. (2010) "Impact of the hypothalamic-pituitary-adrenal/gonadal axes on trajectory of age-related cognitive decline." *Prog Brain Res* 182: 31-76.
Conrad, J., et al., (2004) "Acute stress impairs spatial memory in male but not female rats: influence of estrous cycle," *Pharmacol Biochem Behav*, 78: 569-579.
Conway, J.R. (2013) "Smoking while on chemotherapy." *Chemotherapy*.
Cordova MJ, et al. (2017) "Post-traumatic stress disorder and cancer" *Lancet Psychiatry* 17: 30014-7.
Costa, et al. (2016) "Age, environment, object recognition and morphological diversity of GFAP-immunolabeled astrocytes." *Behav Brain Funct* 12. 28.
Costantino HR, et al. (2008) "Intranasal administration of acetylcholinesterase inhibitors" *BMC Neurosci Suppl* 3:S6.
Court, J.A. et al. (2005) "Attenuation of Abeta deposition in the entorhinal cortex of normal elderly individuals associated with tobacco smoking." *Neuropathol Appl Neurobiol.* 31:522-35.
Court, J et al. (2001) "Nicotinic Receptor Abnormalities in Alzheimer's Disease." *Biol Psych*. 49(3):175-84.
Crooks, et al. (1999) "(S)-(-)-Cotinine, the Major Brain Metabolite of Nicotine, Stimulates Nicotinic Receptors to Evoke [$^3$h]Dopamine Release from Rat Striatal Slices in a Calcium-Dependent Manner." *The Journal of Pharmacology and Experimental Therapeutics* 288: 905-911.
Crotti and Glass (2015) "The choreography of neuroinflammation in Huntington's disease." *Trends Immunol* 36: 364-373.
Crozatier, et al. (2007) "Calcineurin (protein phosphatase 2B) is involved in the mechanisms of action of antidepressants." *Neuroscience* 144(4):1470-1476.
Czeh, et al. (2001) "Stress-induced changes in cerebral metabolites, hippocampal volume and cell proliferation are prevented by antidepressant treatment with tianeptine." *Proc Natl Acad Sci USA* 98: 12796-1280.
Czeh, et al. (2006) "Astroglial plasticity in the hippocampus is affected by chronic psychosocial stress and concomitant fluoxetine treatment." *Neuropsychopharmacology* 31: 1616-1626.
Czeh, et al. (2007) "Chronic social stress inhibits cell proliferation in the adult medial prefrontal cortex: hemispheric asymmetry and reversal by fluoxetine treatment." *Neuropsychopharmacology* 32: 1490-1503.
Dalia, et al. (2010) "Sex differences in animal models of depression and antidepressant response." *Basic Clin Pharmacol Toxicol* 106: 226-233.

Daura, X. et al. (1999) "Folding-unfolding thermodynamics of a β-heptapeptide from equilibrium simulations." *Proteins*. 34:269-80.
Davidson J, et al. (2001) "Efficacy of sertraline in preventing relapse of posttraumatic stress disorder: results of a 28-week double-blind, placebo-controlled study" *Am J Psychiatry* 158(12): 1974-1981.
Day, et al. (1998) "Effects of microgravity and bone morphogenetic protein II on GFAP in rat brain." *J Appl Physiol* 85: 716-722.
De Aguiar RB, et al. (2013) "Neuroactive effects of cotinine on the hippocampus: behavioral and biochemical parameters" *Neuropharmacology* 71 :292-298.
De Andrade, et al. (2012) "Acute restraint differently alters defensive responses and fos immunoreactivity in the rat brain." *Behav Brain Res* 232: 20-29.
De Bellis MD, et al. (2002) Brain structures in pediatric maltreatment-related posttraumatic stress disorder: a sociodemographically matched study. *Biol Psychiatry* 52(11):1066-1078.
De Bruin, et al. (2006) "Beneficial effects of galantamine on performance in the object recognition task in Swiss mice: deficits induced by scopolamine and by prolonging the retention interval." *Pharmacol Biochem Behav* 85: 253-260.
De la Fuente V, et al. (2011) "Reconsolidation or extinction: transcription factor switch in the determination of memory course after retrieval" *J Neurosci* 31(15):5562-5573.
De la Fuente V, et al. (2014) "Calcineurin phosphatase as a negative regulator of fear memory in hippocampus: control on nuclear factor-KB signaling in consolidation and reconsolidation" *Hippocampus* 24(12): 1549-1561.
Dhuria SV, et al. (2010) "Intranasal delivery to the central nervous system: mechanisms and experimental considerations" *J Pharm Sci* 99(4):1654-1673.
Dienel, G.A. (2017) "The metabolic trinity, glucose-glycogen-lactate, links astrocytes and neurons in brain energetics, signaling, memory, and gene expression." *Neurosci Lett* 637: 18-25.
D'Incamps, et al. (2014) "High affinity and low affinity heteromeric nicotinic acetylcholine receptors at central synapses." *J Physiol* 592: 4131-4136.
Drevets, et al. (2008) "Brain structural and functional abnormalities in mood disorders: implications for neurocircuitry models of depression." *Brain Struct Funct* 213:93-118.
Dunn AJ, et al. (2008) "Effects of acute and chronic stressors and CRF in rat and mouse tests for depression" *Ann N Y Acad Sci* 1148:118-126.
Echeverria, V. et al. (2002) "Intracellular A-beta amyloid, a sign for worse things to come?" *Mol Neurobiol*. 26(2-3):299-316.
Echeverria, V. et al. (2005) "Stimulation of PGE receptors EP2 and EP4 protects cultured neurons against oxidative stress and cell death following beta-amyloid exposure." *Eur J Neurosci*. 22:2199-206.
Echeverria Moran (2012) "Cotinine: Beyond that Expected, More than a Biomarker of Tobacco Consumption." *Frontiers in pharmacology* 3: 173.
Echeverria Moran (2014) "A new treatment for Alzheimers?" *Chileno The Chile Magazine*, Sep. 13, 2014.
Echeverria V, et al. (2016) "Neuroinflammation: A Therapeutic Target of Cotinine for the Treatment of Psychiatric Disorders?" *Curr Pharm Des* 22(10):1324-1333.
Echeverria V, et al. (2016) "Positive modulators of the alpha7 nicotinic receptor against neuroinflammation and cognitive impairment in Alzheimer's disease" *Prog Neurobiol* 144:142-157.
Echeverria, et al. (2008) "Raf inhibition protects cortical cells against β-amyloid toxicity," *Neuroscience Letters* 444: 92-96.
Echeverria, et al. (2009) "Sorafenib inhibits nuclear factors kappa B, decreases inducible nitric oxide synthase and cyclooxygenase-2 expression, and restores working memory in APPswe mice," *Neuroscience* 162: 1220-1231.
Echeverria V, et al. (2011) "Cotinine reduces amyloid-beta aggregation and improves memory in Alzheimer's disease mice" *J Alzheimers Dis* 24(4):817-835.
Echeverria, et al. (2016) "Advances in medicinal plants with effects on anxiety behavior associated to mental and health conditions," *Current Medicinal Chemistry* 23: 1-13.
Echeverria and Zeitlin (2012) "Cotinine: A Potential New Therapeutic Agent against Alzheimer's disease" *CNS Neurosciences & Therapeutics* 18: 517-523.

(56) References Cited

OTHER PUBLICATIONS

Echeverria, V. (Sep. 14, 2014) Contributor of "Chileno, The Chile Magazine." Retrieved from http://www.chileno.co.uk/contributors/valentina-echeverria-moran#.V6Ta0LgrluU.
Echeverria, V. (Aug. 5, 2016) Biography. U.S. Department of Veterans Affairs. Retrieved from http://www.hindawl.com/75609568.
Eisenberg M, et al. (2004) "Reconsolidation of fresh, remote, and extinguished fear memory in Medaka: old fears don't die" *Eur J Neurosci* 20(12): 3397-3403.
Eskandarian, S et al. (2013) "Effects of systemic administration of oxytocin on contextual fear extinction in a rat model of post-traumatic stress disorder." *Basic Clin Neurosci.* 4(4):315-22.
Evans, M.S. et al. (1998) "Electrophysiology of embryonic, adult and aged rat hippocampal neurons in serum-free culture." *J Neurosci Methods.* 79(1):37-46.
Exley, et al. (2008) "Presynaptic nicotinic receptors: a dynamic and diverse cholinergic filter of striatal dopamine neurotransmission." *Br J Pharmacol* 153 Suppl 1: S283-97.
Nagai, et al. (2007) "Astrocytes expressing ALS-linked mutated SOD I release factors selectively toxic to motor neurons." *Nat Neurosci* 10:615-622.
Naitoh, et al. (1992) "Behavioral assessment of antidepressants (1)—The forced swimming test: a review of its theory and practical application." *Yakubutsu Seishin Kodo* 12: 105-111.
Necula, M. et al. (2007) "Small molecule inhibitors of aggregation indicate that amyloid beta oligomerization and fibrillization pathways are independent and distinct." *J Biol Chem.* 282:10311-24.
Nestler, et al. (2002) "Neurobiology of depression." *Neuron* 34: 13-25.
Niranjan, R. (2014) "The role of inflammatory and oxidative stress mechanisms in the pathogenesis of Parkinson's disease: focus on astrocytes." *Mol Neurobiol* 49: 28-38.
Nordberg, A et al. (2002) "Chronic nicotine treatment reduces beta-amyloidosis in the brain of a mouse model of Alzheimer's disease (APPsw)." *J Neurochem.* 81:655-8.
Norcross, et al. (2008) "Effects of adolescent fluoxetine treatment on fear-, anxiety-or stress-related behaviors in C57BL/6J or BALB/cJ mice." *Psychopharmacology (Berl)* 200: 413-424.
North, et al. (2016) "The evolution of PTSD criteria across editions of DSM." *Ann Clin Psychiatry* 28: 197-208.
Oddo, S et al. (2005) "Chronic nicotine administration exacerbates tau pathology in a transgenic model of Alzheimer's disease." *Proc Natl Acad Sci USA.* 102:3046-51.
Oliveros-Matus, et al. (2020) "Cotinine enhances fear extinction and astrocyte survival by mechanisms involving the nicotinic acetylcholine receptors signaling" *Frontiers in Pharmacology* 11: Article 303.
Ong WY, et al. (2015) "Synthetic and Natural Inhibitors of Phospholipases A2: Their Importance for Understanding and Treatment of Neurological Disorders" *ACS Chern Neurosci.* 6(6): 814-31.
Ono, K et al. (2002) "Nicotine breaks down preformed Alzheimer's β-amyloid fibrils in vitro." *Biol Psychiatry.* 52:880-6.
Orlovsky, et al. (2014) "Hippocampus remodeling by chronic stress accompanied by GR, proteasome and caspase-3 overexpression." *Brain Res* 1593: 83-94.
Otani, et al. (2006) "Enhanced hippocampal neurodegeneration after traumatic or kainate excitotoxicity in GFAP-null mice." *J Clin Neurosci* 13: 934-938.
Ott V, et al. (2012) "Intranasal administration of insulin to the brain impacts cognitive function and peripheral metabolism" *Diabetes Obes Metab* 14(3):214-221.
Palgi S, et al. (2016) "Oxytocin improves compassion toward women among patients with PTSD" *Psychoneuroendocrinology* 64:143-149.
Pare, et al. (1986) "Restraint stress in biomedical research: a review." *Neurosci Biobehav Rev* 10: 339-370.

Patel, et al. (2014) "Cotinine halts the advance of Alzheimer's disease-like pathology and associated depressive-like behavior in Tg6799 mice." *Front Aging Neurosci* 6: 162.
Pavlides, et al. (2002) "Effects of chronic stress on hippocampal long-term potentiation." *Hippocampus* 12: 245-257.
Peng, S et al. (2009) "Decreased Brain-Derived Neurotrophic Factor Depends on Amyloid Aggregation State in Transgenic Mouse Models of Alzheimer's Disease" *J Neurosci.* 29(29):9321-9.
Pereira-Figueiredo I, et al. (2017) "Long-Term Sertraline Intake Reverses the Behavioral Changes Induced by Prenatal Stress in Rats in a Sex-Dependent Way" *Front Behav Neurosci* 11:99.
Perez-Urrutia N, et al. (2017) "Intranasal cotinine improves memory, and reduces depressive-like behavior, and GFAP+ cells loss induced by restraint stress in mice" *Exp Neurol* 295:211-221.
Perrine, et al. (2016) "Severe, multimodal stress exposure induces PTSD-like characteristics in a mouse model of single prolonged stress." *Behav Brain Res* 303: 228-237.
Philip NS, et al. (2010) "Pharmacologic approaches to treatment resistant depression: a re-examination for the modern era" *Expert Opin Pharmacother* 11(5):709-15, 722.
Pichon, et al. (2004) "Some aspects of the physiological role of ion channels in the nervous system." *Eur Biophys J* 33: 211-226.
Polli JW, et al. (1991) "Expression of the calmodulin-dependent protein phosphatase, calcineurin, in rat brain: developmental patterns and the role of nigrostriatal innervation" *Brain Res Dev Brain Res* 63(1-2):105-119.
Polotow, S.C., et al. (2015) "Redox Status and Neuro Inflammation Indexes in Cerebellum and Motor Cortex of Wistar Rats Supplemented with Natural Sources of Omega-3 Fatty Acids and Astaxanthin: Fish Oil, Krill Oil, and Algal Biomass" *Mar Drugs* 13: 6117-6137.
Press release, "Tobacco-derived compound prevents memory loss in Alzheimer's disease mice" (Apr. 27, 2011). Retrieved from https://hscweb3.hsc.usf.edu/edu/health/now/?p=18667.
Press release, "Nicotine byproduct shows promise in treating depression, memory loss." (May 22, 2014). Retrieved from http://www.research.va.goc/currents/spring2014/spring2014-40.cfm.
Quirk, G.J. et al. (2006) "Prefrontal Mechanisms in Extinction of Conditioned Fear." *Biol Psychiatry.* 60:337-43.
Radford, et al. (2015) "The established and emerging roles of astrocytes and microglia in amyotrophic lateral sclerosis and frontotemporal dementia." *Front Cell Neurosci* 9: 414.
Raison, et al. (2006) "Cytokines sing the blues: inflammation and the pathogenesis of depression." *Trends Immuno.* 27: 24-31.
Rammal H, et al. (2008) "Evidence that oxidative stress is linked to anxiety-related behaviour in mice" *Brain Behav Immun* 22(8): 1156-1159.
Rauch SL, et al. (2000) "Exaggerated amygdala response to masked facial stimuli in posttraumatic stress disorder: a functional MRI study" *Biol Psychiatry* 47(9):769-776.
Reagan, et al. (2008) "The As and Ds of stress: metabolic, morphological and behavioral consequences." *Eur J Pharmacol* 585: 64-75.
Rehani K, et al. (2008) "Cotinine-induced convergence of the cholinergic and PI3 kinase-dependent anti-inflammatory pathways in innate immune cells" *Biochim Biophys Acta* 1783(3):375-382.
Ross TM, et al. (2008) "Intranasal administration delivers peptoids to the rat central nervous system" *Neurosci Lett* 439(1):30-33.
Rotaru, et al. (2016) "A Meta-Analysis for the Efficacy of Hypnotherapy in Alleviating PTSD Symptoms." *Int J Clin Exp Hypn* 64: 116-136.
Ruigrok MJ, et al. (2015) "Emerging Insights for Translational Pharmacokinetic and Pharmacokinetic-Pharmacodynamic Studies: Towards Prediction of Nose-to-Brain Transport in Humans" *Aaps J* 17(3):493-505.
Sachser RM, et al. (2016) "Forgetting of long-term memory requires activation of NMDA receptors, L-type voltage-dependent Ca2+ channels, and calcineurin" *Sci Rep* 6:22771.
Sairanen M, et al. (2007) "Chronic antidepressant treatment selectively increases expression of plasticity-related proteins in the hippocampus and medial prefrontal cortex of the rat" *Neuroscience* 144(1):368-374.
Salomon, et al. (1996) "Nicotine Inhibits Amyloid Formation by the Beta-Peptide" *Biochem.* 35: 13568-13578.

(56) References Cited

OTHER PUBLICATIONS

Santha, et al. (2015) "Restraint Stress-Induced Morphological Changes at the Blood-Brain Barrier in Adult Rats." Front Mol Neurosci 8: 88.
Saur, et al. (2016) "Experimental Post-traumatic Stress Disorder B14720 Decreases Astrocyte Density and Changes Astrocytic Polarity in the CA1 Hippocampus of Male Rats." Neurochem Res 41: 892-904.
Schaffner, et al. (2001) "The effect of type 1 astrocytes on neuronal complexity: a fractal analysis." Methods 24: 323-329.
Scharfman, et al. (2014) "Differential regulation of BDNF, synaptic plasticity and sprouting in the hippocampal mossy fiber pathway of male and female rats." Neuropharmacology 76 Pt C: 696-708.
Schmitz, et al. (2002) "Depression: reduced number of granule cells in the hippocampus of female, but not male, rats due to prenatal restraint stress." Mol Psychiatry 7: 810-813.
Schnurr, P. et al. (2002) "Research on Posttraumatic Stress Disorder: Epidemiology, Pathophysiology, and Assessment." J Clin Psychol. 58(8):877-89.
Schousboe, et al. (1992) "Regulatory role of astrocytes for neuronal biosynthesis and homeostasis of glutamate and GABA." Prog Brain Res 94: 199-211.
Schuettelkopf, A.W. et al. (2004) "PRODRG—a tool for high-throughput crystallography of proteinligand complexes." Acta Crystallographica. 60:1355-63.
Sen B, et al. (2009) "Mechanical loading regulates NFATc1 and beta-catenin signaling through a GSK3beta control node" J Biol Chem 284 (50):34607-34617.
Seo JS, et al. (2011)"Behavioral stress causes mitochondrial dysfunction via ABAD up-regulation and aggravates plaque pathology in the brain of a mouse model of Alzheimer disease" Free Radic Biol Med 50 (11):1526-1535.
Shaw JA, et al. (2012) "Role of calcineurin in inhibiting disadvantageous associations" Neuroscience 203:144-152.
Sheline (2000) "3D MRI studies of neuroanatomic changes in unipolar major depression: the role of stress and medical comorbidity." Biol Psychiatry 48: 791-800.
Sheynin, et al. (2016) "Circuit dysregulation and circuit-based treatments in posttraumatic stress disorder." Neurosci Lett. 649: 133-138.
Silva AJ, et al. (1998) CREB and memory: Annu Rev Neurosci 21:127-148.
Sofroniew, et al. (2010) "Astrocytes: biology and pathology." Acta Neuropathol 119(15): 7-35.
Song, et al. (2007) "Omega-3 fatty acid eicosapentaenoic acid. A new treatment for psychiatric and neurodegenerative diseases: a review of clinical investigations." Expert Opinion on Investigational Drugs 16(10): 1627-1628.
Spence, et al. (2011) "Neuroprotection mediated through estrogen receptor-alpha in astrocytes." Proc Natl Acad Sci U S A 108: 8867-8872.
Stander, et al. (2014) "Etiology of depression comorbidity in combat-related PTSD: a review of the literature." Clin Psychol Rev 34: 87-98.
Stein DJ, et al. (2006) "Pharmacotherapy for post traumatic stress disorder (PTSD)" Cochrane Database Syst Rev 2006(1): CD002795.
Stobart, et al. (2013) "Multifunctional role of astrocytes as gate-keepers of neuronal energy supply." Front Cell Neurosci 7: 38.
Sublette ME, et al. (2011) "Meta-analysis of the effects of eicosapentaenoic acid (EPA) in clinical trials in depression" J Clin Psychiatry 72 (12):1577-1584.
Sun, et al. (2006) "Vascular endothelial growth factor-B (VEGFB) stimulates neurogenesis: evidence from knockout mice and growth factor administration." Developmental biology 289: 329-335.
Szczepanik, et al. (2016) "Amygdala response to explicit sad face stimuli at baseline predicts antidepressant treatment response to scopolamine in major depressive disorder." Psychiatry Res 254: 67-73.
Szymanska, I. et al., Electrochemical impedance spectroscopy for study of amyloid β-peptide interactions with (−) nicotine ditartrate and (−) cotinine. Biosens Bioelectron. 2007; 22:1955-60.

Tafet, et al. (2003) "Psychoneuroendocrinological links between chronic stress and depression." Prog Neuropsychopharmacol Biol Psychiatry 27: 893-903.
Teicher, et al. (2012) "Childhood maltreatment is associated with reduced volume in the hippocampal subfields CA3, dentate gyrus, and subiculum." Proc Natl Acad Sci U S A 109: E563-572.
Terry, A.V., Jr. et al. (2005) "Cotinine, a neuroactive metabolite of nicotine: potential for treating disorders of impaired cognition." CNS Drug Rev. 11:229-52.
Terry, et al. (2015) "R-(+) and s-(−) isomers of cotinine augment cholinergic responses in vitro and in vivo." J Pharmacol Exp Ther 352: 405-418.
Thorsell, M., et al. (2000), "Behavioral insensitivity to restraint stress, absent fear suppression of behavior and impaired spatial learning in transgenic rats with hippocampal neuropeptide Y overexpression," Proc Natl Acad Sci USA, 97: 12852-12857.
Tian, et al. (2012) "A study of the functional significance of epidermal growth factor in major depressive disorder." Psychiatr. Genet. 22: 161-7.
Tong, L. et al. (2004) "β-amyloid peptide at sublethal concentrations downregulates brain-derived neurotrophic factor functions in cultured cortical neurons." J Neurosci. 24(30) :6799-809.
"Trauma- and Stressor-Related Disorders" in the Diagnostic and Statistical Manual of Mental Disorders, Fifth Edition, American Psychiatric Association, 2013 (22 pages).
Trevizol, et al. (2016) "Transcranial magnetic stimulation for post-traumatic stress disorder: an updated systematic review and meta-analysis." Trends Psychiatry Psychother 38: 50-55.
Triguero, L. et al. (2008) "Comparative molecular dynamics studies of wild-type and oxidized forms of full-length Alzheimer amyloid β-peptides Aβ(1-40) and Aβ(1-42)." J Phys Chern B. 112:7123-31.
Tymen, et al. (2013) "Restraint stress alters neutrophil and macrophage phenotypes during wound healing." Brain Behav Immun 28: 207-217.
Ugbode, et al. (2017) "Astrocytic transporters in Alzheimer's disease." Biochem J 474: 333-355.
Unger, C. et al. (2005) "Early changes in Abeta levels in the brain of APPswe transgenic mice—implication on synaptic density, alpha7 neuronal nicotinic acetylcholine- and N-methyl-D-aspartate receptor levels." Mol Cell Neurosci. 30:218-27.
Vainio, P.J. et al. (2001) "Cotinine Binding to Nicotinic Acetylcholine Receptors in Bovine Chromaffin Cell and Rat Brain Membranes." Nic Tobac Res. 3:177-82.
Verkhratsky, et al. (2013) "Astroglia in neurological diseases." Future Neurol 8:149-158.
Vigerust, et al. (2013) "Krill oil versus fish oil in modulation of inflammation and lipid metabolism in mice transgenic for TNF-alpha" Eur J Nutr 52(4):1315-1325.
Villapol, et al. (2014) "Temporal dynamics of cerebral blood flow, cortical damage, apoptosis, astrocyte-vasculature interaction and astrogliosis in the pericontusional region after traumatic brain injury." Front Neurol 5: 82.
Villarreal, et al. (2002) "Reduced hippocampal volume and total white matter volume in posttraumatic stress disorder." Biol Psychiatry 52: 119-125.
Wang J, et al. (2003) "Interaction of calcineurin and type-A GABA receptor gamma 2 subunits produces long-term depression at CA1 inhibitory synapses" J Neurosci 30 (3):826-836.
Wang, et al. (2015) "Modulation of social deficits and repetitive behaviors in a mouse model of autism: the role of the nicotinic cholinergic system." Psychopharmacology (Berl) 232: 4303-4316.
Watanabe, et al. (1992) "Stress induces atrophy of apical dendrites of hippocampal CA3 pyramidal neurons." Brain Res 588: 341-345.
Webster, et al. (2005) "Glial fibrillary acidic protein mRNA levels in the cingulate cortex of individuals with depression, bipolar disorder and schizophrenia." Neuroscience 133: 453-461.
Webster, et al. (2017) "Inflammation in epileptogenesis after traumatic brain injury." J Neuroinflammation 14: 10.
Weinstein, et al. (1991) "Suppression by antisense mRNA demonstrates a requirement for the glial fibrillary acidic protein in the formation of stable astrocytic processes in response to neurons." J Cell Biol 112: 1205-1213.

(56) References Cited

OTHER PUBLICATIONS

Wibrand K, et al. (2013) "Enhanced cognitive function and antidepressant-like effects after krill oil supplementation in rats" *Lipids Health Dis* 12:6.
Wijendran V, et al. (2002) "Efficacy of dietary arachidonic acid provided as triglyceride or phospholipid as substrates for brain arachidonic acid accretion in baboon neonates" *Pediatr Res* 51 (3):265-272.
Wildcbocr-Aiidrud, et al. (2014) "Cotinine impacts sensory processing in DBA/2 mice through changes in the conditioning amplitude." *Pharmacol Biochem Behav* 117: 144-150.
Wilder Schaaf, et al. (2013) "Anxiety, depression, and PTSD following cardiac arrest: a systematic review of the literature." *Resuscitation* 84: 873-877.
Williams, et al. (2015) "Sleep disorders in combat-related PTSD." *Sleep Breath* 19: 175-182.
Winkler, et al. (2015) "GLUT1 reductions exacerbate Alzheimer's disease vasculo-neuronal dysfunction and degeneration." *Nat Neurosci* 18: 521-530.
Winther B, et al. (2011) "Elucidation of phosphatidylcholine composition in krill oil extracted from Euphausia superba" *Lipids* 46 (1):25-36.
Wisniewski, et al. (1985) "Alzheimer's disease in Down's syndrome" *Neurology* 35: 957-961.
Witichen, H. et al. (2009) "Posttraumatic Stress Disorder: Diagnostic and Epidemiological Perspectives." *CNS Spectr.* 14(1 Suppl 1):5-12.
Woods, J. (2011) "Chemotherapy-induced cognitive impairment is associated with decreases in cell proliferation and histone modifications." *BMC Neurosci* 12: 124.
Xia, et al. (2013) "FGF2 blocks PTSD symptoms via an astrocyte-based mechanism." *Behav Brain Res* 256: 472-480.
Yamanaka, et al. (2008) "Astrocytes as determinants of disease progression in inherited amyotrophic lateral sclerosis." *Nat Neurosci* 11: 251-253.
Yang (2002) "ErbB2 Overexpression Correlates with Increased Expression of Vascular Endothelial Growth Factors A, C, and D in Human Breast Carcinoma." *American Cancer Society* 94: 2855-61.
Yang CH, et al. (2012) "Venlafaxine facilitates between-session extinction and prevents reinstatement of auditory-cue conditioned fear" Behav Brain Res 230 (1):268-27.
Yang Y, et al. (2013) "Intranasal insulin ameliorates tau hyperphosphorylation in a rat model of type 2 diabetes" *J Alzheimers Dis* 33 (2):329-338.
Yang, C., et al. (2005) "Behavioral stress enhances hippocampal CA1 long-term depression through the blockade of the glutamate uptake" *J Neurosci*, 25: 4288-4293.
Yang, et al. (2015) "Effects of SPAK knockout on sensorimotor gating, novelty exploration, and brain area-dependent expressions of NKCC 1 and KCC2 in a mouse model of schizophrenia." *Prog Neuropsychopharmacol Biol Psychiatry* 61: 30-3.
Yang, F. et al. (2005) "Curcumin Inhibits Formation of Amyloid β Oligomers and Fibrils, Binds Plaques, and Reduces Amyloid in Vivo." *J Biol Chern.* 280(7):5892-901.
Yolton, K., et al. (2005) "Exposure to environmental tobacco smoke and cognitive abilities among U.S. children and adolescents." *Environ Health Perspect.* 113(1):98-103.
York, D.M. et al. (1994) "Atomic-level accuracy in simulations of large protein crystals." *Proc Natl Acad Sci USA.* 91:8715-8.
Yoon, et al. (2017) "Recovery from Posttraumatic Stress Requires Dynamic and Sequential Shifts in Amygdalar Connectivities." *Neuropsychopharmacology* 42: 454-461.
Yuen, J., et al. (2012) "Repeated stress causes cognitive impairment by suppressing glutamate receptor expression and function in prefrontal cortex," *Neuron*, 73: 962-977.
Zeitlin R, et al. (2012) "Cotinine enhances the extinction of contextual fear memory and reduces anxiety after fear conditioning" *Behav Brain Res* 228(2):284-293.
Zeng, et al. (2001) "Nicotine and Amyloid Formation" *Biol. Psychiatry* 49: 248-257.
Zhou, et al. (2007) "Neuronal nitric oxide synthase contributes to chronic stress-induced depression by suppressing hippocampal neurogenesis." *Journal of Neurochemistry* 103: 1843-1854.
Zhu WL,et al. (2011) "Hippocampal CA3 calcineurin activity participates in depressive-like behavior in rats" *J Neurochem* 117(6):1075-1086.
Zhu, et al. (2016) "Altered resting state functional connectivity of fear and reward circuitry in comorbid PTSD and major depression." *Depress Anxiety.* 34(7): 641-650.
Zschocke, N., et al. (2005) "Differential promotion of glutamate transporter expression and function by glucocorticoids in astrocytes from various brain regions" *J Biol Chem*, 280: 34924-34932.
International Search Report and Written Opinion dated Oct. 3, 2018 by the International Searching Authority for International Application No. PCT/IB2018/000306, filed on Feb. 16, 2018, and published as WO 2018/150276 on Aug. 23, 2018 (Applicant-Universidad San Sebastian) (10 Pages).
International Preliminary Report on Patentability dated Aug. 2, 2019 by the International Searching Authority for International Application No. PCT/IB2018/000306, filed on Feb. 16, 2018, and published as WO 2018/150276 on Aug. 23, 2018 (Applicant-Universidad San Sebastian) (11 Pages).
International Search Report and Written Opinion dated May 6, 2016 by the International Searching Authority for International Application No. PCT/US2015/058625, filed on Nov. 2, 2015, and published as WO 2016/070181 on May 6, 2016 (Applicant-Department of Veterans Affairs, et al.) (7 Pages).
International Preliminary Report on Patentability dated May 2, 2017 by the International Searching Authority for International Application No. PCT/US2015/058625, filed on Nov. 2, 2015, and published as WO 2016/070181 on May 6, 2016 (Applicant-Department of Veterans Affairs, et al.) (6 Pages).
Restriction Requirement dated Dec. 8, 2017 by the USPTO for U.S. Appl. No. 15/583,937, filed May 1, 2017 and published as 2017/029652 on Oct. 19, 2017 (Inventor-Valentina Echeverria Moran) (7 Pages).
Response to Restriction Requirement filed on Mar. 8, 2018 for U.S. Appl. No. 15/583,937, filed May 1, 2017 and published as 2017/029652 on Oct. 19, 2017 (Inventor-Valentina Echeverria Moran) (8 Pages).
Non-final Office Action dated Aug. 16, 2018 by the USPTO for U.S. Appl. No. 15/583,937, filed May 1, 2017 and published as 2017/029652 on Oct. 19, 2017 (Inventor-Valentina Echeverria Moran) (14 Pages).
Response to Non-final Office Action dated Nov. 15, 2018 for U.S. Appl. No. 15/583,937, filed May 1, 2017 and published as 2017/029652 on Oct. 19, 2017 (Inventor-Valentina Echeverria Moran) (9 Pages).
Notice of Allowance dated Mar. 21, 2019 by the USPTO for U.S. Appl. No. 15/583,937, filed May 1, 2017 and published as 2017/029652 on Oct. 19, 2017 (Inventor-Valentina Echeverria Moran) (10 Pages).
Restriction Requirement dated Jul. 14, 2011 by the USPTO for U.S. Appl. No. 12/586,681, filed Sep. 24, 2009 and now U.S. Pat. No. 9,801,865 on Oct. 31, 2017 (Inventor-Valentina Echeverria Moran) (7 Pages).
Response to Restriction Requirement filed on Sep. 14, 2011 with the USPTO for U.S. Appl. No. 12/586,681, filed Sep. 24, 2009 and now U.S. Pat. No. 9,801,865 on Oct. 31, 2017 (Inventor-Valentina Echeverria Moran) (2 Pages).
Non-final Office Action dated Oct. 28, 2011 by the USPTO for U.S. Appl. No. 12/586,681, filed Sep. 24, 2009 and now U.S. Pat. No. 9,801,865 on Oct. 31, 2017 (Inventor-Valentina Echeverria Moran) (13 Pages).
Response to Non-final Office Action filed on Feb. 28, 2012 with the USPTO for U.S. Appl. No. 12/586,681, filed Sep. 24, 2009 now U.S. Pat. No. 9,801,865 on Oct. 31, 2017 (Inventor-Valentina Echeverria Moran) (11 Pages).
Final Office Action dated May 22, 2012 by the USPTO for U.S. Appl. No. 12/586,681, filed Sep. 24, 2009 now U.S. Pat. No. 9,801,865 on Oct. 31, 2017 (Inventor-Valentina Echeverria Moran) (15 Pages).

(56) References Cited

OTHER PUBLICATIONS

Response to Final Office Action filed on Oct. 22, 2012 with the USPTO for U.S. Appl. No. 12/586,681, filed Sep. 24, 2009 now U.S. Pat. No. 9,801,865 on Oct. 31, 2017 (Inventor-Valentina Echeverria Moran) (13 Pages).
Non-final Office Action dated Jul. 18, 2013 by the USPTO for U.S. Appl. No. 12/586,681, filed Sep. 24, 2009 now U.S. Pat. No. 9,801,865 on Oct. 31, 2017 (Inventor-Valentina Echeverria Moran) (15 Pages).
Response to Non-final Office Action filed on Dec. 18, 2013 with the USPTO for U.S. Appl. No. 12/586,681, filed Sep. 24, 2009 now U.S. Pat. No. 9,801,865 on Oct. 31, 2017 (Inventor-Valentina Echeverria Moran) (9 Pages).
Final Office Action dated Feb. 26, 2014 by the USPTO for U.S. Appl. No. 12/586,681, filed Sep. 24, 2009 now U.S. Pat. No. 9,801,865 on Oct. 31, 2017 (Inventor-Valentina Echeverria Moran) (13 Pages).
Response to Final Office Action filed on Jun. 26, 2014 with the USPTO for U.S. Appl. No. 12/586,681, filed Sep. 24, 2009 now U.S. Pat. No. 9,801,865 on Oct. 31, 2017 (Inventor-Valentina Echeverria Moran) (11 Pages).
Non-final Office Action dated Apr. 3, 2015 by the USPTO for U.S. Appl. No. 12/586,681, filed Sep. 24, 2009 now U.S. Pat. No. 9,801,865 on Oct. 31, 2017 (Inventor-Valentina Echeverria Moran) (12 Pages).
Response to Non-final Office Action filed on Sep. 3, 2015 with the USPTO for U.S. Appl. No. 12/586,681, filed Sep. 24, 2009 now U.S. Pat. No. 9,801,865 on Oct. 31, 2017 (Inventor-Valentina Echeverria Moran) (12 Pages).
Final Office Action dated Oct. 22, 2015 by the USPTO for U.S. Appl. No. 12/586,681, filed Sep. 24, 2009 now U.S. Pat. No. 9,801,865 on Oct. 31, 2017 (Inventor-Valentina Echeverria Moran) (9 Pages).
Response to Final Office Action filed on Feb. 22, 2016 with the USPTO for U.S. Appl. No. 12/586,681, filed Sep. 24, 2009 now U.S. Pat. No. 9,801,865 on Oct. 31, 2017 (Inventor-Valentina Echeverria Moran) (12 Pages).
Non-final Office Action dated Aug. 11, 2016 by the USPTO for U.S. Appl. No. 12/586,681, filed Sep. 24, 2009 now U.S. Pat. No. 9,801,865 on Oct. 31, 2017 (Inventor-Valentina Echeverria Moran) (11 Pages).
Response to Non-final Office Action filed on Feb. 13, 2017 with the USPTO for U.S. Appl. No. 12/586,681, filed Sep. 24, 2009 now U.S. Pat. No. 9,801,865 on Oct. 31, 2017 (Inventor-Valentina Echeverria Moran) (24 Pages).
Supplemental Response to Non-final Office Action filed on Apr. 11, 2017 with the USPTO for U.S. Appl. No. 12/586,681, filed Sep. 24, 2009 now U.S. Pat. No. 9,801,865 on Oct. 31, 2017 (Inventor-Valentina Echeverria Moran)(4 Pages).
Final Office Action dated May 2, 2017 by the USPTO for U.S. Appl. No. 12/586,681, filed Sep. 24, 2009 now U.S. Pat. No. 9,801,865 on Oct. 31, 2017 (Inventor-Valentina Echeverria Moran) (10 Pages).
Response to Final Office Action filed on Aug. 2, 2017 with the USPTO for U.S. Appl. No. 12/586,681, filed Sep. 24, 2009 now U.S. Pat. No. 9,801,865 on Oct. 31, 2017 (Inventor-Valentina Echeverria Moran) (65 Pages).
Notice of Allowance dated Aug. 28, 2017 by the USPTO for U.S. Appl. No. 12/586,681, filed Sep. 24, 2009 now U.S. Pat. No. 9,801,865 on Oct. 31, 2017 (Inventor-Valentina Echeverria Moran) (5 Pages).
Non-final Office Action dated Feb. 23, 2018 by the USPTO for U.S. Appl. No. 15/725,079, filed Oct. 4, 2017 now U.S. Pat. No. 10,238,641 on Mar. 26, 2019 (Inventor-Valentina Echeverria Moran) (14 Pages).
Response to Non-final Office Action filed on Jul. 23, 2018 with the USPTO for U.S. Appl. No. 15/725,079, filed Oct. 4, 2017 now U.S. Pat. No. 10,238,641 on Mar. 26, 2019 (Inventor-Valentina Echeverria Moran) (63 Pages).
Notice of Allowance issued on Nov. 21, 2018 by the USPTO for U.S. Appl. No. 15/725,079, filed Oct. 4, 2017 now U.S. Pat. No. 10,238,641 on Mar. 26, 2019 (Inventor-Valentina Echeverria Moran) (2 Pages).
Non-final Office Action dated Mar. 20, 2019 by the USPTO for U.S. Appl. No. 16/267,301, filed Feb. 4, 2019 and published as US-2019-0167653-A1 on Jun. 6, 2019 (Inventor-Valentina Echeverria Moran) (15 Pages).
Response to Non-final Office Action filed on Aug. 20, 2019 with the USPTO for U.S. Appl. No. 16/267,301, filed Feb. 4, 2019 and published as US-2019-0167653-A1 on Jun. 6, 2019 (Inventor-Valentina Echeverria Moran) (9 Pages).
Final Office Action dated Sep. 17, 2019 by the USPTO for U.S. Appl. No. 16/267,301, filed Feb. 4, 2019 and published as US-2019-0167653-A1 on Jun. 6, 2019 (Inventor-Valentina Echeverria Moran) (13 Pages).
Response to Final Office Action filed on Dec. 16, 2019 with the USPTO for U.S. Appl. No. 16/267,301, filed Feb. 4, 2019 and published as US-2019-0167653-A1 on Jun. 6, 2019 (Inventor-Valentina Echeverria Moran) (13 Pages).
Non-final Office Action dated Apr. 16, 2020 by the USPTO for U.S. Appl. No. 16/267,301, filed Feb. 4, 2019 and published as US-2019-0167653-A1 on Jun. 6, 2019 (Inventor-Valentina Echeverria Moran) (14 Pages).
Response to Office Action filed on Sep. 16, 2020 by the USPTO for U.S. Appl. No. 16/267,301, filed Feb. 4, 2019 and published as US-2019-0167653-A1 on Jun. 6, 2019 (Inventor-Valentina Echeverria Moran) (23 Pages).
Final Office Action dated Oct. 13, 2020 by the USPTO for U.S. Appl. No. 16/267,301, filed Feb. 4, 2019 and published as US-2019-0167653-A1 on Jun. 6, 2019 (Inventor-Valentina Echeverria Moran) (14 Pages).
Bernert et al. Effects of a single transdermal nicotine dose on cognitive performance in adults with Down syndrome. *J Neural Transm Suppl.* 2001;(61):237-245. Abstract.
Chromy et al. Self-Assembly of $A\beta_{1-42}$ into Globular Neurotoxins. *Biochemistry* 2003; 42: 12749-12760.
Haass and Selkoe. Soluble protein oligomers in neurodegeneration: lessons from the Alzheimer's amyloid β-peptide. *Nat Rev Mol Cell Biol* 2007;8:101-12.
Halldin, et al. (1992) (S)- and (R)-[11C]nicotine and the metabolite (R/S)-[11C]cotinine. Preparation, metabolite studies and in vivo distribution in the human brain using PET. *Int J Rad Appl Instrum B* 19(8): 871-80.
Howe MN, Price IR. Effects of transdermal nicotine on learning, memory, verbal fluency, concentration, and general health in a healthy sample at risk for dementia. *International Psychogeriatrics* 2001 ;13(4):465-75.
Echeverria et al. Rat transgenic models with a phenotype of intracellular Abeta accumulation in hippocampus and cortex. *J. Alzheimer's Dis.* 6(3): 209-19, 2004.
Echeverria V, et al. Altered mitogen-activated protein kinase signaling, tau hyperphosphorylation and mild spatial learning dysfunction in transgenic rats expressing the beta-amyloid peptide intracellularly in hippocampal and cortical neurons. *Neuroscience.* 129(3): 583, 2004.
Echeverria V, et al. Oligomers of beta-amyloid peptide block BDNF-induced Arc expression in cultured cortical neurons. *Curr Aiz Res.* 4 (5):518-52, 2007.
Knott V, Engeland C, Mohr E, Mahoney C, Ilivitsky V. Acute nicotine administration in Alzheimer's disease: an exploratory EEG study. *Neuropsychobiology* 2000;41(4):210-20.
Knott V, Mohr E, Mahoney C, Engeland C, Ilivisky V. Effects of acute nicotine administration on cognitive event related potentials in tacrine-treated and non-treated patients with Alzheimer's disease. *Neuropsychobiology* 2002;45:156-60.
Laurén et al. Cellular prion protein mediates impairment of synaptic plasticity by amyloid-beta oligomers. *Nature.* 2009;457(7233):1128-1132. doi:10.1038/nature07761.
Lopez-Arrieta JLA, Sanz FJ. Nicotine for Alzheimer's disease. *Cochrane Database of Systematic Reviews* 2001, Issue 2.[DOI: 10.1002/14651858.CD001749].

(56) References Cited

OTHER PUBLICATIONS

Newhouse et al. Intravenous nicotine in Alzheimer's disease: a pilot study. *Psychopharmacology* 1988; 95:171-5.
Newhouse et al. Nicotinic Treatment of Alzheimer's Disease. *Biol Psychiatry* 2001; 49; 268-278.
Pigino et al. Disruption of fast axonal transport is a pathogenic mechanism for intraneuronal amyloid beta. *PNAS* 2009; 106(14): 5907-5912.
Sahakian B, Jones G, Levy R, Gray J, Warburton DM. The effects of nicotine on attention, information processing and short-term memory. British Journal of *Psychiatry* 1989;154:797-800.
Sahakian BK, Coull JT. Nicotine and tetrahydroaminoacridine:evidence for improved attention in patients with dementia of the Alzheimer type. *Drug Development and Research* 1994;31 (1):80-8.
Shankar et al. Amyloid-β protein dimers isolated directly from Alzheimer's brains impair synaptic plasticity and memory. *Nature Medicine* 2008;14:837-42.
Snaedel J, Johannesson T, Jonsson JE, Gylfadottir G. The effects of nicotine in dermal plaster on cognitive functions in patients with Alzheimer's disease. *Dementia* 1996;7(1):47-52.
White HK, Levin ED. Four-week nicotine skin patch treatment effects on cognitive performance in Alzheimer's disease. *Psychopharmacology* 1999; 143(2):158-65.
White HK, Levin ED. Chronic transdermal nicotine patch treatment effects on cognitive performance in age-associated memory impairment. *Psychopharmacology* 2004;171:465-71.
Wilson AL, Langley LK, Monley J, Bauer T, Rottunda S, et al. Nicotine patches in Alzheimer's disease: pilot study on learning, memory, and safety. *Pharmacologyand Biochemistry of Behavior* 1995;51(2-3) :509-14.
López-Arrieta et al. Efficacy and safety of nicotine on Alzheimer's disease patients. *Cochrane Database Syst Rev.* 2001 ;(2):CD001749.
Wilson et al. Transdermal nicotine administration in Alzheimer's disease: effects on cognition, behavior and cardiac function. In: Iqbal K, Mortimer JA, Wimblad B,Wisniewki HM editor(s). *Research Advances in Alzheimer's Disease and Related Disorders*. Chichester, New York, Brisbane, Toronto, Singapore: John Wiley and Sons, 1995:30514.
Final Office Action mailed by the USPTO dated Oct. 13, 2020 for U.S. Appl. No. 16/267,301, filed Feb. 4, 2019 and published as US 2019/0167653 A1 on Jun. 6, 2019 (Applicant—The United States Government as represented by the Department of Veterans Affairs) (14 pages).

* cited by examiner

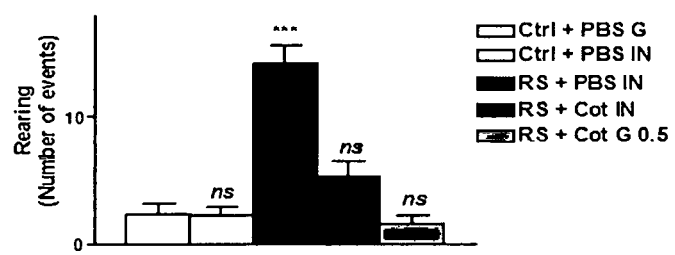
Fig. 1 A  Elevated plus maze
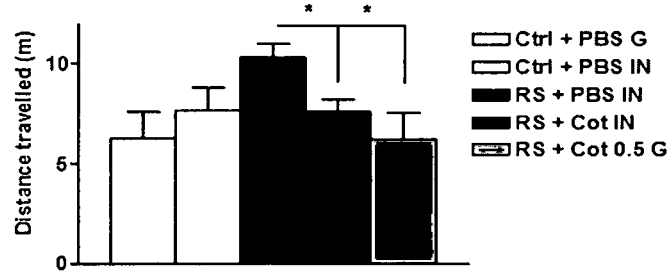
Fig. 1 B
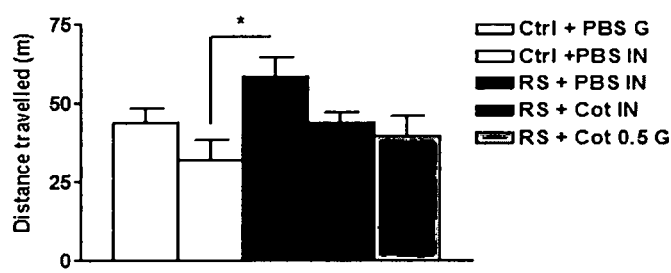
Fig. 1 C  Open Field

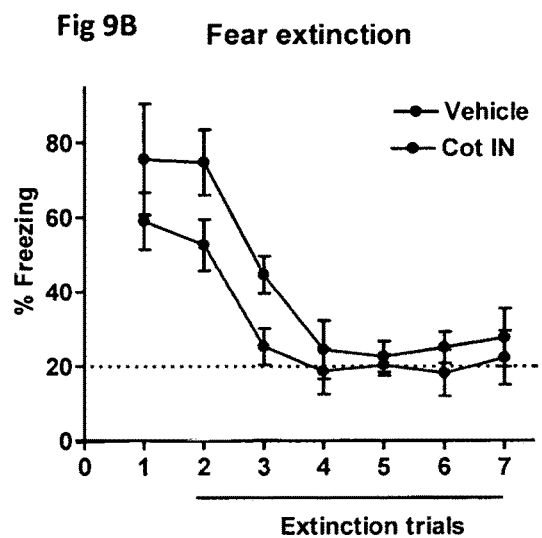
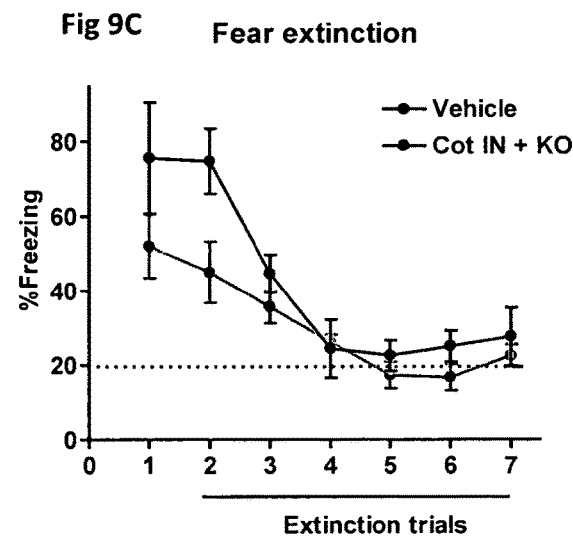

Fig 11A   Open Field
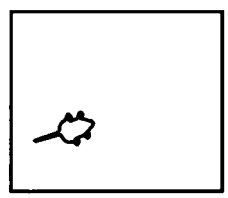 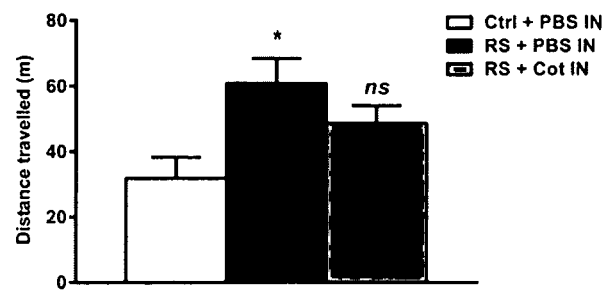
Fig 11B   Forced swim test
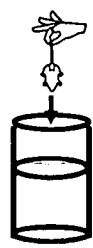 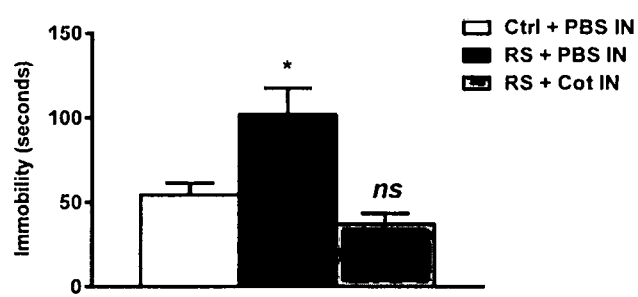

Fig 12A                Novel object recognition
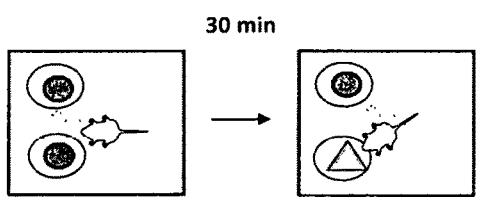
Fig 12B
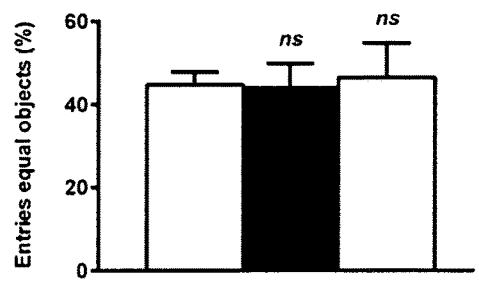
Fig 12C
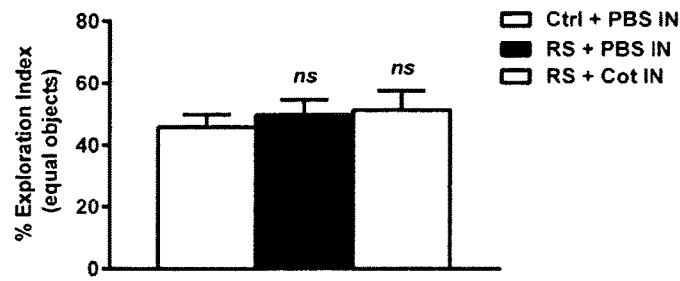
Fig12D
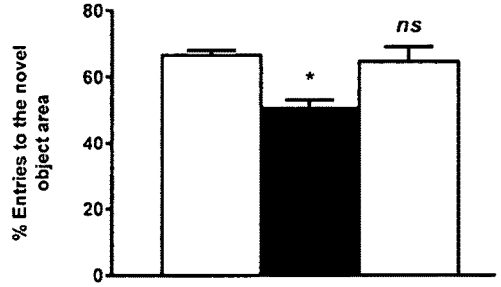
Fig 12E
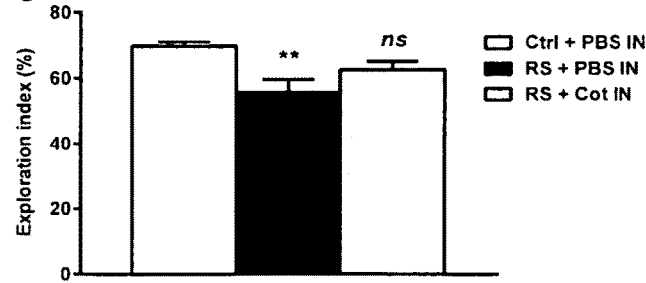

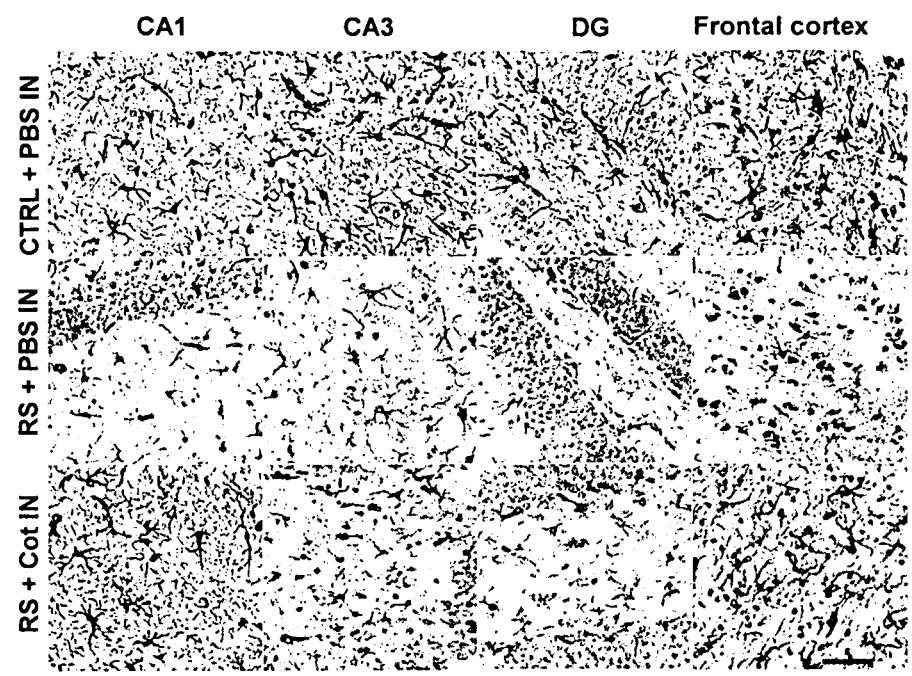
Fig 13A
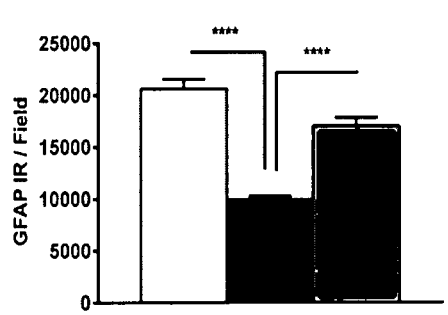
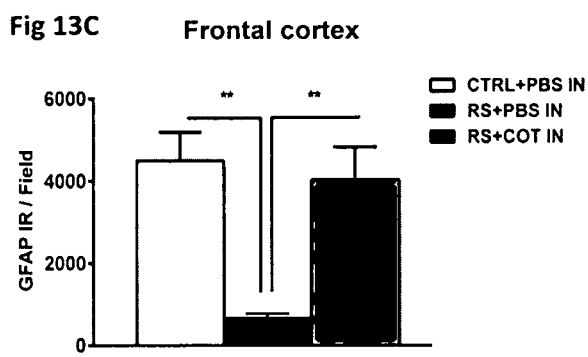

Fig 15A CTRL RS RS+COT
  
Fig 15B
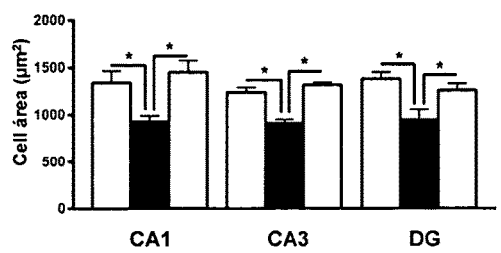
Fig 15C
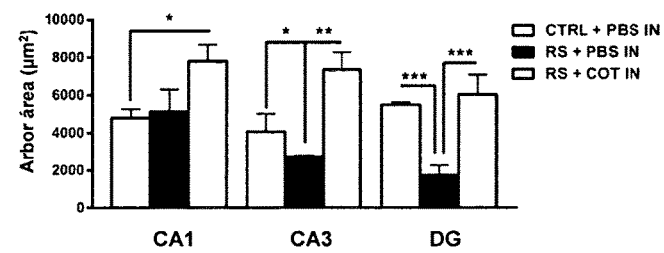
Fig 15D
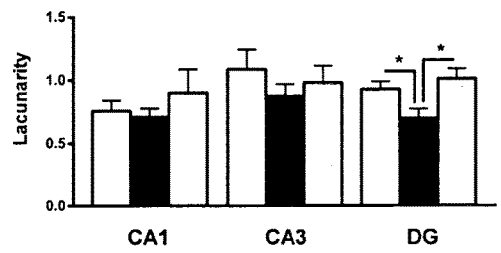
Fig 15E
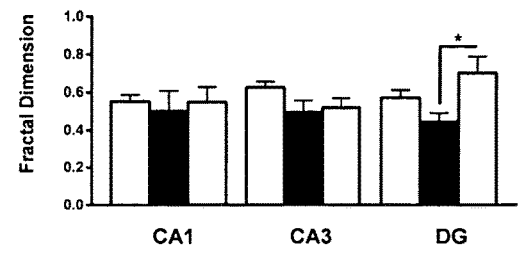

Figure 18 A  Open Field  Figure 18 B1
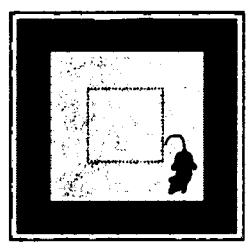
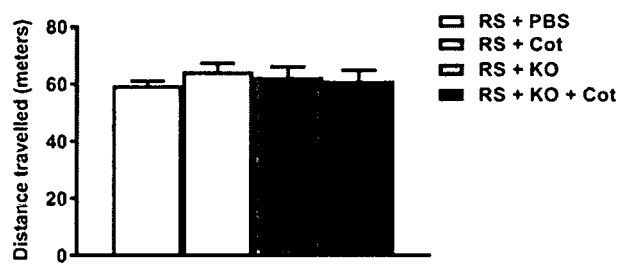
Figure 18 B2
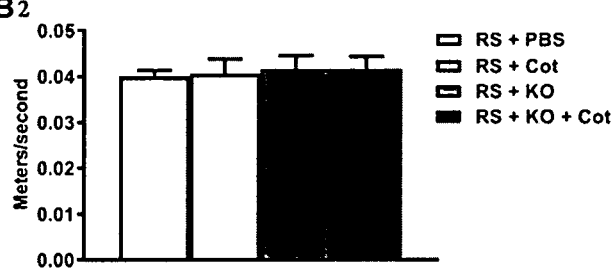

Figure 19 A
Figure 19 B
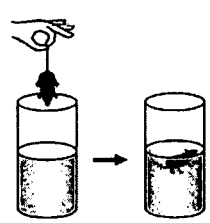
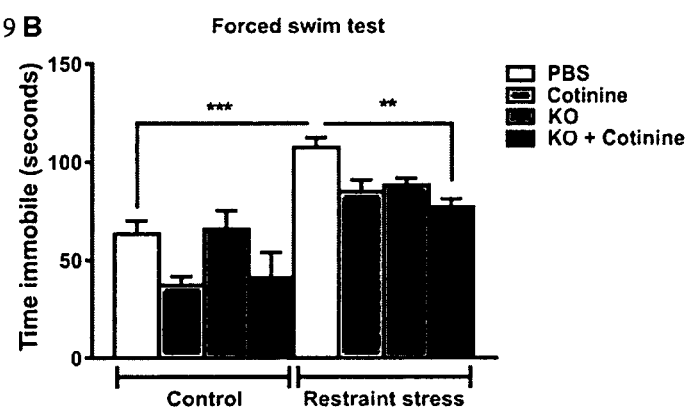

Figure 20 A     Familiarization    Figure 20 B     Novel object recognition
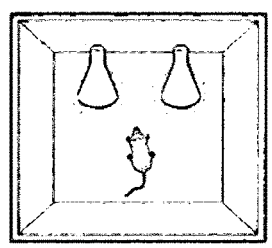
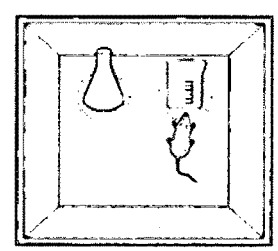
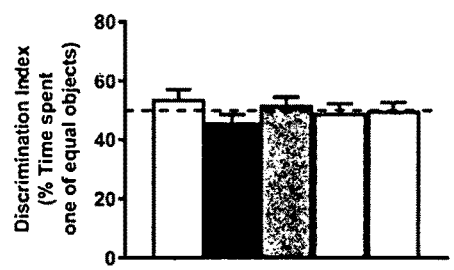
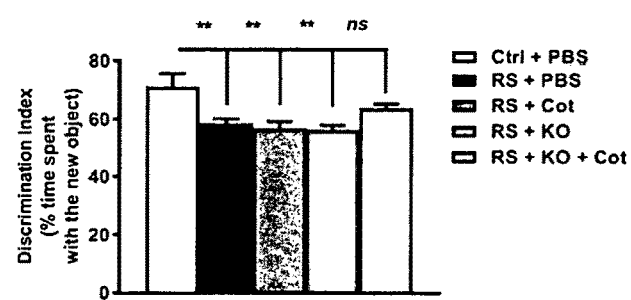

Figure 26A
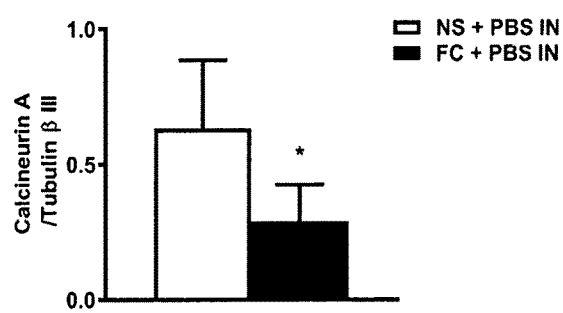
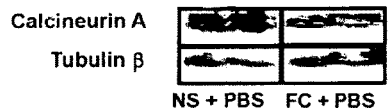
Figure 26B
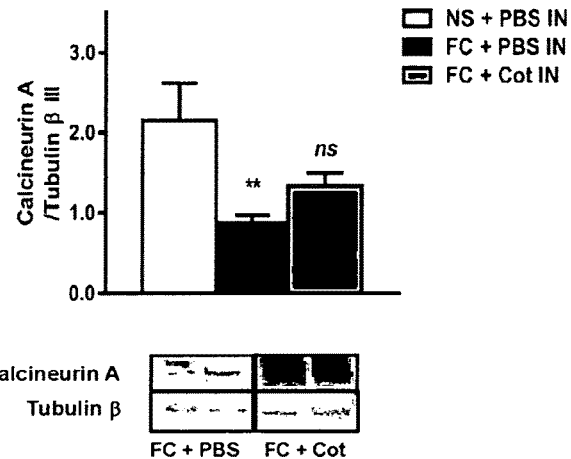
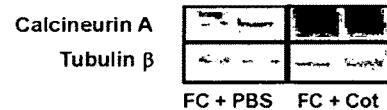

COMBINATION OF COTININE PLUS ANTIOXIDANT FOR TREATMENT-RESISTANT DEPRESSION AND CORRECTION OF ASTROCYTES FUNCTIONAL DEFICIT INDUCED BY DEPRESSION AND OTHER NEUROPATHOLOGICAL

CROSS-REFERENCE TO RELATED APPLICATIONS

This application is a national stage filing under 35 U.S.C. § 371 of International Application No. PCT/IB2018/000306, filed on Feb. 16, 2018, which claims the benefit of U.S. Application No. 62/459,736, filed on Feb. 16, 2017, the contents of which are incorporated herein by reference in their entireties.

All publications, patents, and patent applications mentioned herein are incorporated by reference to the same extent as if each individual publication, patent or patent application was specifically and individually indicated to be incorporated by reference in its entirety.

BACKGROUND

Stress induced by different noxious stimuli occurs when an individual is unable to cope with overwhelming physical or psychological demands. The ability to quickly change behavior and the underlying brain activity in response to threatening stimuli is crucial for survival. While acute stress can be beneficial in recruiting adaptive responses to cope with a stressful situation, prolonged stress can result in maladaptation that can be a risk factor for mental illness and both cognitive and motor deficits that further diminish the quality of life of people with restricted mobility.

Therapies currently in use for stress-induced depression often do not work. The pharmacological approach included anxiolytics, antidepressants and antipsychotics, that have many undesired side effects. Therefore, new drugs or combination of drugs are required.

SUMMARY OF THE INVENTION

The present invention provides methods for treating depression induced by chronic stress in a subject. In one embodiment, the method comprises administering to the subject an effective amount of cotinine or an isomer or racemate thereof, or a pharmaceutically acceptable salt thereof and an antioxidant (or a composition thereof) so as to decrease depression, thereby treating depression induced by chronic stress in the subject. Additionally, provided are pharmaceutical compositions including cotinine or an isomer or racemate thereof, or a pharmaceutically acceptable salt thereof and an antioxidant and kits.

The present invention additionally provides methods for treating anxiety induced by chronic stress in a subject. In an embodiment of the invention, the method comprises administering to the subject an effective amount of cotinine or an isomer or racemate thereof, or a pharmaceutically acceptable salt thereof and an antioxidant (or a composition thereof) so as to decrease anxiety, thereby treating anxiety induced by chronic stress in the subject.

The invention additionally provides a method for treating cognitive impairment induced by chronic stress in a subject which method comprises administering to the subject an effective amount of cotinine or an isomer or racemate thereof, or a pharmaceutically acceptable salt thereof and an antioxidant (or a composition thereof) so as to reverse cognitive impairment, thereby treating cognitive impairment induced by chronic stress in the subject. Merely by way of example, the cognitive impairment may include any of short-term visual recognition memory, short-term recognition memory and/or visual recognition memory.

Also provided are methods for inhibiting or reversing loss of GFAP+ cells in the hippocampus and/or frontal cortex induced by chronic stress in a subject. In one embodiment, the method comprises administering to the subject an effective amount of cotinine or an isomer or racemate thereof, or a pharmaceutically acceptable salt thereof and an antioxidant (or a composition thereof) so as to restore Glial fibrillary acidic protein (GFAP)+ cell number in the hippocampus and/or frontal cortex, thereby inhibiting or reversing loss of GFAP+ cells in the hippocampus and/or frontal cortex induced by chronic stress in the subject.

Further, the invention provides methods for treating altered morphology and/or reduced number of GFAP+ cells in the hippocampus and/or frontal cortex induced by chronic stress in a subject. In one embodiment, the method comprises administering to the subject an effective amount of cotinine or an isomer or racemate thereof, or a pharmaceutically acceptable salt thereof and an antioxidant (or a composition thereof) so as to restore normal morphology of GFAP+ cell in the hippocampus and/or frontal cortex, thereby treating altered morphology and/or reduced number of GFAP+ cells in the hippocampus and/or frontal cortex induced by chronic stress in the subject.

The present invention also provides a method for treating depression in a subject afflicted with post-traumatic stress disorder (PTSD) comprising administering to the subject an effective amount of a composition comprising cotinine or an isomer or racemate thereof, or a pharmaceutically acceptable salt thereof and an antioxidant so as to decrease depression, thereby treating depression in the subject afflicted with post-traumatic stress disorder (PTSD).

The present invention provides a method for treating working memory impairment in a subject afflicted with post-traumatic stress disorder (PTSD) comprising administering to the subject an effective amount of cotinine or an isomer or racemate thereof, or a pharmaceutically acceptable salt thereof and an antioxidant so as to reverse working memory impairment, thereby treating working memory impairment in the subject afflicted with post-traumatic stress disorder (PTSD).

The present invention provides a method for treating anxiety in a subject afflicted with post-traumatic stress disorder (PTSD) comprising administering to the subject an effective amount of cotinine or an isomer or racemate thereof, or a pharmaceutically acceptable salt thereof and an antioxidant so as to decrease anxiety, thereby treating anxiety in the subject afflicted with post-traumatic stress disorder (PTSD).

The present invention provides a method for decreasing consolidation of contextual fear memory in a subject afflicted with post-traumatic stress disorder (PTSD) comprising administering to the subject an effective amount of cotinine or an isomer or racemate thereof, or a pharmaceutically acceptable salt thereof and an antioxidant so as to decrease consolidation of contextual fear memory, thereby decreasing consolidation of contextual fear memory in a subject afflicted with post-traumatic stress disorder (PTSD).

The present invention provides a method for enhancing extinction of fear memory in a subject afflicted with post-traumatic stress disorder (PTSD) comprising administering to the subject an effective amount of cotinine or an isomer or racemate thereof, or a pharmaceutically acceptable salt thereof and an antioxidant so as to enhance extinction of fear memory, thereby enhancing extinction of fear memory in the subject afflicted with post-traumatic stress disorder (PTSD).

The present invention provides a method for increasing calcineurin A expression in a subject afflicted with post-traumatic stress disorder (PTSD) comprising administering to the subject an effective amount of cotinine or an isomer or racemate thereof, or a pharmaceutically acceptable salt thereof and an antioxidant so as to increase calcineurin A expression, thereby increasing calcineurin A expression in the subject afflicted with post-traumatic stress disorder (PTSD).

These and other aspects, objects, features, and advantages of the example embodiments will become apparent to those having ordinary skill in the art upon consideration of the following detailed description of illustrated example embodiments.

BRIEF DESCRIPTION OF THE DRAWINGS

FIG. 1A-C: Cotinine normalized anxiety behavior in mice subjected to restraint stress. A and B, Elevated plus maze; C, Open field test. Cot 0.5, Cotinine 0.5 mg/kg in PBS via oral, Ctrl, Control non-stressed mice; G, Gavage; IN, intranasal; PBS, phosphate buffered saline; RS, restraint stress.

FIG. 9A-C: The Intranasal use of the combination Cotinine plus krill oil was more effective than its components in reducing the consolidation of fear memory in mice subjected to fear conditioning. A, Effect of Cotinine intranasal and Cotinine plus Krill oil on fear memory consolidation; B, Effect of cotinine alone on fear extinction; C, Effect of the mix cotinine plus krill oil on fear extinction. Cot, Cotinine 10 mg/ml; IN, intranasal; KO, Krill oil.

FIG. 11A-B. The effect of intranasal cotinine on locomotor activity and reducing depressive like behavior after chronic restraint stress. Figures to the left represent the behavioral tests used. The graphs depict the effect of restraint stress (RS) and intranasal cotinine (Cot) on locomotor activity in the open field (A), and depressive-like behavior in the forced swim test (B). ns, non-significant change; *, $p<0.05$.

FIG. 12A-E. The effect of intranasal cotinine on visual recognition memory after restraint stress Control (Ctrl) and restrained (RS) mice were treated with intranasal (IN) cotinine 10 mg/ml in PBS (Cot) or vehicle (PBS) for and visual recognition memory were tested in the NOR test. Data is expressed as the percentage of control values and represents the mean±SEM (n=4-5 mice). , $p<0.01$. *, $p<0.001$ FIG. 13A-C. The effect of cotinine on GFAP expression after chronic stress Glial fibrillar acidic protein (GFAP) IR in the frontal cortex (FC) and hippocampus of mice. The images to the right depict the negative control of immunostaining (Ctrl (−)). GFAP IR in control mice treated with intranasal (IN) PBS (CTRL+PBS); mice subjected to restraint stress (RS) and treated with PBS IN and intranasal cotinine (10 mg/ml) (RS+Cot). Each bar represents the average of the percentage of immunostaining for each group field. From left to right the bars represent the mean±standard deviation. Data was analyzed using One-way ANOVA. , $p<0.01$; *, $p<0.001$.

FIG. 15A-E. Analysis of the effect of intranasal cotinine on cerebral neuronal cytoarchitecture in the hippocampus. Figure representing the changes in morphology of GFAP+ cells in the CA1 region of the Hippocampus of mice. Diagrams represent the GFAP+ cells area silhouettes; Graph depicting the changes in cell (B); Arbor area (C); Lacunarity (D), and Fractal dimension (E) in the hippocampus of Control (CTRL) or restrained (RS) mice treated with intranasal (IN) PBS (PBS), or IN cotinine (10 mg/ml)(Cot).

FIG. 18A, B1-B2. Co-treatment with cotinine and krill oil does not affects locomotor activity in mice. After prolonged restraint stress (RS) and co-treatment with vehicle (PBS), cotinine (Cot, 5 mg/kg), krill oil (KO, 143 mg/kg) or (Cot plus KO), mice were tested for locomotor activity in the open field test for 25 min. The results show that treatments did not affect locomotor activity in the mice. A, Total distance traveled. B(1-2), Mean speed (meters/seconds). Ns, non-significant difference (P>0.05). ** significant difference (P<0.01).

FIG. 19A-B. Co-treatment with cotinine plus krill oil prevented the restraint stress-induced depressive-like behavior in mice. Mice were tested for depressive-like behavior: A; Drawing representing the forced swim test; B, after three-week restraint and co-treatment with vehicle (PBS), cotinine (Cot, 5 mg/kg) or krill oil (KO, 143 mg/kg), mice were tested for depressive-like behavior in the forced swim tests (5 min).

FIG. 20A-B. Co-treatment with cotinine decreased the restraint stress-induced deficit in recognition memory. After restraint and co-treatment with vehicle (PBS), cotinine (Cot, 5 mg/kg) krill oil (KO, 143 mg/kg) or Cot plus KO, mice were tested for locomotor activity in the open field test and next day mice were tested for recognition memory in the novel object recognition test (NOR). A, Familiarization: mice were individually exposed to two identical objects. B, Novel object recognition step: after 30 min of rest, mice were exposed to one of the old objects and a new object. Chronic restraint stress impaired novel object recognition. Co-treatment with KO plus Cot preserved recognition memory abilities in the stressed mice to levels non-significantly different from control non-stressed mice (p>0.05).

FIG. 26A-B. Cotinine increased Calcineurin A in the conditioned mice after fear extinction. The hippocampal expression of calcineurin A (CaA) was analyzed by Western blot in the mice after fear conditioning (FC) and extinction (FE). The graphs represent the expression of calcineurin in the hippocampus of control non-exposed to stress (NS) and conditioned (FC) mice treated with PBS (vehicle) (A), and NS conditioned mice treated with PBS, plus cotinine (Cot) (B). ns, non-significant change; *, $p<0.01$. **, $p<0.05$.

DETAILED DESCRIPTION OF THE INVENTION

Definitions

Abbreviations

Figure 2A:
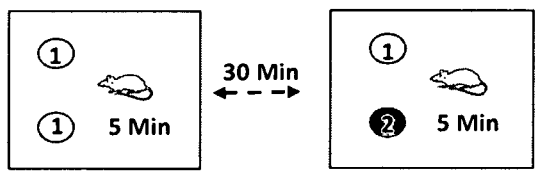
FIG. 2A-D: Cotinine normalized visual working memory in mice subjected to restraint stress. A diagram explaining the novel object recognition test; B and C, Time spent with the equal objects and entries to the equal object 1 area. D, Entries to the novel object area. Cot 0.5, Cotinine 0.5 mg/kg via oral; Ctrl, Control non-stressed mice; G, Gavage; IN, intranasal; PBS, Phosphate buffered saline; RS, restraint stress.
Figure 2B:
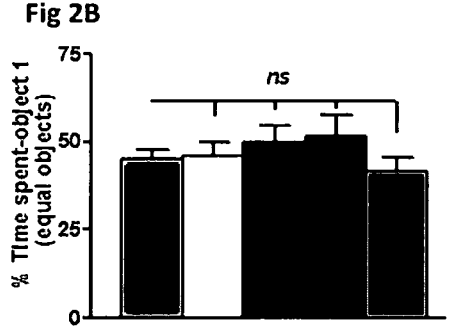
Figure 2C:
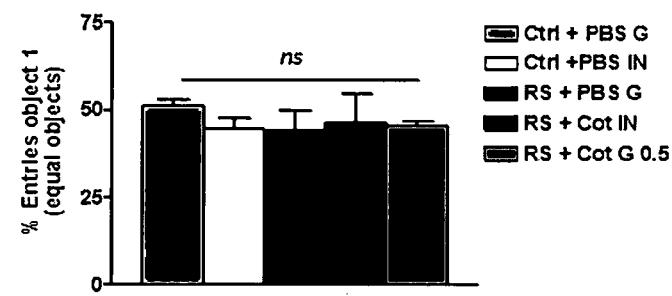

Acetylcholine, ACh; Analysis of variance, ANOVA; Central nervous system (CNS); Conditioned stimulus, CS; Cotinine, Cot; Elevated plus maze, EPM; Frontal cortex, FC; Forced swim, FS; Glial fibrillary acidic protein, GFAP; Intranasal, IN; krill oil, KO; Light-dark box, LDB; Open field, OF; Nicotinic acetylcholine receptors, nAChRs; Novel object recognition, NOR; PAM: positive allosteric Modulator; PNS: Peripheral nervous system; PTSD: Post-traumatic stress disorder; US: Unconditioned stimulus.

(5S)-1-methyl-5-(3-pyridyl) pyrrolidin-2-one (cotinine) includes a composition comprising cotinine, or an isomer or racemate thereof, or a pharmaceutically acceptable salt thereof.

The compositions of the invention can be administered by any parenteral route, e.g., as nasal spray or nebulizer, in the form of a pharmaceutical formulation comprising the active ingredient, optionally in the form of a non-toxic organic, or inorganic, acid, or base, addition salt, in a pharmaceutically acceptable dosage form. Depending upon the disorder and patient to be treated, as well as the route of administration, the compositions may be administered at varying doses.

In human therapy, compositions of the invention may be administered alone but may generally be administered in admixture with a suitable pharmaceutical excipient diluent or carrier selected with regard to the intended route of administration and standard pharmaceutical practice.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials. Extemporaneous injection solutions and suspensions may be prepared from sterile powders, granules and tablets of the kind previously described.

The terms "pharmaceutical formulations", "pharmaceutical compositions" and "dosage forms" are used interchangeably herein and refer to a composition containing the active ingredient(s) of the invention in a form suitable for administration to a subject.

The term "effective amount" means an amount of a compound or composition according to the present invention effective in producing the desired therapeutic effect.

The phrase "pharmaceutically acceptable" is employed herein to refer to those compounds, materials, compositions; and/or dosage forms which are, within the scope of sound medical judgment, suitable for use in contact with the tissues of human beings and animals without excessive toxicity, irritation, allergic response, or other problem or complication commensurate with a reasonable benefit/risk ratio.

The term "about" when used in connection with percentages means±1-5%.

The term "desirable therapeutic effect" means to treat a subject with the active agents of the invention in order to prevent or ameliorate a disease and/or disease condition.

Diagnosis of various mental and psychological disorders, including depression and post-traumatic stress disorder (PTSD), may be found, e.g., in the *Diagnostic and Statistical Manual of Mental Disorders* (5th ed.; DSM-5; American Psychiatric Association, 2013).

In accordance with the practice of the invention, the subject may be a mammal. In other embodiments of the invention, the subject may be any of human, monkey, ape, dog, cat, cow, horse, sheep, rabbit, mouse, or rat.

The present invention provides methods for treating depression induced by chronic stress in a subject. In one embodiment, the method comprises administering to the subject an effective amount of a combination of cotinine or an isomer or racemate thereof, or a pharmaceutically acceptable salt thereof and an antioxidant (or a composition thereof) so as to decrease depression, thereby treating depression induced by chronic stress in the subject. In accordance with the practice of the invention, the antioxidant may reduce or prevent oxidative stress or deleterious effect of stress on brain function. Examples of antioxidants include, but are not limited to, vitamins A, C and E; polyphenols, astaxantina; omega-3 polyunsaturated fatty acids (n-3 PUFAs); B vitamins; monounsaturated fatty acids; vitamin D; and minerals including iodine, magnesium, zinc, selenium, potassium and iron. Examples of depression includes, but are not limited to, long-lasting depression, major depressive disorder (MDD) and stress-induced treatment resistant depression.

In an embodiment of the invention, the antioxidant may be or may include Krill oil (KO). KO may be extracted from the Antarctic microcrustacean *Euphausia superba* and is a rich source of phospholipids, ASTA and (n-3)/PUFAs, including EPA and DHA. For example, the krill oil may comprise an omega-3 fatty acid, phospholipid, and/or astaxanthin. In one embodiment, the omega-3 fatty acid is or comprises an omega-3 polyunsaturated fatty acid (PUFA). In an additional embodiment, the omega-3 polyunsaturated fatty acid (PUFA) includes, but is not limited to, an eicosapentanoic acid (EPA), or docosahexaenoic acid (DHA) and/or a combination thereof. In one embodiment, the phospholipid forms a liposome. In some embodiments, the antioxidant reduces or prevents oxidative stress or deleterious effect of stress on brain function.

In some embodiments of the invention, the active agents of the invention (cotinine or an isomer or racemate thereof, or a pharmaceutically acceptable salt thereof and the antioxidant) may be administered together or in combination with other therapeutic agents. In accordance with the practices of the invention, cotinine can be administered free of nicotine. Components of the combinations may be administered either concomitantly, (e.g., as an admixture), separately but simultaneously or concurrently or sequentially. This includes presentations in which the combined active agents are administered together as a therapeutic mixture, and also procedures in which the combined active agents are administered separately but simultaneously, e.g., as through separate intravenous lines into the same individual or through separate nostrils of the same individual. Administration "in combination" further includes the separate administration of one of the active agents given first, followed by the one or more sequential active agent(s).

The present invention additionally provides methods for treating anxiety induced by chronic stress in a subject. In an embodiment of the invention, the method comprises administering to the subject an effective amount of a combination of cotinine or an isomer or racemate thereof, or a pharmaceutically acceptable salt thereof and an antioxidant (or a composition thereof) so as to decrease anxiety, thereby treating anxiety induced by chronic stress in the subject. Merely by way of example, chronic stress may be chronic restraint stress or chronic immobilization stress.

Additional examples of chronic restraint stress or chronic immobilization stress include, but are not limited to, acute pain, age-related immobility, anti-psychotic-induced rigidity, arthritis, ataxia, Bursa pain, cardiovascular disease, cerebellar dysfunction, chronic pain, deconditioning after prolonged bed rest, diabetes, disuse, electrolyte abnormality, fear of falling, fear of instability, femur fracture, foot pain, forced immobility, frequent angina, frequent claudication, hip fracture, involuntary restraint, joint pain, malnutrition, metastases, muscle pain, muscular atrophy, musculoskeletal disorder, myopathy, neurodegenerative condition, neurologic disease, neurological disorder, obesity, orthostatic hypotension, osteoarthritis, osteoporosis, Paget's disease, paralysis, Parkinson's disease, peripheral or central neuropathy, podiatric problem, polymyalgia, pulmonary disease, severe chronic obstructive lung disease, severe congestive heart failure, severe systemic illness, spinal cord injury, stroke, traumatic brain injury, vertebral fracture and visual impairment.

The invention further provides a method for treating cognitive impairment induced by chronic stress in a subject which method comprises administering to the subject an effective amount of a combination of cotinine or an isomer or racemate thereof, or a pharmaceutically acceptable salt thereof and an antioxidant (or a composition thereof) so as to reverse cognitive impairment, thereby treating cognitive impairment induced by chronic stress in the subject. In one embodiment, the cognitive dysfunction is selected from the group consisting of short-term memory deficit and attention deficit.

Additionally, the invention provides methods for inhibiting or reversing loss of GFAP+ cells in the hippocampus and/or frontal cortex induced by chronic stress in a subject. For example, chronic stress may induce a statistically significant decrease of GFAP+ cell lacunarity of dentate gyrus of the hippocampus in a chronic stress subject. In one embodiment of the invention, the method comprises administering to the subject an effective amount of a combination of cotinine or an isomer or racemate thereof, or a pharmaceutically acceptable salt thereof and an antioxidant (or a composition thereof) so as to restore Glial fibrillary acidic protein (GFAP)+cell number in the hippocampus and/or frontal cortex, thereby inhibiting or reversing loss of GFAP+ cells in the hippocampus and/or frontal cortex induced by chronic stress in the subject. In one embodiment, the GFAP+ cell may be or may comprise an astrocyte. For example, the hippocampus may comprise region CA1, CA3 and/or dentate gyrus or portions thereof. GFAP is a family of proteins that includes 8 isoforms expressed by different subpopulations of astrocytes in the human and rodent brain. These isoforms include GFAP+1, GFAP delta and GFAP kappa.

In one embodiment of the invention, restoring GFAP+ cell number in the hippocampus and/or frontal cortex may comprise restoration of GFAP+ immunoreactivity to greater than 80% of pre-chronic stress in the subject. In another embodiment, restoring GFAP+ cell number in the hippocampus and/or frontal cortex may comprise restoration of GFAP+ cell density in the hippocampus and/or frontal cortex.

In another embodiment of the invention, an altered morphology and/or reduced number of GFAP+ cells in the hippocampus and/or frontal cortex includes having small cells with short, tiny and poorly ramified processes. In a further embodiment, restoring normal morphology of GFAP+ cell in the hippocampus and/or frontal cortex includes having large cells with longer and complex arborization.

In an additional embodiment, treatment with cotinine or an isomer or racemate thereof, or a pharmaceutically acceptable salt thereof and an antioxidant or a composition containing them results in a statistically significant increase of GFAP+ cell area in chronic stress and composition treated subject which is indistinguishable from control subject, not exposed to chronic stress and not treated with the composition. For example, in some embodiments, the treatment with cotinine or an isomer or racemate thereof, or a pharmaceutically acceptable salt thereof and an antioxidant or a composition containing them may increase arborization area of GFAP+ cells in a hippocampal region dependent manner. In further embodiment, treatment with the composition results in a statistically significant increase of GFAP+ cell lacunarity of dentate gyrus of the hippocampus in chronic stress and composition treated subject.

In another further embodiment, chronic stress induces a statistically significant decrease of GFAP+ cell fractal dimension of dentate gyrus of the hippocampus in chronic stress subject. In an additional embodiment, the treatment with the composition results in a statistically significant increase of GFAP+ cell fractal dimension of dentate gyrus of the hippocampus in chronic stress and composition treated subject.

In yet a further embodiment, the administration of a combination of cotinine or an isomer or racemate thereof, or a pharmaceutically acceptable salt thereof and an antioxidant or a composition including them restores or prevents loss of astrocytes. Additionally, in one embodiment, the administration of cotinine or an isomer or racemate thereof, or a pharmaceutically acceptable salt thereof and an antioxidant or a composition including them may increase the astrocyte number. In a further embodiment, the administration of cotinine or an isomer or racemate thereof, or a pharmaceutically acceptable salt thereof and an antioxidant or a composition including them may restore or prevent loss of astrocyte arbor complexity.

Also, the invention provides methods for treating altered morphology and/or reduced number of GFAP+ cells in the hippocampus and/or frontal cortex induced by chronic stress in a subject. In one embodiment, the method comprises administering to the subject an effective amount of a combination of cotinine or an isomer or racemate thereof, or a pharmaceutically acceptable salt thereof and an antioxidant (or a composition thereof) so as to restore normal morphology of GFAP+ cell in the hippocampus and/or frontal cortex, thereby treating altered morphology and/or reduced number of GFAP+ cells in the hippocampus and/or frontal cortex induced by chronic stress in the subject.

In an additional embodiment, the administration of cotinine or an isomer or racemate thereof, or a pharmaceutically acceptable salt thereof and an antioxidant (also referred to herein as active ingredients or combination of active ingredients) or a composition including them may inhibit microgliosis, inhibit neuroinflammation, inhibit hippocampal volume reduction, restore hippocampal volume, promote neuronal survival, or astrocyte survival or a combination thereof.

Further, examples of conditions affecting the expression of GFAP+ cells in the brain of the subject includes, but are not limited to, Wernicke's encephalopathy, viral infectious disease of nervous system, Down's syndrome, Alzheimer's disease, anxiety and treatment-resistant depression. Examples of viral infectious diseases include HIV-1, varicella zoster virus and pseudorabies.

The present invention provides a method for treating depression in a subject afflicted with post-traumatic stress disorder (PTSD) comprising administering to the subject an effective amount of a combination of cotinine or an isomer or racemate thereof, or a pharmaceutically acceptable salt thereof and an antioxidant (or a composition thereof) so as to decrease depression, thereby treating depression in the subject afflicted with post-traumatic stress disorder (PTSD). The present invention provides a, method for treating working memory impairment in a subject afflicted with post-traumatic stress disorder (PTSD) comprising administering to the subject an effective amount of cotinine or an isomer or racemate thereof, or a pharmaceutically acceptable salt thereof and an antioxidant (or a composition thereof) so as to reverse working memory impairment, thereby treating working memory impairment in the subject afflicted with post-traumatic stress disorder (PTSD).

The present invention additionally provides a method for treating anxiety in a subject afflicted with post-traumatic stress disorder (PTSD) comprising administering to the subject an effective amount of a combination of cotinine or an isomer or racemate thereof, or a pharmaceutically acceptable salt thereof and an antioxidant (or a composition thereof) so as to decrease anxiety, thereby treating anxiety in the subject afflicted with PTSD.

The present invention also provides a method for decreasing consolidation of contextual fear memory in a subject afflicted with PTSD comprising administering to the subject an effective amount of a combination of cotinine or an isomer or racemate thereof, or a pharmaceutically acceptable salt thereof and an antioxidant (or a composition thereof) so as to decrease consolidation of contextual fear memory, thereby decreasing consolidation of contextual fear memory in a subject that suffered a traumatic experience afflicted or not with PTSD.

The present invention further provides a method for enhancing extinction of fear memory in a subject afflicted or not with PTSD comprising administering to the subject an effective amount of a combination of cotinine or an isomer or racemate thereof, or a pharmaceutically acceptable salt thereof and an antioxidant (or a composition thereof) so as to enhance extinction of fear memory, thereby enhancing extinction of fear memory in the subject afflicted or not with PTSD.

The present invention provides a method for increasing calcineurin A expression in a subject afflicted with PTSD comprising administering to the subject an effective amount of cotinine or an isomer or racemate thereof, or a pharmaceutically acceptable salt thereof and an antioxidant (or a composition thereof) so as to increase calcineurin A expression, thereby increasing calcineurin A expression in the subject afflicted with post-traumatic stress disorder (PTSD).

In accordance with the practice of the invention, administration of cotinine or an isomer or racemate thereof, or a pharmaceutically acceptable salt thereof and an antioxidant or compositions containing them may be oral, intravenous, intramuscular, intrathecal, subcutaneous, sublingual, buccal, rectal, vaginal, ocular, via otical route, nasal, intranasal, via inhalation, via nebulization, cutaneous, or transdermal administration or a combination thereof. In a specific embodiment, cotinine and an antioxidant or a composition containing them may be administered orally. In a preferred embodiment, cotinine and an antioxidant or a composition containing them may be administered intranasally.

In a specific embodiment of the invention, ccotinine or an isomer or racemate thereof, or a pharmaceutically acceptable salt thereof and an antioxidant or compositions containing them may be formulated for delivery via nasal, intranasal, intramuscular, subcutaneous, transdermal or sublingual administration. For example, the nasal or intranasal administration may bypass the blood-brain barrier, and/or avoid or may be free of gastrointestinal and hepatic first-pass metabolism. In one embodiment, nasal or intranasal administration provides fast-onset of action and rapid delivery to brain of the subject. In another embodiment, nasal or intranasal administration permits treatment of emergency mental situation. In a further embodiment, the active agent (also referred to herein as active ingredient) or pharmaceutical composition containing them is administered intranasally and is absorbed by nasal tissue located at the rear of the nasal cavity in the vicinity of the fossa of Rosenmuller, nasopharynx, tonsillar tissues, or the Waldeyer's tonsillar ring. In a further embodiment, said active ingredients or pharmaceutical composition containing them is delivered by nebulization or spraying.

In a further embodiment, the composition or the combination of the active ingredients is administered following chronic stress in the subject. In another further embodiment the composition or the combination of the active ingredients is administered while under or during chronic stress in the subject. In an additional embodiment, the composition or the combination of the active ingredients is administered at least twice daily. In one embodiment, the composition or the combination of the active ingredients is administered at least once a day, once a week or once a month.

In another embodiment, administering an effective amount of cotinine and an antioxidant or composition containing them additionally increases calcineurin A expression in the hippocampus and/or frontal cortex. In a further embodiment, administering an effective amount of a composition or the combination of the active ingredients comprising cotinine and an antioxidant additionally inhibits hippocampal volume reduction and/or restores hippocampal volume.

Administration of the antioxidant may be simultaneous as the administration of the cotinine or an isomer or racemate thereof, or a pharmaceutically acceptable salt thereof. In another embodiment, the administration of the antioxidant is not simultaneous as the administration of the cotinine or an isomer or racemate thereof, or a pharmaceutically acceptable salt thereof. In a further embodiment, the administration of the antioxidant occurs before or after the administration of the cotinine or an isomer or racemate thereof, or a pharmaceutically acceptable salt thereof. In another further embodiment, the administration of the antioxidant is by a same route as the route of administration of the cotinine or an isomer or racemate thereof, or a pharmaceutically acceptable salt thereof. In another embodiment, the administration of the antioxidant is by a different route than the route of administration of the cotinine or an isomer or racemate thereof, or a pharmaceutically acceptable salt thereof. In another embodiment, the administration of the cotinine or an isomer or racemate thereof, or the pharmaceutically acceptable salt thereof and the antioxidant is intranasal and simultaneous. In another further embodiment, the composition or the combination of the active ingredients is administered following a diagnosis of PTSD in the subject.

In an additional embodiment, administering a therapeutically effective amount of the cotinine or the isomer or racemate thereof, or the pharmaceutically acceptable salt thereof and the antioxidant, or the composition thereof additionally increases or restores capability to use contextual information to restrain fear expression. In one embodiment, administering an effective amount of a composition comprising cotinine and an antioxidant additionally treats contextual fear memory dysfunction.

The present invention provides a method of treating a patient suffering from pathological conditions derived of immobilization stress, obesity, paralysis, stroke, cerebral ischemia, traumatic spinal injury, traumatic brain injury, arthrosis, treatment-resistant depression, anxiety and/or cognitive dysfunction comprising administering to the patient a therapeutically effective amount of a combination of cotinine or an isomer or racemate thereof, or a pharmaceutically acceptable salt thereof and an antioxidant or a pharmaceutical composition of the invention to treat the patient.

The present invention provides a method of treating of treating a human patient suffering from depression, stress-related disorders and other neuropathological conditions, comprising providing for such a patient a therapeutically effective amount of a combination of cotinine or an isomer or racemate thereof, or a pharmaceutically acceptable salt thereof and an antioxidant or a pharmaceutical composition of the invention to a human in need of such treatment.

In one embodiment of the invention, the therapeutically effective amount of cotinine for intranasal administration is about 1 mg/ml to 100 mg/ml. In another embodiment, the therapeutically effective amount of cotinine is about 0.5 to 100 mg/ml at a concentration of 1-30% antioxidant. In a further embodiment, the therapeutically effective amount of krill oil is about 5 to 500 mg/ml. In another embodiment, the therapeutically effective amount of cotinine is about 0.5 to 100 mg/ml and antioxidant is about 5 to 500 mg/ml, wherein the antioxidant is krill oil.

In accordance with the practice of the invention, the drug can be administered one or more times a day, daily, weekly, monthly or yearly.

Dosage of the therapeutic agent(s) of the invention may be dependent upon many factors including, but not limited to, the type of tissue affected, the type of disease being treated, the severity of the disease, a subject's health and response to the treatment with the agents. Accordingly, dosages of the agents can vary depending on each subject and the mode or route of administration. Merely by way of example, the therapeutically effective amount of (5S)-1-methyl-5-(3-pyridyl) pyrrolidin-2-one (cotinine) is about 0.1 mg/kg to about 10 mg/kg. In a further embodiment, the therapeutically effective amount of (5S)-1-methyl-5-(3-pyridyl) pyrrolidin-2-one (cotinine) is about 0.5 mg/kg, or 5 mg/kg. In one embodiment, the therapeutically effective amount of cotinine may be about 5-10 time lower normalized by body weight in a human subject than in a mouse. In one embodiment, the therapeutically effective amount of cotinine may be about 0.1-2 mg/kg weight for intramuscular injection in a human subject. In a preferred embodiment for intramuscular route of administration, the therapeutically effective amount of cotinine may be about 2 mg/kg weight in a human subject.

In one embodiment, dosage of the therapeutic agent(s) of the invention may be twice a day in both nostrils at about 0.25-0.5 ml per nostril with 25-50 mg/ml cotinine in PBS with about 30-50% krill oil or equivalent. In one embodiment, the equivalent dose of krill oil may be based on omega-3 content. In another embodiment, the therapeutically effective amount of (5S)-1-methyl-5-(3-pyridyl) pyrrolidin-2-one (cotinine) may be about 0.5-2.5 mg/kg weight for oral administration of cotinine in a human subject. In another embodiment, the therapeutically effective amount of krill oil may be about 5-10 mg/kg weight for oral administration of krill oil in a human subject. In another embodiment, the therapeutically effective amount of (5S)-1-methyl-5-(3-pyridyl) pyrrolidin-2-one (cotinine) may be about 1-5 mg/kg weight and the therapeutically effective amount of krill oil may be about 5-10 mg/kg weight for oral administration of krill oil in a human subject.

In another embodiment, the therapeutically effective amount of (5S)-1-methyl-5-(3-pyridyl) pyrrolidin-2-one (cotinine) may be about 100-200 mg/day for intranasal administration of cotinine in a human subject. A dose 10-50 mg/day can be used using nanoparticles to facilitate the efficiency of the delivery of cotinine to the brain. In another embodiment, the therapeutically effective amount of krill oil may be about 30-50% of cotinine solution for intranasal administration of krill oil in a human subject. In another embodiment, the therapeutically effective amount of (5S)-1-methyl-5-(3-pyridyl) pyrrolidin-2-one (cotinine) may be about 100-200 mg/day and the therapeutically effective amount of krill oil may be about 30-50% of cotinine solution for intranasal administration of krill oil in a human subject.

Compositions

The invention provides compositions (including pharmaceutical compositions) comprising a combination of cotinine or an isomer or racemate thereof, or a pharmaceutically acceptable salt thereof and an antioxidant for use, e.g., in the methods of the invention.

In accordance with the practice of the invention, the administration of a given drug may be effected locally or systemically. Additionally, the route of administration of a given drug may be any of topical, enteral or parenteral. In other embodiments of the invention, the route of administration of a given drug may be any of nasal, rectal, intercisternal, buccal, intramuscular, intrasternal, intracutaneous, intrasynovial, intravenous, intraperitoneal, intraocular, periosteal, intra-articular injection, infusion, oral, inhalation, subcutaneous, implantable pump, continuous infusion, gene therapy, intranasal, intrathecal, intracerebroventricular, transdermal, or by spray, patch or injection.

In accordance with the practice of the invention, the route of administration of a given drug can vary during a course of treatment, or during a given day. For example, if a given drug is administered in conjunction with one or more additional drugs, each additional drug may be administered by identical or different routes compared to the other drugs.

In accordance with the practice of the invention, the drug can be administered one or more times a day, daily, weekly, monthly or yearly.

The present invention provides pharmaceutical formulations (also known as pharmaceutical compositions or dosage forms) comprising a first active agent (e.g., cotinine), one or more additional active agent (e.g., krill oil, a ligand of nicotinic receptor, a positive allosteric modulator or other active agent), and a pharmaceutically acceptable carrier or vehicle.

Pharmaceutically acceptable carrier or vehicle refers to a non-toxic solid, semisolid (also referred to herein as softgel) or liquid filler, diluent, encapsulating material or formulation auxiliary of any type. The invention also provides methods for treating or ameliorating cotinine modulated diseases using said pharmaceutical formulations.

The present invention provides a pharmaceutical composition comprising cotinine and an antioxidant. In one embodiment, the pharmaceutical composition further comprises one or more pharmaceutically acceptable carriers. In another embodiment, the pharmaceutical composition is in a solution which is at a pH 6 to 8. In a further embodiment, the composition is formulated so that the route of administration may be any of an enteral, parenteral, dermal, ocular, nasal, intranasal, otic, rectal, vaginal, urethral, buccal or pharyngotracheobronchial route. In a preferred embodiment, the composition is formulated for intranasal administration. In a specific embodiment, the composition is formulated for oral administration. In one embodiment of the composition, the antioxidant contained therein is a krill oil. For example, the krill oil may be derived from a species of Antarctic krill. In a further example, the species of Antarctic krill is *Euphausia superba*. By way of example, the krill oil may comprise a ratio of about 90 mg omega-3 fatty acids to 300 mg krill oil. In an additional embodiment, the krill oil comprises a ratio of about 50 mg eicosapentanoic acid (EPA) omega-3 fatty acids to 300 mg krill oil. In one embodiment, the krill oil comprises a ratio of about 24 mg docosahexaenoic acid (DHA) omega-3 fatty acids to 300 mg krill oil. In another embodiment, the krill oil comprises a ratio of about 50 mg eicosapentanoic acid (EPA) omega-3 fatty acids to 24 mg docosahexaenoic acid (DHA) omega-3 fatty acids. In a further embodiment, the krill oil comprises a ratio of about 130 mg phospholipids to 300 mg krill oil. In another further embodiment, the krill oil comprises astaxanthin. In another embodiment, the krill oil comprises astaxanthin, wherein astaxanthin is an antioxidant.

Dosage Forms

Dosage forms can be made according to well-known methods in the art. Some preferred methods are described below.

The pharmaceutical compositions of the invention may be formulated as solid dosage forms, such as capsules, pills, softgels, tablets, caplets, troches, wafer, sprinkle, chewing gum or the like, for oral administration. The pharmaceutical compositions of the invention may also be formulated as liquid dosage forms such as elixir, suspension or syrup.

The pharmaceutical compositions of the invention may also be presented in a dosage form for transdermal application, for example an ointment for children, a form for oral administration, for example a slow release product, or in gastro-resistant tablet form or gum form. They may also be in spray, bronchial form or eye lotion form, or other galenic forms with programmed mucosal and secondarily per os disintegration.

The pharmaceutical compositions of the invention or the active ingredients of the invention may be in a liquid dosage form or a suspension to be applied to nasal cavity or oral cavity using a dropper, a sprayer or a container. The pharmaceutical compositions of the invention or the active ingredients of the invention may be in a solid, salt or powder to be applied to nasal cavity or oral cavity using a sprayer, a forced air or a container.

Therefore, the different pharmaceutical compositions of the invention can be administered by several routes chosen in accordance with the patient's pathological profile and age. For children, the patch form, syrup form or tablets to be dissolved in the mouth. The other forms, eye lotion or injection may also be used. In adults all galenic forms (also known as dosage forms) can be contemplated.

The advantage of a coupled or combined galenic form also provides simplicity of treatment, patient compliance with the simplified treatment and therefore a more successful outcome.

The pharmaceutical compositions of the present invention may be mixed with pharmaceutically acceptable carriers, binders, diluents, adjuvants, excipients, or vehicles, such as preserving agents, fillers, polymers, disintegrating agents, glidants, wetting agents, emulsifying agents, suspending agents, sweetening agents, flavoring agents, perfuming agents, lubricating agents, acidifying agents, coloring agent, dyes, preservatives and dispensing agents, or compounds of a similar nature depending on the nature of the mode of administration and dosage forms. Such ingredients, including pharmaceutically acceptable carriers and excipients that may be used to formulate oral dosage forms, are described in the Handbook of Pharmaceutical Excipients, American Pharmaceutical Association (1986), incorporated herein by reference in its entirety.

Pharmaceutically acceptable carriers are generally non-toxic to recipients at the dosages and concentrations employed and are compatible with other ingredients of the formulation. Examples of pharmaceutically acceptable carriers include water, saline, Ringer's solution, dextrose solution, ethanol, polyols, vegetable oils, fats, ethyl oleate, liposomes, waxes polymers, including gel forming and non-gel forming polymers, and suitable mixtures thereof. The carrier may contain minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulin; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium; and/or nonionic surfactants such as polysorbates, poloxamers, or PEG. Preferably the carrier is a parenteral carrier, more preferably a solution that is isotonic with the blood of the recipient.

Examples of binders include, but are not limited to, microcrystalline cellulose and cellulose derivatives, gum tragacanth, glucose solution, acacia mucilage, gelatin solution, molasses, polyvinylpyrrolidone, povidone, crospovidone, sucrose and starch paste.

Examples of diluents include, but are not limited to, lactose, sucrose, starch, kaolin, salt, mannitol and dicalcium phosphate.

Examples of excipients include, but are not limited to, starch, surfactants, lipophilic vehicles, hydrophobic vehicles, pregelatinized starch, Avicel, lactose, milk sugar, sodium citrate, calcium carbonate, dicalcium phosphate, and lake blend purple. Typical excipients for dosage forms such as a softgel include gelatin for the capsule and oils such as soy oil, rice bran oil, canola oil, olive oil, corn oil, and other similar oils; glycerol, polyethylene glycol liquids, vitamin E TPGS as a surfactant and absorption enhancer (Softgels: Manufacturing Considerations; Wilkinson P, Foo Sog Horn, Special Drug Delivery Systems; Drugs and the Pharmaceutical Sciences Vol 41 Praveen Tyle Editor, Marcel Dekker 1990, 409-449; Pharmaceutical Dosage Forms and Drug Delivery by Ansel, Popovich and Allen 1995, Williams and Wilkins, Chapter 5 pp 155-225).

Examples of disintegrating agents include, but are not limited to, complex silicates, croscarmellose sodium, sodium starch glycolate, alginic acid, corn starch, potato starch, bentonite, methylcellulose, agar and carboxymethylcellulose.

Examples of glidants include, but are not limited to, colloidal silicon dioxide, talc, corn starch.

Examples of wetting agents include, but are not limited to, propylene glycol monostearate, sorbitan monooleate, diethylene glycol monolaurate and polyoxyethylene laural ether.

Examples of sweetening agents include, but are not limited to, sucrose, lactose, mannitol and artificial sweetening agents such as saccharin, and any number of spray dried flavors.

Examples of flavoring agents include, but are not limited to, natural flavors extracted from plants such as fruits and synthetic blends of compounds which produce a pleasant sensation, such as, but not limited to peppermint and methyl salicylate.

Examples of lubricants include magnesium or calcium stearate, sodium lauryl sulphate, talc, starch, lycopodium and stearic acid as well as high molecular weight polyethylene glycols.

Examples of coloring agents include, but are not limited to, any of the approved certified water soluble FD and C dyes, mixtures thereof; and water insoluble FD and C dyes suspended on alumina hydrate.

The artisan of ordinary skill in the art will recognize that many different ingredients can be used in formulations according to the present invention, in addition to the active ingredients, while maintaining effectiveness of the formulations in a) treating any of depression induced by chronic stress; depression in a subject afflicted with PTSD; anxiety induced by chronic stress; anxiety in a subject afflicted with PTSD; cognitive impairment induced by chronic stress; altered morphology and/or reduced number of GFAP+ cells in the hippocampus and/or frontal cortex induced by chronic stress; working memory impairment in a subject afflicted with PTSD; b) inhibiting or reversing loss of GFAP+ cells in the hippocampus and/or frontal cortex induced by chronic stress; c) decreasing consolidation of contextual fear memory in a subject afflicted with PTSD; d) enhancing extinction of fear memory in a subject afflicted with PTSD; or increasing calcineurin A expression in a subject afflicted with PTSD. The list provided herein is not exhaustive.

Kits

The invention also provides a pharmaceutical pack or kit comprising one or more containers filled with one or more of the active ingredients of the compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

For example, the present invention provides kits comprising cotinine, an antioxidant and an instruction for use. In one embodiment, the kit, additionally comprises a dispenser for administration of cotinine and an antioxidant. Merely by way of example, the dispenser may be for nasal administration.

The kit may contain a pharmaceutical composition that includes one or more active agents of the invention effective for a) treating any of depression induced by chronic stress; depression in a subject afflicted with PTSD; anxiety induced by chronic stress; anxiety in a subject afflicted with PTSD; cognitive impairment induced by chronic stress; altered morphology and/or reduced number of GFAP+ cells in the hippocampus and/or frontal cortex induced by chronic stress; working memory impairment in a subject afflicted with PTSD; b) inhibiting or reversing loss of GFAP+ cells in the hippocampus and/or frontal cortex induced by chronic stress; c) decreasing consolidation of contextual fear memory in a subject afflicted with PTSD; d) enhancing extinction of fear memory in a subject afflicted with PTSD; or increasing calcineurin A expression in a subject afflicted with PTSD. It may further include other materials desirable from a commercial and user standpoint, including other buffers, diluents, filters, needles, syringes, and package inserts with instructions for use.

The agents may be provided as dry powders, usually lyophilized, including excipients that upon dissolving will provide a reagent solution having the appropriate concentration.

The kit comprises one or more containers with a label and/or instruction. The label can provide directions for carrying out the preparation of the agents for example, dissolving of the dry powders, and/or treatment for cognitive impairment, anxiety and/or depression.

The label and/or the instructions can indicate directions for in vivo use of the pharmaceutical composition. The label and/or the instructions can indicate that the pharmaceutical composition is used alone, or in combination with another agent to treat a) treating any of depression induced by chronic stress; depression in a subject afflicted with PTSD; anxiety induced by chronic stress; anxiety in a subject afflicted with PTSD; cognitive impairment induced by chronic stress; altered morphology and/or reduced number of GFAP+ cells in hippocampus and/or frontal cortex induced by chronic stress; working memory impairment in a subject afflicted with PTSD; b) inhibiting or reversing loss of GFAP+ cells in hippocampus and/or frontal cortex induced by chronic stress; c) decreasing consolidation of contextual fear memory in a subject afflicted with PTSD; d) enhancing extinction of fear memory in a subject afflicted with PTSD; or (e) increasing calcineurin A expression in a subject afflicted with PTSD using a combination of cotinine and an antioxidant. The label may indicate appropriate dosages for the agents of the invention as described supra.

Suitable containers include, for example, bottles, vials, and test tubes. The containers can be formed from a variety of materials such as glass or plastic. The container can have a sterile access port (for example the container can be an intravenous solution bag or a vial having a stopper pierceable by a needle such as a hypodermic injection needle).

The following example is intended merely to illustrate the practice of the present invention and is not provided by way of limitation. The disclosures of all patent and scientific literatures cited herein are expressly incorporated in their entirety by reference.

EXAMPLES

Example 1

Materials and Methods
Animals:
C57BL/6 mice were obtained from the University of Chile (Chile) and maintained on a 12:12 light-dark cycle with ad libitum access to food and water. Mice were maintained in a controlled environment with an average temperature of 22-25° C. and 30-50% humidity. Mice were kept according the mandate of "the Guide of Animal care and use of laboratory animals of the National Institute of Age". Protocols were performed with the approval of the Institutional Animal Care and Use Committees of the University of San Sebastian, Chile.

Experiment 1

Current evidence suggested that cotinine could reduce anxiety, and depression in subjects with stress-induced depression. The main target of cotinine is the nAChRs. ACh is the main agonist of the nAChRs, and one of the most important neurotransmitters in the central nervous system (CNS) and peripheral nervous system (PNS).

Experimental Design

This study investigated the effect of IN cotinine and low doses of cotinine on PTSD symptoms. Stress was induced by immobilization for a three-weeks period. After this time, mice were treated with IN phosphate buffered saline (PBS) or cotinine and 2behaviorally tested. The depressive behaviors, anxiety and memory were evaluated with using behavioral test, Porsolt's, open field, elevated plus maze, and novel object recognition tests.

Drug Treatments

Mice were treated immediately after the 21 days of immobilization stress (6 h/day) until euthanasia. Mice (n=5-8/condition) received daily treatments with 1. PBS (phosphate buffer saline, pH 7.4) via intranasal (2×12 µl/nostril), 2. PBS via gavage (50 µl); 3. Cotinine dissolved in PBS via oral (gavage, (0.5 mg/kg; Cot 0.5); 4. Cotinine dissolved in PBS via intranasal (Cot IN, 10 mg/ml, 2×12 µl/nostril).

Study of Potential Morphological Changes Caused by Cotinine in the Brain of Mice After treatments, the hippocampus and frontal cortex were investigated for changes in neuronal and glia cells architecture by Luxol blue staining, and cresyl violet staining. Also, the expression levels of the astrocyte marker GFAP in cells of the same areas by immunohistochemistry.

Experiment 2

Mice (n=5-8/condition) were treated via oral during and after restraint stress continuously until euthanasia.

Mice received daily treatments with
1. PBS via oral (50 µl)
2. Cotinine dissolved in PBS via oral (gavage, (5 mg/kg; Cot 0.5)
3. Krill oil (KO) via oral (5 mg/ml in PBS, 50 µl) continuously from the beginning of the restraint stress until euthanasia.

Experiment 3

Mice were treated via IN 2 hours after fear conditioning and continuously until euthanasia.

Mice (n=5-6/condition) received daily treatments with 1. PBS (phosphate buffer saline, pH 7.4) via intranasal (2×12 µl/nostril), 2. Cotinine dissolved in PBS via intranasal (Cot IN, 10 mg/ml, 2×12 µl/nostril); 3. Cotinine+krill oil both dissolved in PBS via intranasal (Cot IN, 10 mg/ml+KO, 48 mg/ml, 2×12 µl/nostril).

The intranasal protocols were performed according it was described by Drs. Hanson and Frey teams according to their advice.

Intranasal Delivery of Cotinine

For awake intranasal cotinine delivery, 2-3 months old mice were weighed and labeled before treatments. For delivery, mice were hand-restrained, placed in a supine position, and given two 12 µl drops of 12 µg/µl cotinine, or PBS, into both nares simultaneously. Mice were given an extra 12 µl treatment drop if the subject forcibly ejected or sneezed out solution. Mice were held supine for 5-10 seconds after delivery to ensure all fluid was inhaled. The administration was repeated for days until euthanasia. On days 6 and 7, mice continued their treatment regimen and were subjected to behavioral testing ~3 h after their morning dose. On the evening of day 7, mice were given their last treatment at 7:00 P.M. and killed 3 h later to ensure that biochemical analyses were performed using the same pretreatment increment as the behavior tests. Mice were killed via cervical dislocation by a well-trained investigator. The olfactory bulbs were dissected out and stored at −20° C. for ELISA analysis of cotinine.

Chemicals

Cotinine (5S-1-metil-5-(3-piridil) pirrolidin-2-ona) was obtained from Sigma-Aldrich. Cotinine was prepared by dissolving the compound in sterile phosphate-buffered saline (PBS, Gibco) at 10 mg/ml.

Krill oil was purchased from Walgreens product krill oil omega-3, 300 mg capsules (Superba, USA). Soft gels contain 300 mg krill oil (omega-3 fatty acids 90 mg, EPA (eicosapentanoic acid) 50 mg, DHA (docosahexaenoic acid) 24 mg, Phospholipids 130 mg). No information was provided by manufacturers about the astaxanthin content in the soft gels.

Methods

Experiments 1 and 2

Restraint Stress

To induce chronic stress, the restraint stress paradigm was used as previously described. Mice are immobilized in 50 ml falcon plastic tubes that were attached to mouse cages. The immobilization proceeded during 6 h from 9:00 AM to 3:00 PM in absence of treatments. Tubes have holes in the opposite side of the tube to allow the animal breathing and urination. Mice were almost completely immobilized for 6 h/day for 21 days after which they were permitted freely to move, eat and drink.

Experiment 3

Contextual Fear Conditioning and Extinction:

Contextual FC was performed as described. The conditioning chamber used is surrounded by a sound-attenuating box with a camera connected to freeze frame software (MED Associates Inc.), also equipped to provide a background white noise (72 dB). The conditioning chamber (33 cm×20 cm×22 cm) contains in one side a speaker and in the opposite slide has a 24V light. The chamber has a 36-bar insulated shock grid floor. Mice were placed in the conditioning chamber for 2 min before the onset of a discrete tone (a sound that will last 30 seconds (sec) at 2,800 Hz and 85 dB). In the last two seconds of this tone, mice received a foot shock of 1 mA and kept in the conditioning chamber for 2 min and then returned to their cages. Between trials, the chamber was sanitized with 70% ethanol and dried. Freezing behavior that is defined as the absence of all movement except the one needed for breathing was assessed using the FreezeView Software (MED Associates Inc.).

To assess fear retention and extinction, mice underwent re-exposure to the conditioning chamber in absence of unconditioned stimulus (shock or auditory cues), and freezing behavior was measured. For the retention test, mice were exposed to the conditioning chamber, every day during 3 min, 24 h after the training test and during the extinction protocol for 6 consecutive days. The extinction trials were performed until a decrease in freezing behavior below a 20% was attained. Fear retention and extinction experiments were performed using the same cohorts of mice and reproduced in two separate experiments.

Behavioral Analysis

Experiments 1, 2 and 3

Behavioral analysis was performed using the Any-maze® software (Stoelting CO, USA) to track the activity of animals. Mice were tested for depressive behavior, anxiety, locomotor activity and working memory using the Porsolt's test; Light-dark box (LDB) and the elevated plus Maze (EPM), open field (OF), and Novel object recognition (NOR), respectively.

Elevated Plus Maze:

Anxiety was assessed through the elevated plus maze (EPM). EPM is considered one of the best choices to test anxiolytic effects of drugs. This test is based on the observation that most of the time higher anxiety levels will diminish the time exploring new environments as a form to avoid danger (open arms).

To determine the level of anxiety, mice were tested in the EPM. The EPM consists of two well-lit open arms and two enclosed arms facing each other and converging into a common center platform (4.5 cm square) elevated 40 cm off the floor. Each mouse was placed in the center platform and allowed to explore for 5 min. Video tracking software measures movement in each section (ANY-Maze, Stoelting, Ill.) to determine time spent in the open and closed arms and distance traveled.

Open Field Test (OF):

OF is used to monitor locomotor activity. Mice are individually placed in an uncovered square arena (40 cm×40 cm×35 cm), and allowed to freely explore for 30 min while monitored with a video tracking software (ANY-Maze, Stoelting Co.) under moderate lighting. Several parameters including, total distance traveled, speed, rearing behavior and time spent in the center and peripheral zones (20 cm×20 cm) are measured to assess locomotor activity and behavioral changes induced by stress.

Porsolt Test (PT):

This test is used to measure the antidepressant effects of drugs, and consists in placing each mouse in a transparent cylinder filled with water at room temperature (RT). After a brief period of strong activity, rodents adopt a characteristic immobile posture. The time mice spent immobile is a measure of depressive-like behavior. The immobility time will be recorded during a 15-min and a next day 5-min trial. The time spent by each mouse immobile will be recorded.

Novel Object Recognition (NOR) (Visual Recognition Memory Test)

After a habituation step in the OF arena, each mouse was individually placed in the apparatus containing two identical objects located equidistant to each other (familiarization phase) and left to explore the objects for 5 min. Then, mice were returned to their cages and permitted to rest for 30 min. After this time, mice were individually placed back in the same arena containing one of the old objects present during the previous trial and a new object. The time exploring the two objects was recorded during 5 min. Exploratory behavior is normalized for animal activity by calculating the exploring Index, that corresponds to the time spent by the mouse exploring the new object/total time spent exploring both objects)×100%. For behavioral recording and documenting the software Any-Maze was used.

Morphological and Astrocytes Analysis

Brain Tissue Preparation

After the behavioral testing, mice were euthanized and brains were removed and dissected. Each brain was divided into two parts, left and right hemispheres. The frontal cortex and hippocampus were dissected from left hemisphere on ice and quickly frozen for subsequent analyses at −80° C. The right hemispheres were post-fixed in 10% buffered formalin (pH7.4) for 48 hours, included in paraffin, sliced in 4 μm sections and mounted in slides for histological and immunohistochemical analysis.

Immunohistochemical Analysis of GFAP Expression and GFAP+ Cells

Paraffin slices were rinsed and subjected to antigenic recovery in buffer citrate pH 6 (Biocare Medical, Walnut Creek, Calif.) for 30 min. Next, slides were incubated with an endogenous peroxidase blocking solution, consisting of hydrogen peroxide 3%, for 5 minutes, washed with PBS, and blocked to prevent unspecific protein binding by incubation with horse serum (Vectastain Elite ABC, Vector Laboratories, Burlingame, Calif., USA) for 10 min at room temperature. Sections were washed in PBS and incubated for 1 hour at room temperature with the primary antibody Glial fibrillary acidic protein (GFAP) (clone—5 g) to 1:100. After washing with PBS, sections were incubated with a biotinylated secondary antibody solution for 10 minutes. Then slides were washed with PBS and incubated kit amplifier solution for 10 minutes at room temperature. The reaction was visualized using ImmunoDetector DAB (SB Bio Inc., Santa Barbara, Calif., USA). For counterstaining, slices were counterstained with Hematoxylin for 30 seconds and dehydrated in ascending gradient of alcohol 95% to 100%, cleared in xylene, and mounted with synthetic resin.

Determination of the Area of Immunostaining with GFAP

Three digital images of the slides immunostained for GFAP immunoreactivity (IR) were obtained of the hippocampus and frontal cortex using a digital camera attached to an inverted microscope at 40× magnification (Micrometrics, MilesCo Scientific, Princeton, Minn., USA) operated by software Micrometrics (Micrometrics SE Premium). To quantitate GFAP immunoreactivity the area of immunostaining was delimited and quantitated using the ImageJ software, provided by the National Institute of Health (NIH, Bethesda, Mass., USA).

Statistical Analysis

All values expressed as mean±standard error of the mean. The behavioral and immunoreactivity differences between sample and treatment groups were determined by One-way or two-way analysis of variance (ANOVA) with Post hoc Tukey analysis. $P<0.05$ was considered as statistically significant. All statistical analyses were performed with the software GraphPad Prism 6 (GraphPad Software Inc., San Diego, Calif., USA).

Results

Experiment 1

Behavioral Effects of Intranasal Cotinine

The behavioral study showed that restraint stress provokes cognitive decline and an increase in anxiety, depressive symptoms and locomotor activity. Intranasal Cotinine treatment normalized the behavior of mice.

Effects of Cotinine IN on Locomotor Activity

In the elevated plus maze (EPM) in anxiety behavior expressed as a decrease on rearing behavior, a sign of anxiety in rodents. The analysis of rearing activity showed a significant difference between groups (F $(4,24)=26$, $p<0.001$). RS mice showed a significant increase in rearing activity (Tukey's posttest, $p<0.001$) when compared to Ctrl mice treated IN with PBS (FIG. 1A). However, mice treated with cotinine did not show differences with Ctrl non-restrained mice. Also treatment groups showed significant differences in distance traveled (F $(2.10)=13.72$) $p=0.0014$) (FIG. 1A). Mice subjected to RS also showed an increase in locomotor activity in the EPM when compare to control non-retrained mice (Tukey's post-test $p<0.01$). Cotinine also in this tests reduced significantly the locomotor activity in the RS mice (Tukey's posttest $p<0.01$) (FIG. 1B). In the open field test, mice showed a significant difference between treatment groups in locomotor activity indicated by significant differences in distance traveled (F $(3,18)=3.287$, $p=0.028$). A significant increase in locomotor activity, expressed as distance traveled, was observed in the mice subjected to chronic RS when compared to Control mice (Ctrl), treated with PBS via intranasal ($p=0.012$). However, restraint stressed mice (RS) treated with cotinine showed a clear trend of decrease in locomotor activity during the 25 minutes (min) of testing (IN Cot: 61±6 m vs 44±18 m, $p=0.058$) (FIG. 1C).

Also the study of changes in anxiety behavior using the light-dark box (LDB), showed significant changes between groups (F $(4,23)=3.597$, $p<0.02$). Ctrl mice no subjected to stress showed higher number of entries to the light zone than RS mice (t=2.351, df 8, p=0.046). Cotinine almost completely restored the number of entries to the light zone considered a decrease in anxiety behavior (t=2.482, df=9, p=0.035).

Effect of Intranasal Cotinine on Working Memory after Chronic Restraint Stress

Since immobilization stress induces cognitive impairment, we tested the effect of posttreatment with cotinine IN on cognitive abilities using the NOR test. The NOR measures visual recognition memory, a form of semantic memory affected by stress. The results showed a significant difference between treatment groups in short term visual memory as expressed as entries to the area of the novel object (F (3,18)=4.220, p=0.02). vehicle-treated RS mice displayed working memory deficits when compared to non-immobilized mice in the PT (p<0.05) (FIG. 2).

Figure 2D:
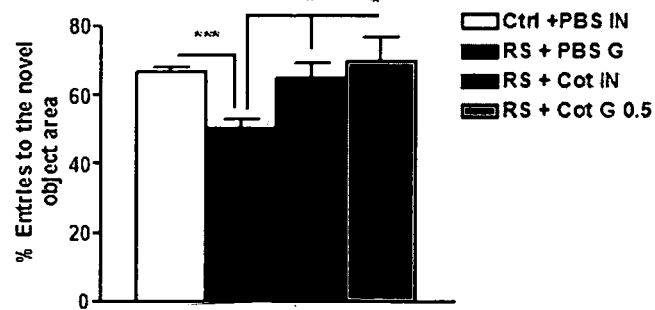

Following 14 days of treatment with cotinine, cotinine significantly increased the number of entries that the RS mice made into the area of the new object in the NOR test. Vehicle-treated RS mice displayed lower number of entries than control non-stressed mice (p<0.01). Cotinine IN increased the number of entries into the new object area to control values (p<0.05) (FIG. 2D).

Effects of Intranasal Cotinine on Depressive-Like Behavior

Figure 3:
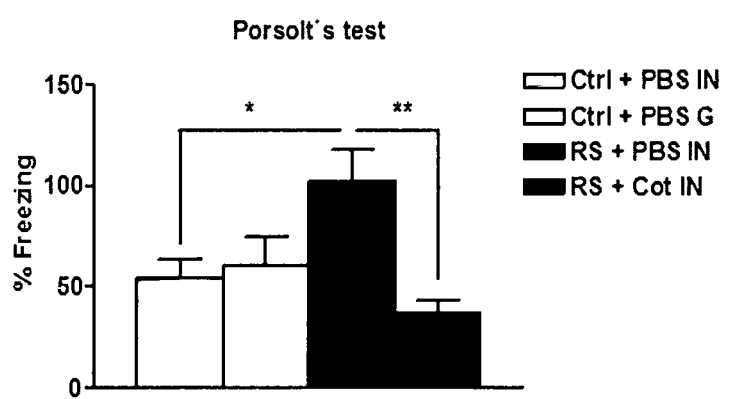
FIG. 3: Cotinine decreased depressive behavior in the Porsolt's tests in mice subjected to restraint stress. Cot 0.5, Cotinine 0.5 mg/ml; Ctrl, Control non-stressed mice; G, Gavage; IN, intranasal; PBS, phosphate Buffer saline; RS, restraint stress.

Persons subjected to inescapable stress have a high incidence of depression. High levels of depressive-like behavior, expressed as increased immobility in the PT, have been observed in mice subjected to immobilization stress (Grizzell et al 2014). In the PT, mice subjected to chronic restraint stress showed higher levels of immobility than control mice. We have previously shown that cotinine reduces depressive-like behavior in C57BL/6 mice (Grizzell et al., 2014). However, nothing is known regarding cotinine's effects on depressive-like behavior when administered as a posttreatment after prolonged immobilization stress via intranasal. We found a significant difference between treatment groups when compared to controls (One-way ANOVA, F (2,13) =8.840, p=0.0038). Mice subjected to RS showed a significant increase in freezing behavior in the PT (p<0.05). Stressed mice post treated with cotinine via IN showed a significant decrease in depressive-like behavior (p<0.01) (FIG. 3).

Analysis of the Expression of GFAP

The qualitative analysis of the frontal cortex and hippocampus, showed a significantly reduced level of GFAP+ cells in the hippocampus and cortex of mice subjected to RS, while a recovery of this expression was observed in the stressed group treated with cotinine.

Figure 4A:
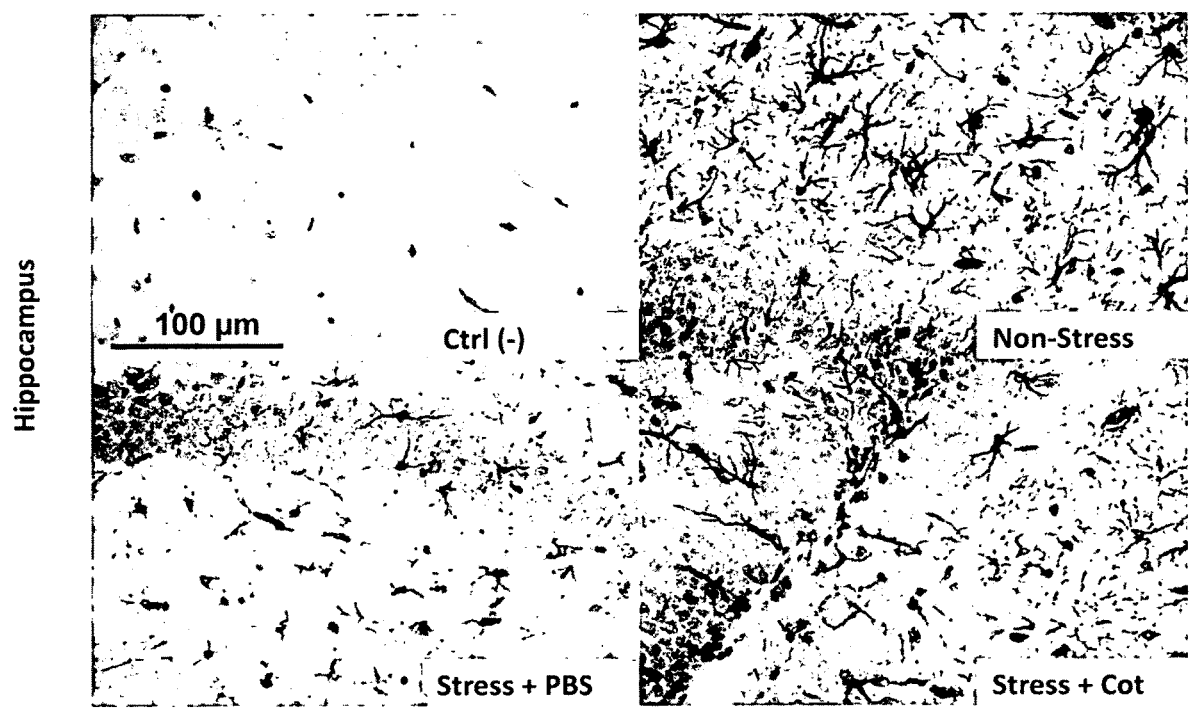
FIG. 4A-B: Cotinine restored astrocytes levels in the brain of mice subjected to restraint stress. A, Hippocampus; B, Prefrontal cortex

On the other hand, the dendrites of the GFAP positive cells, astrocytes, in the stress group possessed a distinct morphology from the control group and RS group treated with cotinine. The morphometric measurements were performed in 40× digital images that were randomly taken from the tissue areas of interest. The results revealed highly significant differences in GFAP+IR between Control mice and RS mice in the hippocampus (8575, 748 $\mu m^2$, vs 15628.456 $\mu m^2$) (FIG. 4A).

Figure 4B:
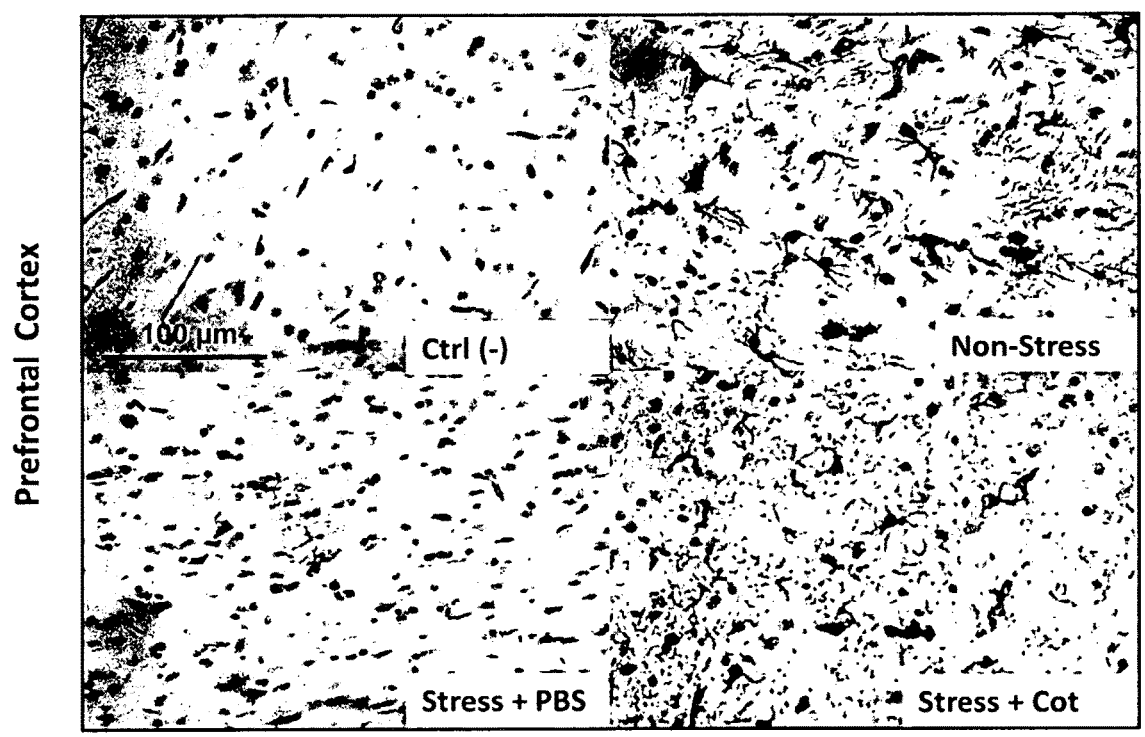

Similarly, In the frontal cortex, RS mice showed a significant decrease in GFAP IR when compared to control mice (average area of IR: Control mice 4024, 904 $\mu m^2$ vs RS mice, 564,174 $\mu m^2$) (FIG. 4B).

Conclusions

Restraint stress, a condition suffered by people with paralysis as the result of traumatic spinal injury or stroke, or reduced mobility induced by overweight or diseases causing pain on extremities as well as because involuntary restraint in mammals.

This stress paradigm is a well investigated model of chronic stress that permits to investigate neuronal changes induced by chronic stress and various PTSD behavioral symptoms such as anxiety, treatment resistant depression, including feeling of hopelessness and cognitive impairment.

Current evidence show that cotinine intranasal and krill oil exerts a more efficient effect preventing or restoring cognitive abilities than any of the compounds alone and mood equilibrium in mouse with neurodegenerative conditions or subjected to high levels of stress. In this study, we discovered that cotinine administered via IN, restores GFAP+ astrocytes expression diminished by restraint stress.

The Intranasal Delivery of the Mix Cotinine Plus KO Decreased Depressive-Like Behavior after Immobilization Stress More Effectively than Cotinine or KO Alone In the PT, mice subjected to chronic restraint stress showed higher levels of immobility than control mice. Both cotinine and KO reduced depressive-like behavior induced by stress paradigms in rodents. However, nothing was known regarding the effects of cotinine plus KO on depressive-like behavior when administered as a cotreatment during prolonged immobilization stress via oral.

We found a significant difference in depressive-like behavior between treatment groups when compared to controls (One-way ANOVA, F(7.46)=5.147, p=0.0002). Mice subjected to RS showed a significant increase in freezing behavior in the PT (p<0.05). Stressed mice cotreated with cotinine 5 mg/kg showed a non-significant decrease in depressive-like behavior.

Figure 5:
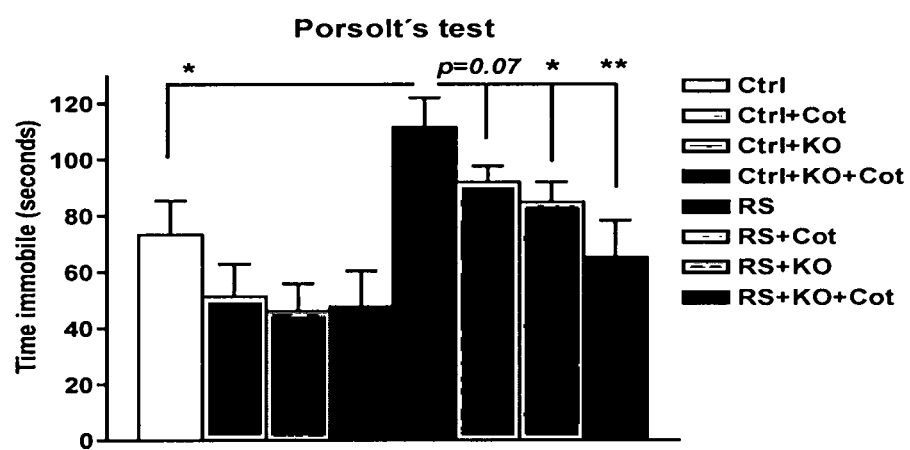
FIG. 5: The oral combination Cotinine plus krill oil was more effective in decreasing depressive behavior than its components alone in the Porsolt's tests in mice subjected to restraint stress. Cot, Cotinine 5 mg/ml; Ctrl, Control non-stressed mice; KO, Krill oil; RS, restraint stress.

KO-treated stressed mice showed a significant decrease in freezing behavior (p<0.05). Outstanding, the mix Cotinine 5 mg/kg+KQ 74 mg/kg showed a superior effect in reducing depressive-like behavior inducing a highly significant decrease in freezing behavior in the PT (p<0.01) (FIG. 5).

Figure 8:
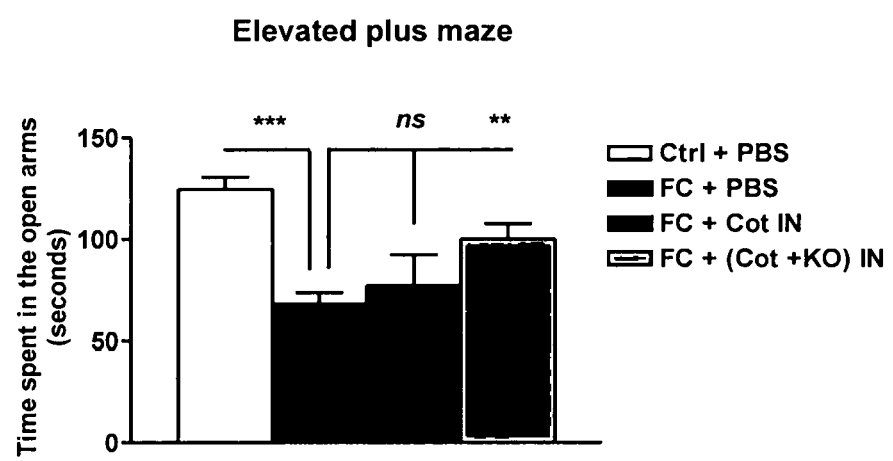
FIG. 8: The Intranasal use of the combination Cotinine plus krill oil was effective in improving depressive-like behavior in mice subjected to fear conditioning. Cot, Cotinine 10 mg/ml; Ctrl, Control non-stressed mice; IN, intranasal; KO, Krill oil; FC, fear conditioning.

Effect of the Intranasal Combination of Cotinine Plus Krill Oil on Working Memory after Fear Conditioning Fear conditioning a model of PTSD mimics in rodents the working memory deficits observed in humans exposed to traumatic events, we tested the effect of post-treatment with cotinine IN on working memory using the NOR test. The results showed a significant difference between treatment groups in working visual recognition memory as expressed as time spent in the area of the novel object (F(3.16)=14.72, p<0.0001) or number of entries to the area of the novel object(F(3.14)=7.315, p<0.0035). PBS-treated FC mice spent less time (p<0.01) and performed a lower number of entries (p<0.01) to the novel object than ctrl non-stressed mice (FIG. 8).

Figure 6:
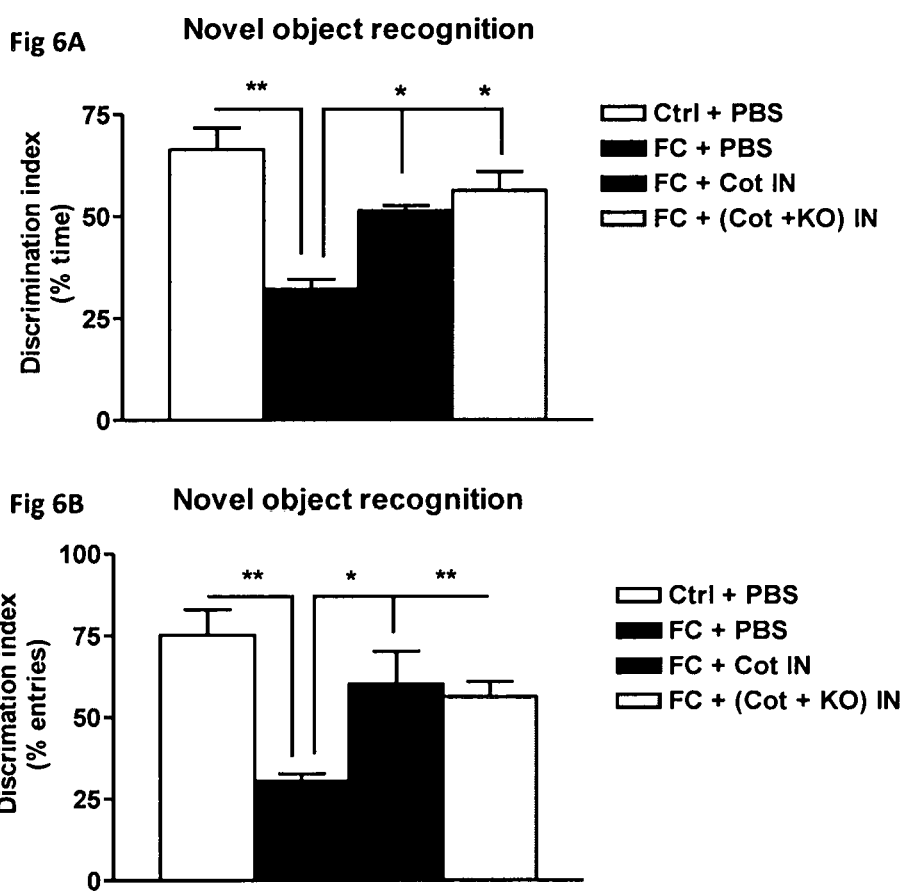
FIG. 6A-B: The Intranasal use of the combination Cotinine plus krill oil was effective in improving working memory in the novel object recognition test in mice subjected to fear conditioning. Cot, Cotinine 5 mg/ml; Ctrl, Control non-stressed mice; KO, Krill oil; FC, fear conditioning.

Mice post-treated with cotinine alone or cotinine plus KO, performed a higher number of entries to the new object area than PBS-treated FC mice (Cotinine, p<0.05; Cotinine+KO, p<0.01 (FIG. 8). Similar results were obtained when the time exploring the new object was assessed, cotinine-treated FC mice spent more time than PBS-treated FC mice (Cotinine, p<0.05; Cot+KO, p<0.05) (FIG. 6).

Figure 7:
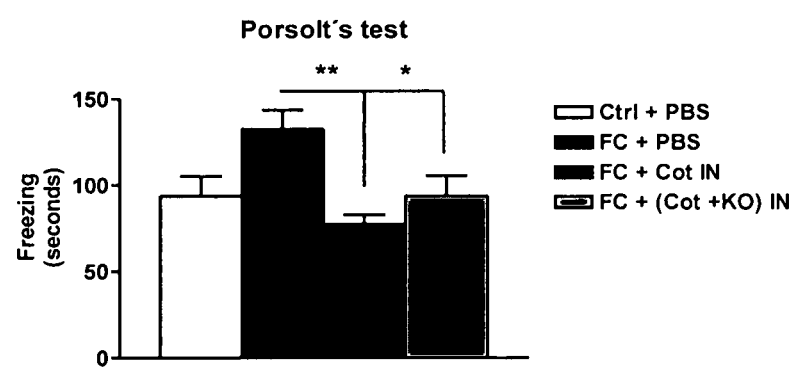
FIG. 7: The Intranasal use of the combination Cotinine plus krill oil was effective in improving working memory in the novel object recognition test in mice subjected to fear conditioning. Cot, Cotinine 10 mg/ml; Ctrl, Control non-stressed mice; IN, intranasal; KO, Krill oil; FC, fear conditioning.

Effect of Intranasal Post-Treatment with the Combination of Cotinine Plus Krill Oil to Alleviate Anxiety, Depression and Working Memory Deficits after Fear Conditioning Effects of Cotinine Plus Krill Oil on Anxiety Behavior Also, the analysis of depressive-like behavior in the PT, revealed a significant difference between treatment groups (One-way ANOVA, F(3.15)=5.564, p=0.009). Mice subjected to FC with a single shock showed higher levels of depressive-like behavior/hopeless than Ctrl mice treated with PBS. Mice subjected to FC showed a significant increase in freezing behavior in the PT than controls (p=0.05). FC mice post-treated with cotinine via intranasal showed a significant decrease in depressive-like behavior (p<0.01); no higher effect was observe with the combination Cotinine plus KO (p<0.05) (FIG. 7)

In the EPM anxiety test, mice showed a significant difference between treatment groups in locomotor activity indicated by significant differences in the time spent in the center zone a measure of anxiety levels (Kruskal-Wallis, KW statistic=9.642, p=0.022). FC induced a significant increase in anxiety in the stressed mice, expressed as a decrease in the time spent in the open arms, when compared to non-conditioned and vehicle-treated mice (t=4.9, df=9, p<0.008). However, conditioned mice (FC) treated after FC with cotinine or cotinine plus KO via intranasal, showed a decrease in anxiety expressed as an increase in the time spent in the open arms but the difference did not reached significance (Veh: 68.14±5.573 seconds, N=5 vs Cot+KO: 107.4±32.44, N=5. However, the combination cotinine plus KO was more effective reducing anxiety behavior and significantly increased the time the mice spent in the center zone with less variability between subjects (68.14±5.573 N=5 vs 108.6±10.43 N=6, t=3.218 df=9, p<0.01) (FIG. 8).

Effect of the Combination of Cotinine and Krill Oil on Fear Retention and Extinction after Fear Conditioning To study the effect of post-treatment with cotinine on extinction of contextual fear memory, mice were trained for contextual fear conditioning (FC), and 2 h later, before the retention test, mice were started on cotinine treatment. Mice were treated with daily doses of vehicle, cotinine (10 mg/ml) or cotinine+KO (48 mg/ml) during the contextual fear extinction trials and until euthanasia. Similarly, no effect of cotinine on fear memory retention was observed when fear-conditioned mice were subjected to the contextual retention test, a 3-min exposure to the context chamber without electric foot shock) 24 h after FC training.

Cotinine and Cotinine Plus Krill Oil Enhanced Contextual Fear Extinction

Next, we assessed the effect of cotinine and/or KO on contextual FE. Mice underwent a single FC training trial, and were started on IN treatment with vehicle (PBS), cotinine (10 mg/ml, 24 µl) or (cot 10 mg/ml+KO 24 µl). Next day mice were subjected to a retention test, and re-exposed daily to the conditioning chamber for 3 min without electric shock or sound for 6 consecutive days. The fear response of the mice expressed as freezing behavior, a measure of contextual fear memory, was recorded daily during the extinction trials. During the retention test, cotinine-treated mice showed levels of freezing similar to control mice indicating that cotinine did not interfered with the consolidation of the fear memory; however, mice treated with the mix (Cot+KO) showed a significant decrease in the consolidation of the contextual fear memory (t=2.915, df=7, p=0.02).

Figure 9A:
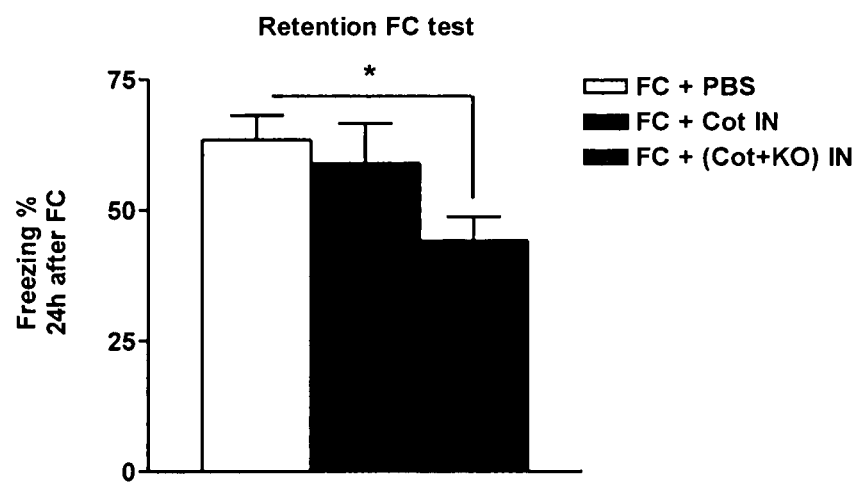

All groups of mice showed an almost complete extinction of freezing in four days. However, cotinine-treated mice showed a significant enhancement of memory extinction on day 2 and 3 reaching a maximal decrease at day 3 (one-way ANOVA: F(2.18)=5.778, p<0.05). Mice treated with the mix (Cot+KO) showed lower fear responses that controls, but reached a maximal decrease at the same time than control mice on day 5 (FIG. 9).

Conclusions

These data indicated that the combination of cotinine plus antioxidant, KO, but not cotinine alone can decrease the consolidation of fear memory, reducing the initial fear response when exposed to the trauma context.

Example 2

Materials and Methods

Animals

Mice were obtained from the animal facilities of the University of Chile, and maintained with free access to commercial food and water, in a controlled environment with an average temperature of 22° C. under a 12 h/12 h dark/light schedule. C57BL/6 male mice weighing between 20-30 grams (g) and aged about 2-3 months were used. Mice were acclimatized to the housing facility for a week before experiments. Test and animal care were performed according to protocols approved for the Universidad San Sebastian ethical committee and performed in compliance with the Guide for the care and use of Laboratory Animals adopted by the National Institute of Health (USA). Mice were weighed twice a week during the performance of the experiments and until euthanasia.

Drugs and Reagents

Cotinine ((5S)-1-methyl-5-(3-pyridyl)-pyrrolidin-2-one) and other miscellaneous reagents were obtained from Sigma-Aldrich (Saint Louis, Mo.) unless stated otherwise.

Experimental Groups and Drug Treatments

Figure 10:
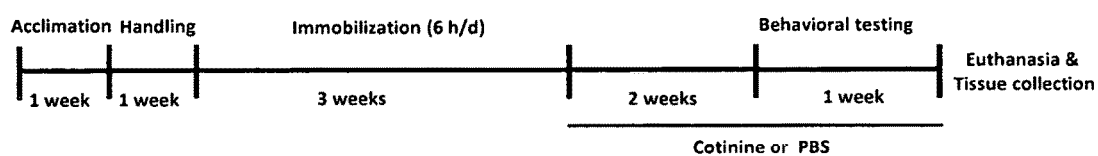
FIG. 10. Diagram representing the experimental design. Male mice (n=6-8/condition) were housed and habituated to their cages before restraint stress or resting conditions were applied. After this period mice were treated, behaviorally tested and euthanized. IHC analysis was then performed in selected brain regions of the mice.

Mice between 2-3 months of age after one week of acclimatization were randomly divided into two groups. Stressed mice were subjected to restraint stress. Control (non-restrained) mice were allowed to move freely during this period. After the stress exposure period, mice were divided into three experimental groups: 1) Non-restrained mice treated with vehicle (PBS, pH 7.4) serving as unstressed controls (n=8); 2) Restrained mice (RS) treated with vehicle (n=8); 3), RS mice treated with 24 µl of a cotinine solution (10 mg/ml in PBS, pH 7.4) via intranasal route of administration (n=6). Treatments were administered daily until euthanasia. After two weeks of treatments mice were behaviorally tested and euthanized (FIG. 10)

Awake Intranasal Cotinine Delivery

Intranasal delivery was performed as previously described (Hanson and Frey, 2007). Mice at 2-3 months of age were hand-restrained, positioned in a supine position, and administered two 12 µl drops of cotinine solution (10 mg/ml in PBS), or PBS alone, into both nares. Mice were given an extra 12 µl treatment drop if the mouse expelled out the solution. Mice were kept in the supine posture for 5 seconds after delivery to facilitate the delivery. The administration was performed daily until euthanasia. Mice were subjected to behavioral testing about 2 hours after their morning dose. Mice were euthanized using cervical dislocation by a well-trained investigator.

Restraint Stress

The stress paradigm was performed as previously described (Grizzell et al., 2014a). Briefly, mice were immobilized inside transparent 50 ml conic transparent tubes. Tubes permitted only subtle movements of the mice and contained holes in both ends to allow normal animal breathing. Mice were immobilized for 6 hours/day for 21 days at less than 300 lux.

Behavioral Analysis

Mice were tested for locomotor activity and working memory using the open field (OF) and Novel object recognition (NOR) tests, respectively. Depressive-like behavior, and anxiety were tested in the forced swim (depressive-like behavior) and the elevated plus maze (EPM) (anxiety) tests, respectively. Animal behavior was recorded and analyzed using the ANY-Maze® software (Stoelting CO, USA).

Open Field Test (OF)

OF was conducted to monitor locomotor activity as described (Zeitlin et al., 2012). Mice were individually placed in an uncovered square arena (40 cm×40 cm×35 cm), allowed to freely explore for 30 minutes (min) while monitored with a video tracking software (ANY-Maze®, Stoelting Co., Illinois, USA) under moderate lighting. Several parameters including total distance traveled, speed, and time spent in the center and peripheral zones (20 cm×20 cm) were measured to assess locomotor activity.

Forced Swim Test

The forced swim test (FST) is a reliable and extensively used test to measure the effect of antidepressants (Naitoh et al., 1992). We have previously shown that this test is reliable to test stress-induced depression after restraint stress as follow. Mice were placed in a transparent cylinder filled with water at 25° C. for 5 min and behavior was recorded. After a brief period of strong activity, rodents adopt a characteristic immobile posture. Immobility is defined as the time the mouse was engaged in only the minimal movements required for breathing and to keep the head above the water.

Novel Object Recognition (NOR, Visual Recognition Memory Test)

The NOR test permits investigators to determine short- and long-term recognition memory, as well as motivation for novelty (Antunes and Biala, 2012; Grayson et al., 2015; Yang et al., 2015). Cognitive enhancement in this tests has been reported using α7nAChRs agonists and 5-HT antagonists (Antunes and Biala, 2012).

The NOR test starts with a habituation step that consists in putting each mouse to freely explore an open and empty testing arena (40 cm×40 cm×35 cm) for 10 min. On the next day, each mouse was placed in the same arena but containing two identical objects located equidistant to each other (familiarization phase) and led to freely explore the objects for 5 min. Then, mice were put back to their cages and permitted to rest for 30 min. After this time, each mouse was placed back in the arena containing one of the old objects that were present during the familiarity phase, and a new object. The time exploring the objects was recorded during 5 min in both steps. Exploratory behavior was normalized for animal activity by calculating the exploration index (EI) that corresponds to the time spent by the mouse exploring the new object/total time spent with both objects)×100%. The software Any-Maze (Stoelting Co.) coupled to a recording camera and computer systems was used for behavioral recording and documenting.

Morphological Analyses of GFAP Immunoreactive Cells in the Hippocampus of Mice

Brain Tissue Preparation

For all protein analyses, mice were euthanized and brains removed. Each brain was divided into two hemispheres. The left hemisphere of brains was dissected out to collect the regions of interest and quickly frozen for later analyses. For the immunohistochemical (IHC) analysis the right hemisphere of each mouse brain was placed in 10% formalin in PBS pH 7.4 for 48 h and then embedded in paraffin. Each region of interest was located using Paxinos Atlas as a reference (Paxinos and Franklin, 2004), and serial cortices of 4 μm (n≥5/mouse) were collected using the Microtome Leica RM 2125RT and mounted on silanized glass slides.

GFAP$^+$ Cells Immunohistochemical Analysis

The analysis of GFAP$^+$ cells was performed using tissue slices containing the ventral hippocampus (Approx. Bregma −4.08 mm, interaural 4.92 mm) and frontal cortex (Approx. Bregma 3.2 mm, interaural 1.54 mm). Sagittal sections of brains were collected in PBS and processed for GFAP immunoreactivity (IR). Brain slices were immersed in xylene and a decreasing graduation of ethanol baths for hydration. Then, slides were subjected to a standard process of antigenic recovery in buffer citrate pH=6 in a pressurized saucepan (Biocare Medical, Walnut Creek, Calif.) for 30 min. Next, slides were incubated with a solution of 3% hydrogen peroxide to block endogenous peroxidase for 5 min, washed with PBS, and blocked with a horse serum solution (Vectastain Elite ABC, Vector Laboratories, Burlingame, Calif., USA) for 10 min at room temperature (RT). Sections were washed in PBS and incubated for 1 hour (Franklin, 2001) at RT with an antibody against GFAP 1:100 (Sigma). After washing with PBS, sections were incubated with a biotinylated secondary antibody for 10 min. Then, sections were washed with PBS and incubated with the amplifier solution from the Vectastain Elite kit for 10 min at RT. The reaction was visualized using ImmunoDetector DAB (SB Bio Inc., Santa Barbara, Calif., USA). For counterstaining, sections were stained with hematoxylin for 30 seconds (sec), dehydrated in baths of ascending percentages of alcohol solutions and xylene, and mounted with synthetic resin.

For the IR analysis, for each mouse, three digital images were randomly selected at 40× magnifications in the areas of interest (hippocampus and frontal cortex) (n=5-6/condition). The images were taken using a digital camera attached to a light microscope (Micrometrics, MilesCo Scientific, Princeton, Minn., USA) connected to a camera operated by a commercial software (Micrometrics SE Premium). The determination of the area of the immunolabeling was calculated delimiting the IR areas using the ImageJ software (National Institute of Health, Bethesda, Mass., USA). For all analyses, GFAP$^+$ astrocytes were selected randomly from the frontal cortex and the CA1, CA3 and dentate gyrus regions of the hippocampus and quantified. Using a digital camera on an inverted microscope, black and white images of GFAP$^+$ astrocytes were obtained and processed with Image J software. Using a 20× objective, cells were chosen randomly in the same area selected for immunostaining, and the binary overlay of a cell was created by thresholding. For all images, a threshold value was established at the level at which the binary overlay entirely enclosed the cell body and projections. All pixels above the threshold value were considered as belonging to the cell images. Finally, the binary silhouette of the whole cell was reduced to its one-pixel outline for estimation of the fractal dimensions with the FracLac 2.5 ImageJ plug-in (Karperien et al., 2013; Karperien and Jelinek, 2015)

Quantitative Fractal Analysis

Fractal analysis was done on binary images by means of the dilation method (Schaffner and Ghesquiere, 2001). The slope of the regression line (S) is related to the fractal dimension (D) by D=1−S. Each pixel in the cell outline was replaced with a disk of a diameter fluctuating from 3-61 pixels and the area of the widened outline divided by the diameter of structuring element was plotted against this diameter on a log-log scale.

Parameters calculated included:

Cellular Area:

the area of the cell body that is calculated as the two-dimensional cross-sectional area contained within the boundary of the cell body.

Arbor Area:

The area of the convex polygon formed by connecting the tips of the longest astrocytic processes (convex hull area).

Convex hull values indicate the size of the branching field of the astrocyte. The amount of physical space is defined in terms of convex-hull volume, surface area, area, and or perimeter.

Lacunarity:

Measures heterogeneity and complements fractal dimension analysis in describing structural complexity (Karperien et al., 2013; Karperien and Jelinek, 2015; Schaffner and Ghesquiere, 2001).

Statistical Analysis

To analyze differences between-groups means in the behavioral and immunohistochemical studies, the following were used. Student's t tests or Kruskal-Wallis were used when comparing two conditions and when comparing three or more levels of a factor, one-way followed by Tukey's or Tukey-Kramer post hoc tests (where applicable) or a repeated measure, 3×3 factorial ANOVA (treatment condition×brain region) followed by Fisher's LSD post-hoc tests were used where appropriate. For the IHC analyses of hippocampal subregions, each mouse brain contained several GFAP+ cells which were then averaged across subject by region and included in the analyses as mouse being the foci of analyses. When individual cells were used as the unit of focus in the analyses, the results were similar. All statistical analyses were performed with the software GraphPad Prism 6 (GraphPad Software Inc., San Diego, Calif., USA) and SPSS 24 (IBM, Armonk, N.Y., USA). Differences were considered statistically significant for p-value<0.05.

Results

Effect of Posttreatment with Intranasal Cotinine on Stress-Induced Changes in Locomotor Activity To assess changes in locomotor activity related to restraint stress and cotinine treatment, we first tested each mouse in the open field, a task that permits investigators to assess changes in locomotor activity and anxiety behavior. One-way ANOVA analysis revealed significant differences between treatment groups in locomotor activity, expressed as distance traveled in the OF test ($F_{(2,17)}=5.144$, $p=0.018$). A Tukey Post-hoc analysis indicated a significant increase ($p<0.05$) in locomotor activity in the PBS-treated restrained mice when compared to PBS-treated control mice (Ctrl+PBS: 32±18 meters (m) vs RS+PBS: 61±19 m, $p<0.05$) (FIG. 10A). Restrained mice treated with IN cotinine showed lower values of distance traveled than vehicle-treated restrained mice (RS+PBS: 61±19 m vs RS+Cot: 49±13 m) and that were no significantly different from the nonstressed control group ($p<0.05$) (FIG. 11A).

Effect of Intranasal Cotinine on Stress-Induced Changes in Depressive-Like Behavior It has been previously shown that chronic immobilization stress is associated with depressive-like behavior in rodents (Ferraz et al., 2011). The time mice spent immobile in the forced swim test is a measure of depressive-like behavior in rodents (Karl, Pabst, & von Horsten, 2003; Naitoh et al., 1992). We have shown that oral cotinine administered before and continuously to restrained C57BL/6 mice, substantively decreased depressive-like behavior induced by stress (Grizzell et al., 2014a). Similarly, in this study we found significant differences in depressive-like behavior between treatment groups ($F_{(2, 13)}=8.848$, $p=0.004$). A post hoc Tukey test revealed that following post-treatment with IN cotinine, the restrained mice showed a significant decrease in immobility in the forced swim test ($p<0.05$). However, cotinine-treated restrained mice showed immobility values not significantly different from controls, but significantly lower than PBS-treated restrained mice ($p<0.01$) (FIG. 11B)

Effect of Intranasal Cotinine on Stress-Induced Cognitive Impairment

To analyze whether intranasal cotinine can revert the stress-induced deterioration in cognitive abilities, we tested the effect of post-treatment with intranasal cotinine on short-term recognition memory in mice. In the familiarization phase, one-way ANOVA analysis revealed no significant changes between groups in the time expend exploring the equal objects ($F_{(2,12)}=0.3422$, $p>0.05$) or entries to the area of each object ($F_{(2,12)}=0.738$, $p>0.05$). However, restraint stress and cotinine induced significant changes in cognitive abilities in this task in the time spent with the new object ($F_{(2,15)}=7.755$, $p<0.01$), as well as the number of entries in the second object area ($F_{(2,14)}=3.756$, $p<0.05$). A Tukey post hoc analysis showed that stressed mice showed a reduction in their cognitive abilities expressed as a decrease in the EI for the new object when compared to control mice ($p<0.01$). Cotinine-treated stressed mice showed better discrimination for the new object showing a significantly higher number of entries to the novel object area when compared to the vehicle-treated stressed mice ($p<0.05$). Also, cotinine-treated stressed mice showed an increase in the exploration index when compared to vehicle-treated stressed mice but the difference did not reach statistical significance (FIG. 12)

Analysis of GFAP Immunoreactivity and GFAP+ Cells Morphology

GFAP+ cells in both hippocampus and frontal cortex possessed a distinct morphology in between groups (FIG. 13). The immunohistochemistry analysis of GFAP+IR cells showed significant differences in GFAP IR between treatment groups in the hippocampus ($F_{(2, 15}=49.08$, $p<0.001$) (FIGS. 13A and 13B) and frontal cortex (One way ANOVA, $p<0.001$) (FIGS. 13A and 13C). GFAP IR was found dramatically reduced in both the hippocampus (−55%, $p<0001$) (FIG. 13A) and frontal cortex (−87%, $p<0.0001$) of the vehicle-treated restrained mice, when compared to the vehicle-treated nonstressed control mice (FIG. 13B). However, cotinine administered after the RS almost completely restored GFAP IR in the hippocampus (84% of control value, FIG. 13B) and frontal cortex (90% of control values, FIG. 13C).

Figure 14:
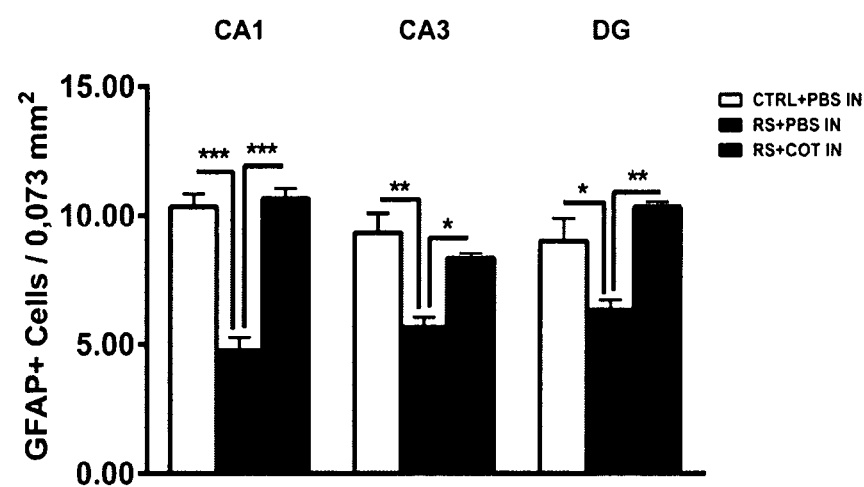
FIG. 14. The changes in GAFP+ cells in the hippocampal formation. Plots represent the number of GFAP+ cells in the different brain regions in Controls non-stressed (CTRL+ PBS IN) mice and a reduced staining intensity in the stressed mice (RS) treated with IN PBS compared to control (CTRL+ PBS IN) and restrained mice treated with IN Cotinine (24 µl, 10 mg/ml)(RS+Cot IN).

GFAP$^+$ Cells Density:

One-way ANOVA analyses of GFAP$^+$ cells were performed in randomly selected quadrants of three sections per mouse. The number of hippocampal GFAP+ cells counted varied according to mice treatments (Ctrl, 144; RS, 97; RS+Cot, 140). The analyses showed that mice subjected to RS showed a significant decrease in the number of astrocytes in the hippocampal regions analyzed when compared to nonstressed control mice (FIG. 14). Similar results were obtained when the frontal cortex of mice was analyzed. However, these abnormalities were corrected by intranasal cotinine treatment. One-way analyzes of cell counting of sections immunoassayed for GFAP IR revealed a significant effect of treatments on the number of GFAP$^+$ cells in the CA1 ($F_{(2, 7)}=43.20$, $p<0.001$), CA3 ($F_{(2, 6)}=13.86$, $p<0.001$) and DG regions ($F_{(2, 6)}=12.92$, $p<0.001$). A multiple comparison test revealed a significant reduction in cell density in the CA1, CA3 and DG regions of restrained mice when compared to control mice (CA1, $p<0.001$; CA3, $p<0.01$; DG, $p<0.05$), respectively. Furthermore, GFAP$^+$ cell density was significantly higher in the cotinine-treated restrained mice relative to vehicle-treated restrained mice (CA1, $p<0.01$; CA2, $p<0.05$; DG, $p<0.01$) (FIG. 14). No significant differences in GFAP$^+$ cell density was observed between vehicle-treated and cotinine-treated control mice.

Changes in the Morphology of GFAP$^+$ Cells Induced by Restraint Stress and Cotinine:

In the stressed mice, GFAP$^+$ astrocytes in the hippocampi and frontal cortices showed different appearances depending on levels of stress and treatments. Small cells mostly with short, tiny and poorly ramified processes were observed in the vehicle-treated restrained mice. At the contrary, large GFAP$^+$ cells with longer and more complex arborization were observed in cotinine-treated restrained mice and non-stressed control mice (FIG. 15A). To evaluate these changes, randomly selected individual astrocytes from the brain areas of interest were analyzed for cell area, arbor area, fractal dimension, and lacunarity.

Effect of Cotinine on Cell Area:

A 3×3 repeated measures ANOVA (treatment condition× brain region wherein brain region is the within-subject factor) revealed a significant main effect of treatment condition in cell area across regions ($F_{(2,8)}=19.755$, $p<0.001$). Post-hoc analyses revealed that across the CA1, CA3 and DG hippocampal regions, the astrocytes of vehicle-treated restrained mice had significantly less cell area than both non-stressed controls as well as cotinine-treated restrained mice ($p<0.05$). Furthermore, the hippocampal cell areas of cotinine-treated restrained mice were statistically indistinguishable from nonstressed controls (FIG. 15B).

Effect of IN Cotinine Arbor Area:

A 3×3 repeated measures ANOVA (treatment condition× brain region) of the arbor area (Hull) revealed significant main effects of both treatment condition ($F (2.8)=18.166$, $p<0.001$) and brain region ($F (2,7)=4.777$, $p<0.05$). Post-hoc analyses reveal that in astrocytes of the CA1, cotinine-treated mice had significantly more arbor area than the non-stressed controls ($p<0.05$) and marginally more than their vehicle-treated, stressed counterparts ($p=0.075$). In the CA3, cotinine-treated, restrained mice had significantly more arbor area of astrocytes than non-stressed controls ($p<0.05$) and vehicle-treated, restrained mice ($p<0.01$) (FIG. 15C). However, in the DG, both cotinine-treated and non-stressed controls had greater astrocytic arborization than vehicle-treated, restrained mice ($p<0.001$) with no differences between cotinine-treated, stressed mice and unstressed controls ($p=0.533$). Although there was a significant main effect of the within-group factor which suggested that levels of arborization differed between brain regions, no post-hoc tests were conducted as we felt this was not pertinent to our investigation.

Effect of IN Cotinine Lacunarity:

A 3×3 repeated measures ANOVA (treatment condition× brain region) revealed a significant main effect of treatment condition in lacunarity ($F (2, 8)=5.067$, $p<0.05$). Post-hoc analyses detected significant differences in the DG only wherein vehicle-treated, restrained mice had reduced lacunarity of astrocytes relative to both their cotinine-treated, stressed and vehicle-treated, non-stressed counterparts ($p<0.05$; FIG. 15D).

Effect of IN Cotinine Fractal Dimension:

A 3×3 repeated measures ANOVA (treatment condition x brain region) of changes in fractal dimension (FD) revealed a significant main effect of treatment condition ($F(2.8)= 5.888$, $p<0.05$). Post-hoc tests revealed that vehicle-treated, restrained mice had a significant reduction in FD of astrocytes in the DG when compared to cotinine-treated, restrained mice ($p<0.05$) as well as a marginal reduction in FD in the CA3 when compared to vehicle-treated non-stressed mice (FIG. 15E).

Discussion

Chronic stress in rodents is considered a good animal model to investigate antidepressants for treatment-resistant depression (TRD) in PTSD. In this work, the effects of post-treatment with IN cotinine on behavior and GFAP+ cells in the hippocampus and frontal cortex of adult male mice subjected to stress were investigated. The results show that IN cotinine normalized the otherwise abnormal behavior in the chronically stressed mice. In addition, we found a clear effect of intranasal cotinine on normalizing the morphology and number of GFAP$^+$ cells in the hippocampus of restrained mice.

Therapeutic approaches for TRD in PTSD patients include treatment with combinations of anxiolytic, antidepressants, sedatives, antipsychotics drugs, and antiepileptic drugs as well as cognitive behavioral therapy (Heinrichs et al., 2013). These treatments, although can temporally reduce anxiety and depression, only a small percentage of patients shows remission and more than 75% maintains the diagnosis of PTSD and or depression at the end of treatments (Javidi and Yadollahie, 2012). Although, some progress has been made in defining biomarkers to predict the potential response to current treatments (Colvonen et al., 2017), new drugs or therapeutic strategies are required. Few new drug candidates (Lee et al., 2017) and other treatments such as transcranial magnetic brain stimulation and hypnotherapy (Rotaru and Rusu, 2016) are currently been tested (Trevizol et al., 2016).

We have shown that co-treatment with orally administered cotinine prevented depressive-like behavior in C57BL/6 mice subjected to immobilization stress (Urizzell et al., 2014a) and female rats subjected to chemotherapy treatments (Iarkov et al., 2016). However, the effect of oral or IN cotinine administered after chronic stress exposure has not been explored before. In the forced swimming test, cotinine almost completely normalized depressive-like behavior and restrained mice not treated with cotinine had immobility values significantly higher than mice post-treated with cotinine.

To define new treatments, it is important to target brain alterations associated with the pathological changes in brain functions. When GFAP+IR was assessed, it was found that RS caused a 55% and 87% decrease in GFAP$^+$ astrocyte IR density in the frontal cortex and the hippocampus, respectively. Cotinine restored GFAP$^+$ IR in both brain regions to control mice values. In addition, IN cotinine normalized the number and morphology of GFAP+ cells, increasing the cell area and structural complexity and length of astrocytes projections in both brain regions studied. These findings agree with previous studies in rodent models of chronic stress showing a decrease in GFAP$^+$ cells in the hippocampus (Orlovsky et al., 2014; Santha et al., 2015). One of these studies showed that stress significantly reduced both the number and body cell volume of astrocytes (both approximately 25%), and that these phenomena correlated with a decrease in the volume of the hippocampal formation and prefrontal cortex. These changes were counteracted by treatment with the antidepressant fluoxetine (Czeh et al., 2007; Czeh et al., 2006; Fuchs et al., 2006; Lucassen et al., 2006). Based on this evidence, further studies have investigated the effect of therapeutic compounds over behavior and astrocyte function (Feng et al., 2015; Xia et al., 2013). Morphological changes of astrocytes may have a serious impact on both neuronal function and viability as astrocytes control the levels of extracellular glutamate, preventing excitotoxicity in the brain. Moreover, a prominent decrease in astroglia has been found in the brain of patients that suffered from major depression disorder (MDD). However, the type of astrocyte pathology in MDD is distinctive from the observed in other neurological and neurodegenerative disorders such as epilepsy (Babb et al., 1996; Webster et al., 2017), traumatic brain injury (Kabadi et al., 2014; Villapol et al., 2014), stroke (Hennessy et al., 2015), amyotrophic lateral sclerosis (Nagai et al., 2007; Radford et al., 2015; Yamanaka et al., 2008), Huntington's disease (Crotti and Glass, 2015; Kim et al., 2015), Parkinson's disease (Liu et al., 2015; Niranjan, 2014) or Alzheimer's disease (Fuller et al., 2010; Li et al., 2011; Ugbode et al., 2017; Winkler et al., 2015). In these disorders, glial scar formation occurs in parallel to astrogliosis, although a protective role of astrocytes has been also suggested in these conditions (Benarroch, 2005; Forster and Reiser, 2016; Otani et al., 2006; Spence et al., 2011; Stobart and Anderson, 2013; Verkhratsky et al., 2013). In MDD there is no astrogliosis, as the expression of GFAP and other markers of astrocytes is decreased, revealing a different pathological mechanism.

Drugs that affect the cholinergic system may be future options for PTSD and depression. Currently several other cholinergic drugs have been tested for treatment resistant depression. Scopolamine, a muscarinic antagonist, has been tested in placebo-controlled studies with positive result (Szczepanik et al., 2016). On the other hand, the nAChRs antagonist mecamylamine has been tested as an augmentation for antidepressants without positive results (Moller et al., 2015).

Numerous studies have shown that cotinine, a modulator of the nAChRs, has beneficial effects on depressive behavior and synaptic plasticity in neurodegenerative and psychiatric conditions (de Aguiar et al., 2013; Echeverria et al., 2016a; Echeverria et al., 2016b; Gao et al., 2014; Grizzell and Echeverria, 2014; Grizzell et al., 2014a; Grizzell et al., 2014b; Grizzell et al., 2017; Patel et al., 2014; Terry et al., 2015; Wang et al., 2015; Wildeboer-Andrud et al., 2014; Zeitlin et al., 2012). The studies have tested the effect of oral doses of cotinine in animal models of pathology and behavior. However, as a potential clinical application, we explored intranasal delivery of cotinine thinking in its use as a fast delivery post-trauma therapy with reduced systemic side effects and costs. The results obtained in the present study show that cotinine helps to improve cognitive abilities, and decreased dramatically depressive-like behavior and anxiety after a week of intranasal administration of the drug dissolved in a saline solution.

Figure 16:
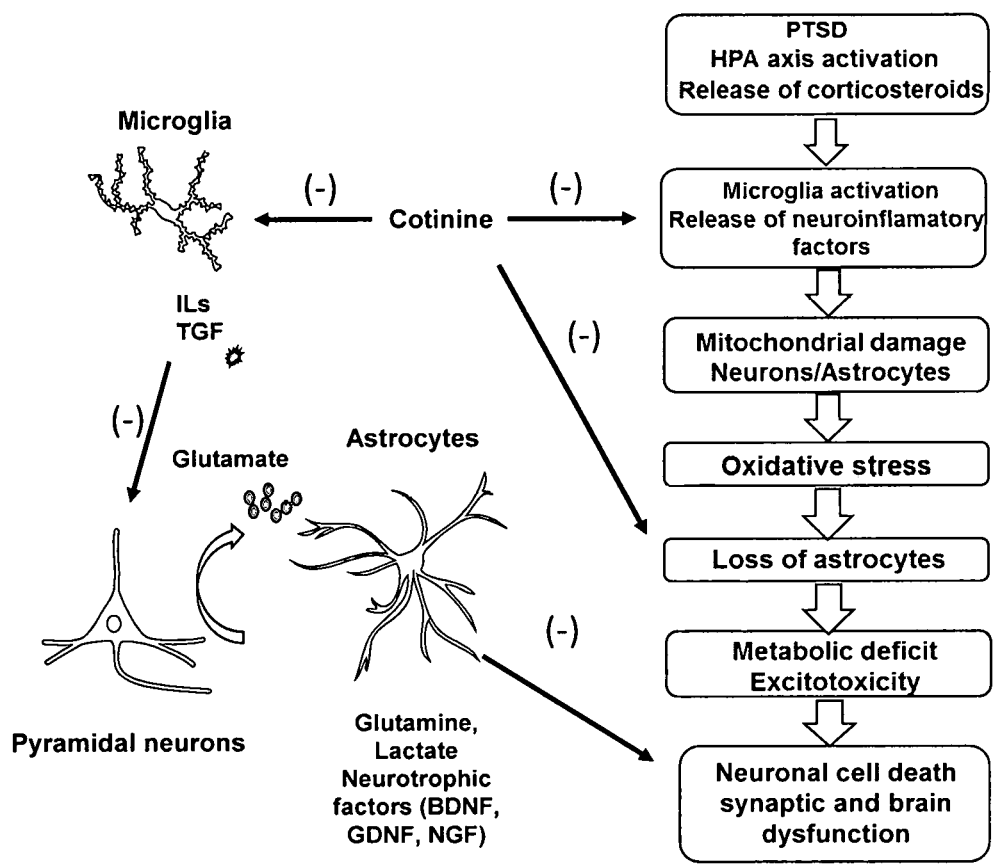
FIG. 16. Potential mechanisms of action of cotinine in reducing depressive-like behavior Microglia activation by stress is counteracted by cotinine, thus protecting GFAP+ cells from oxidative stress and apoptosis. This effect will recover the ability of astrocytes in supporting neuroplasticity by providing nutrients, energy molecules, neurotrophic factors and preventing excitotoxicity by up taking glutamate an excitatory neurotransmitter. BDNF, brain-derived neurotrophic factor; GDNF, glial derived neurotrophic factor; GLT1, glutamate transporter; HPA, hypothalamus-pituitary adrenal gland; IL, interleukins; NGF, nerve growth factor; TGF, Transforming growth factor.

Positive allosteric modulators (PAMs) of the nAChRs have been proposed as a drug with a novel approach with therapeutic possibilities for cognition, neurodegeneration and psychiatric conditions including PTSD. Unlike traditional nAChRs agonists, the PAM would enhance cholinergic function, but maintaining the natural temporal pattern of receptor stimulation, by endogenous agonists (FIG. 16).

In addition, α7nAChRs are expressed in microglia and peripheral macrophages where their activation has anti-inflammatory effects. Thus, positive modulators of these receptors such as cotinine both in microglia and neurons can reduce neuroinflammation and promote neuronal survival and synaptic plasticity, respectively.

Cotinine increased the expression of GFAP in the hippocampus and frontal cortex of mice subjected to immobilization stress, suggesting that cotinine not only can prevent the pathological cellular changes induced by stress, but it can also help to the recovery of the brain, restoring brain functions and the expression of GFAP$^+$ cells in brain regions involved in memory formation and emotional and fear responses. A previous study showed that young mice with more complex astrocyte structures perform better in the object recognition test (Diniz et al., 2016). Recently, Lee et al. investigated whether the blockade of astrocytic vesicular release induced behavioral abnormalities. They found a significant impairment in recognition memory when tested in the NOR, and the authors proposed that astrocytes are necessary for novel object recognition behavior and to maintain functional gamma oscillations both in vitro and in awake-behaving animals (Lee et al., 2014). These results are coherent with our results showing that the amelioration of astrocytes function was associated with the improvement in recognition memory in the restrained mice.

A recent report showed a marked decrease in the soma area and length of astrocytes projections and reduced arborization induced by stress using fear conditioning with electric shock (Saur et al., 2016). The authors showed in a rat model of PTSD, that in the hippocampus, stress decreased the density of GFAP$^+$ astrocytes and negatively changed its morphology, diminishing the total number of primary processes, and their arborization complexity. Stress also altered the polarity of hippocampal astrocytes. No such changes were observed in astrocytes from the amygdala. Indeed, the fact that cotinine IN is also effective in diminishing the effects of stress suggests that the effects of oral cotinine is due to its direct effect in the brain, and not the effect of one of its metabolites or derivatives.

Numerous studies show the neuroprotective effect of the positive modulators of the α7 nAChRs (Balsera et al., 2014; Barreto et al., 2017; Barreto et al., 2015; Echeverria et al., 2016b). In our view, these results represent new mechanism of action of cotinine under chronic psychological stress and support the view that a positive modulation of the neuronal nicotinic receptors has restorative effects on the brain of subject suffering from PTSD. The results of this study help clarify the potential beneficial effects of cotinine in brain repair. We believe that these results are critical to better understanding of the clinical and therapeutic effects of cotinine on people suffering from neurodegenerative diseases and PTSD-associated conditions.

Conclusions

The evidence obtained in this study permits to conclude that post-treatment with IN cotinine is effective in restoring mood equilibrium and cognitive abilities as well as astrocytes function after chronic restraint stress in mice. The preceding constitutes the first evidence about the action of cotinine on GFAP$^+$ cells. This finding represents a new mechanism of action of cotinine to restore neuronal survival and plasticity after stress. The IN delivery of cotinine proved to be effective as a method of treatment with cotinine for PTSD or restraint stress-associated disorders. It is necessary to supplement the results presented in this work with further clinical research, enabling to establish whether the observed beneficial effects of cotinine in rodents are equally effective in humans.

References for Example 2

Antunes, M., Biala, G., 2012. The novel object recognition memory: neurobiology, test procedure, and its modifications. Cogn Process 13, 93-110.

Babb, T. L., Mathern, G. W., Pretorius, J. K., Cifuentes, F., 1996. Astrocytes may contribute to the latent period in progressive neuron loss, axon sprouting, and chronic seizures in rat kainate hippocampal epilepsy. Epilepsy Res Suppl 12, 343-354.

Balsera, B., Mulet, J., Fernandez-Carvajal, A., de la Tone-Martinez, R., Ferrer-Montiel, A., Hernandez-Jimenez, J. G., Estevez-Herrera, J., Borges, R., Freitas, A. E., Lopez, M. G., Garcia-Lopez, M. T., Gonzalez-Muniz, R., Perez de Vega, M. J., Valor, L. M., Svobodova, L., Sala, S., Sala, F., Criado, M., 2014. Chalcones as positive allosteric modulators of alpha? nicotinic acetylcholine receptors: a new target for a privileged structure. Eur J Med Chem 86, 724-739.

Barreto, G. E., Avila-Rodriguez, M., Foitzick, M., Aliev, G., Echeverria, V., 2017. Advances in Medicinal Plants with Effects on Anxiety Behavior Associated to Mental and Health Conditions. Curr Med Chem 24, 411-423.

Barreto, G. E., Yarkov, A., Avila-Rodriguez, M., Aliev, G., Echeverria, V., 2015. Nicotine-Derived Compounds as Therapeutic Tools Against Post-Traumatic Stress Disorder. Curr Pharm Des 21, 3589-3595.

Benarroch, E. E., 2005. Neuron-astrocyte interactions: partnership for normal function and disease in the central nervous system. Mayo Clin Proc 80, 1326-1338.

Bencherif, M., Narla, S. T., Stachowiak, M. S., 2014. Alpha7 neuronal nicotinic receptor: a pluripotent target for diseases of the central nervous system. CNS Neurol Disord Drug Targets 13, 836-845.

Broide, R. S., Leslie, F. M., 1999. The alpha7 nicotinic acetylcholine receptor in neuronal plasticity. Mol Neurobiol 20, 1-16.

Cobb, J. A., O'Neill, K., Milner, J., Mahajan, G. J., Lawrence, T. J., May, W. L., Miguel-Hidalgo, J., Rajkowska, G., Stockmeier, C. A., 2016. Density of GFAP-immunoreactive astrocytes is decreased in left hippocampi in major depressive disorder. Neuroscience 316, 209.220.

Culquhoun, L. M., Patrick, J. W., 1997. Pharmacology of neuronal nicotinic acetylcholine receptor subtypes. Adv Pharmacol 39, 191-220.

Colvonen, P. J., Glassman, L. H., Crocker, L. D., Buttner, M. M., Orff, H., Schiehser, D. M., Norman, S. B., Afari, N., 2017. Pretreatment biomarkers predicting PTSD psychotherapy outcomes: A systematic review. Neurosci Biobehav Rev 75, 140-156.

Crotti, A., Glass, C. K., 2015. The choreography of neuroinflammation in Huntington's disease. Trends Immunol 36, 364-373.

Czeh, B., Muller-Keuker, J. I., Rygula, R., Abumaria, N., Hiemke, C., Domenici, E., Fuchs, E., 2007. Chronic social stress inhibits cell proliferation in the adult medial prefrontal cortex: hemispheric asymmetry and reversal by fluoxetine treatment. Neuropsychopharmacology 32, 1490-1503.

Czeh, B., Simon, M., Schmelting, B., Hiemke, C., Fuchs, E., 2006. Astroglial plasticity in the hippocampus is affected by chronic psychosocial stress and concomitant fluoxetine treatment. Neuropsychopharmacology 31, 1616-1626.

d'Incamps, B. L., Ascher, P., 2014. High affinity and low affinity heteromeric nicotinic acetylcholine receptors at central synapses. J Physiol 592, 4131-4136.

Day, J. R., Frank, A. T., O'Callaghan, J. P., DeHart, B. W., 1998. Effects of microgravity and bone morphogenetic protein II on GFAP in rat brain. J Appl Physiol (1985) 85, 716-722.

de Aguiar, R. B., Parfitt, G. M., Jaboinski, J., Barros, D. M., 2013. Neuroactive effects of cotinine on the hippocampus: behavioral and biochemical parameters. Neuropharmacology 71, 292-298.

Dienel, G. A., 2017. The metabolic trinity, glucose-glycogen-lactate, links astrocytes and neurons in brain energetics, signaling, memory, and gene expression. Neurosci Lett 637, 18-25.

Diniz, D. G., de Oliveira, M. A., de Lima, C. M., Foro, C. A., Sosthenes, M. C., Bento-Torres, J., da Costa Vasconcelos, P. F., Anthony, D. C., Diniz, C. W., 2016. Age, environment, object recognition and morphological diversity of GFAP-immunolabeled astrocytes. Behav Brain Funct 12, 28.

Echeverria, V., Alex Grizzell, J., Barreto, G. E., 2016a. Neuroinflammation: A Therapeutic Target of Cotinine for the Treatment of Psychiatric Disorders? Curr Pharm Des 22, 1324-1333. Echeverria, V., Yarkov, A., Aliev, G., 2016b. Positive modulators of the alpha? nicotinic receptor against neuroinflammation and cognitive impairment in Alzheimer's disease. Prog Neurobiol 144, 142-157.

Exley, K., Cragg, S. J., 2008. Presynaptic nicotinic receptors: a dynamic and diverse cholinergic filter of striatal dopamine neurotransmission. Br J Pharmacol 153 Suppl 1, S283-297.

Feng, D., Guo, B., Liu, G., Wang, B., Wang, W., Gao, G., Qin, H., Wu, S., 2015. FGF2 alleviates PTSD symptoms in rats by restoring GLAST function in astrocytes via the JAK/STAT pathway. Eur Neuropsychopharmacol 25, 1287-1299.

Ferraz, A. C., Delattre, A. M., Almendra, R. G., Sonagli, M., Borges, C., Araujo, P., Andersen, M. L., Tufik, S., Lima, M. M., 2011. Chronic omega-3 fatty acids supplementation promotes beneficial effects on anxiety, cognitive and depressive-like behaviors in rats subjected to a restraint stress protocol. Behav Brain Res 219, 116-122.

Forster, D., Reiser, G., 2016. Nucleotides protect rat brain astrocytes against hydrogen peroxide toxicity and induce antioxidant defense via P2Y receptors. Neurochem Int 94, 57-66.

Franklin, K. B. J., and Paxinos, G., 2001. The Mouse Brain in Stereotaxic Coordinates, Academic Press San Diego, Calif.

Fuchs, E., Flugge, G., Czeh, B., 2006. Remodeling of neuronal networks by stress. Front Biosci 11, 2746-2758.

Fuller, S., Steele, M., Munch, G., 2010. Activated astroglia during chronic inflammation in Alzheimer's disease—do they neglect their neurosupportive roles? Mutat Res 690, 40-49.

Gao, J., Adam, B. L., Terry, A. V., Jr., 2014. Evaluation of nicotine and cotinine analogs as potential neuroprotective agents for Alzheimer's disease. Bioorg Med Chem Lett 24, 1472-1478.

Gibbs, M. E., Anderson, D. G., Hertz, L., 2006. Inhibition of glycogenolysis in astrocytes interrupts memory consolidation in young chickens. Glia 54, 214-222.

Grayson, B., Leger, M., Piercy, C., Adamson, L., Harte, M., Neill, J. C., 2015. Assessment of disease-related cognitive impairments using the novel object recognition (NOR) task in rodents. Behav Brain Res 285, 176-193.

Grizzell, J. A., Echeverria, V., 2014. New Insights into the Mechanisms of Action of Cotinine and its Distinctive Effects from Nicotine. Neurochem Res.

Grizzell, J. A., Echeverria, V., 2015. New Insights into the Mechanisms of Action of Cotinine and its Distinctive Effects from Nicotine. Neurochem Res 40, 2032-2046.

Grizzell, J. A., Iarkov, A., Holmes, R., Mori, T., Echeverria, V., 2014a. Cotinine reduces depressive-like behavior, working memory deficits, and synaptic loss associated with chronic stress in mice. Behav Brain Res 268, 55-65.

Grizzell, J. A., Mullins, M., Iarkov, A., Rohani, A., Charry, L. C., Echeverria, V., 2014b. Cotinine reduces depressive-like behavior and hippocampal vascular endothelial growth factor downregulation after forced swim stress in mice. Behav Neurosci 128, 713-721.

Grizzell, J. A., Patel, S., Barreto, G. E., Echeverria, V., 2017. Cotinine improves visual recognition memory and decreases cortical Tau phosphorylation in the Tg6799 mice. Prog Neuropsychopharmacol Biol Psychiatry 78, 75-81.

Guo-Ross, S. X., Yang, E. Y., Walsh, T. J., Bondy, S. C., 1999. Decrease of glial fibrillary acidic protein in rat frontal cortex following aluminum treatment. J Neurochem 73, 1609-1614.

Hanson, L. R., Frey, W. H., 2nd, 2007. Strategies for intranasal delivery of therapeutics for the prevention and treatment of neuroAIDS. J Neuroimmune Pharmacol 2, 81-86.

Hanson, L. R., Frey, W. H., 2nd, 2008. Intranasal delivery bypasses the blood-brain barrier to target therapeutic agents to the central nervous system and treat neurodegenerative disease. BMC Neurosci 9 Suppl 3, S5.

Heinrichs, S. C., Leite-Morris, K. A., Rasmusson, A. M., Kaplan, G. B., 2013. Repeated valproate treatment facilitates fear extinction under specific stimulus conditions. Neurosci Lett 552, 108-113.

Hennessy, E., Griffin, E. W., Cunningham, C., 2015. Astrocytes Are Primed by Chronic Neurodegeneration to Produce Exaggerated Chemokine and Cell Infiltration Responses to Acute Stimulation with the Cytokines IL-1beta and TNF-alpha. J Neurosci 35, 8411-8422.

Hogg, S., 1996. A review of the validity and variability of the elevated plus-maze as an animal model of anxiety. Pharmacol Biochem Behav 54, 21-30.

Iarkov, A., Appunn, D., Echeverria, V., 2016. Post-treatment with cotinine improved memory and decreased depressive-like behavior after chemotherapy in rats. Cancer Chemother Pharmacol 78, 1033-1039.

Imbe, H., Kimura, A., Donishi, T., Kaneoke, Y., 2012. Chronic restraint stress decreases glial fibrillary acidic protein and glutamate transporter in the periaqueductal gray matter. Neuroscience 223, 209-218.

Jak, A. J., Crocker, L. D., Aupperle, R. L., Clausen, A., Bomyea, J., 2016. Neurocognition in PTSD: Treatment Insights and Implications. Curr Top Behav Neurosci.

Javidi, H., Yadollahie, M., 2012. Post-traumatic Stress Disorder. Int J Occup Environ Med 3, 2-9.

Kabadi, S. V., Stoica, B. A., Loane, D. J., Luo, T., Faden, A. I., 2014. CR8, a novel inhibitor of CDK, limits microglial activation, astrocytosis, neuronal loss, and neurologic dysfunction after experimental traumatic brain injury. J Cereb Blood Flow Metab 34, 502-513.

Karperien, A., Ahammer, H., Jelinek, H. F., 2013. Quantitating the subtleties of microglial morphology with fractal analysis. Front Cell Neurosci 7, 3.

Karperien, A. L., Jelinek, H. F., 2015. Fractal, multifractal, and lacunarity analysis of microglia in tissue engineering. Front Bioeng Biotechnol 3, 51.

Kim, J., Waldvogel, H. J., Faull, R. L., Curtis, M. A., Nicholson, L. F., 2015. The RAGE receptor and its ligands are highly expressed in astrocytes in a grade-dependant manner in the striatum and subependymal layer in Huntington's disease. J Neurochem 134, 927-942.

Kretzschmar, H. A., DeArmond, S. J., Forno, L. S., 1985. Measurement of GFAP in hepatic encephalopathy by ELISA and transblots. J Neuropathol Exp Neurol 44, 459-471.

Laugharne, J., Kullack, C., Lee, C. W., McGuire, T., Brockman, S., Drummond, P. D., Starkstein, S., 2016. Amygdala Volumetric Change Following Psychotherapy for Posttraumatic Stress Disorder. J Neuropsychiatry Clin Neurosci, appineuropsych16010006.

Lee, H. S., Ghetti, A., Pinto-Duarte, A., Wang, X., Dziewczapolski, G., Galimi, F., Huitron-Resendiz, S., Pina-Crespo, J. C., Roberts, A. J., Verma, I. M., Sejnowski, T. J., Heinemann, S. F., 2014. Astrocytes contribute to gamma oscillations and recognition memory. Proc Natl Acad Sci USA 111, E3343-3352.

Lee, J. L., Bertoglio, L. J., Guimaraes, F. S., Stevenson, C. W., 2017. Cannabidiol regulation of emotion and emotional memory processing: relevance for treating anxiety-related and substance abuse disorders. Br J Pharmacol.

Li, C., Zhao, R., Gao, K., Wei, Z., Yin, M. Y., Lau, L. T., Chui, D., Yu, A. C., 2011. Astrocytes: implications for neuroinflammatory pathogenesis of Alzheimer's disease. Curr Alzheimer Res 8, 67-80.

Liu, Y., Zeng, X., Hui, Y., Zhu, C., Wu, J., Taylor, D. H., Ji, J., Fan, W., Huang, Z., Hu, J., 2015. Activation of alpha7 nicotinic acetylcholine receptors protects astrocytes against oxidative stress-induced apoptosis: implications for Parkinson's disease. Neuropharmacology 91, 87-96.

Lucassen, P. J., Heine, V. M., Muller, M. B., van der Beek, E. M., Wiegant, V. M., De Kloet, E. R., Joels, M., Fuchs, E., Swaab, D. F., Czeh, B., 2006. Stress, depression and hippocampal apoptosis. CNS Neurol Disord Drug Targets 5, 531-546.

McHugh, T., Forbes, D., Bates, G., Hopwood, M., Creamer, M., 2012. Anger in PTSD: is there a need for a concept of PTSD-related posttraumatic anger? Clin Psychol Rev 32, 93-10/1.

Meng, L., Jiang, J., Jin, C., Liu, J., Zhao, Y., Wang, W., Li, K., Gong, Q., 2016. Trauma-specific Grey Matter Alterations in PTSD. Sci Rep 6, 33748.

Moller, H. J., Demyttenaere, K., Olausson, B., Szamosi, J., Wilson, E., Hosford, D., Dunbar, G., Tummala, R., Eriksson, H., 2015. Two Phase III randomised double-blind studies of fixed-dose TC-5214 (dexmecamylamine) adjunct to ongoing antidepressant therapy in patients with major depressive disorder and an inadequate response to prior antidepressant therapy. World J Biol Psychiatry 16, 483-501.

Nagai, M., Re, D. B., Nagata, T., Chalazonitis, A., Jessell, T. M., Wichterle, H., Przedborski, S., 2007. Astrocytes expressing ALS-linked mutated SOD1 release factors selectively toxic to motor neurons. Nat Neurosci 10, 615-622.

Naitoh, H., Yamaoka, K., Nomura, S., 1992. [Behavioral assessment of antidepressants (1)—The forced swimming test: a review of its theory and practical application]. Yakubutsu Seishin Kodo 12, 105-111.

Nestler, E. J., Barrot, M., DiLeone, R. J., Eisch, A. J., Gold, S. J., Monteggia, L. M., 2002. Neurobiology of depression. Neuron 34, 13-25.

Niranjan, R., 2014. The role of inflammatory and oxidative stress mechanisms in the pathogenesis of Parkinson's disease: focus on astrocytes. Mol Neurobiol 49, 28-38.

North, C. S., Suris, A. M., Smith, R. P., King, R. V., 2016. The evolution of PTSD criteria across editions of DSM. Ann Clin Psychiatry 28, 197-208.

Orlovsky, M. A., Dosenko, V. E., Spiga, F., Skibo, G. G., Lightman, S. L., 2014. Hippocampus remodeling by chronic stress accompanied by GR, proteasome and caspase-3 overexpression. Brain Res 1593, 83-94.

Otani, N., Nawashiro, H., Fukui, S., Ooigawa, H., Ohsumi, A., Toyooka, T., Shima, K., Gomi, H., Brenner, M., 2006. Enhanced hippocampal neurodegeneration after traumatic or kainate excitotoxicity in GFAP-null mice. J Clin Neurosci 13, 934-938.

Patel, S., Grizzell, J. A., Holmes, R., Zeitlin, R., Solomon, R., Sutton, T. L., Rohani, A., Charry, L. C., Iarkov, A., Mori, T., Echeverria Moran, V., 2014. Cotinine halts the advance of Alzheimer's disease-like pathology and associated depressive-like behavior in Tg6799 mice. Front Aging Neurosci 6, 162.

Perrine, S. A., Eagle, A. L., George, S. A., Mulo, K., Kohler, R. J., Gerard, J., Harutyunyan, A., Hool, S. M., Susick, L. L., Schneider, B. L., Ghoddoussi, F., Galloway, M. P., Liberzon, I., Conti, A. C., 2016. Severe, multimodal stress exposure induces PTSD-like characteristics in a mouse model of single prolonged stress. Behav Brain Res 303, 228-237.

Pichon, Y., Prime, L., Benquet, P., Tiaho, F., 2004. Some aspects of the physiological role of ion channels in the nervous system. Eur Biophys J 33, 211-226.

Radford, R. A., Morsch, M., Rayner, S. L., Cole, N. J., Pountney, D. L., Chung, R. S., 2015. The established and emerging roles of astrocytes and microglia in amyotrophic lateral sclerosis and frontotemporal dementia. Front Cell Neurosci 9, 414.

Rehani, K., Scott, D. A., Renaud, D., Hamza, H., Williams, L. R., Wang, H., Martin, M., 2008. Cotinine-induced convergence of the cholinergic and PI3 kinase-dependent anti-inflammatory pathways in innate immune cells. Biochim Biophys Acta 1783, 375-382.

Rotaru, T. S., Rusu, A., 2016. A Meta-Analysis for the Efficacy of Hypnotherapy in Alleviating PTSD Symptoms. Int J Clin Exp Hypn 64, 116-136.

Santha, P., Veszelka, S., Hoyk, Z., Meszaros, M., Walter, F. R., Toth, A. E., Kiss, L., Kincses, A., Olah, Z., Seprenyi, G., Rakhely, G., Der, A., Pakaski, M., Kalman, J., Kittel, A., Deli, M. A., 2015. Restraint Stress-Induced Morphological Changes at the Blood-Brain Barrier in Adult Rats. Front Mol Neurosci 8, 88.

Saur, L., Baptista, P. P., Bagatini, P. B., Neves, L. T., de Oliveira, R. M., Vaz, S. P., Ferreira, K., Machado, S. A., Mestriner, R. G., Xavier, L. L., 2016. Experimental Posttraumatic Stress Disorder Decreases Astrocyte Density and Changes Astrocytic Polarity in the CA1 Hippocampus of Male Rats. Neurochem Res 41, 892-904.

Schaffner, A. E., Ghesquiere, A., 2001. The effect of type 1 astrocytes on neuronal complexity: a fractal analysis. Methods 24, 323-329.

Sheynin, J., Liberzon, I., 2016. Circuit dysregulation and circuit-based treatments in posttraumatic stress disorder. Neurosci Lett.

Spence, R. D., Hamby, M. E., Umeda, E., Itoh, N., Du, S., Wisdom, A. J., Cao, Y., Bondar, G., Lam, J., Ao, Y., Sandoval, F., Suriany, S., Sofroniew, M. V., Voskuhl, R. R., 2011. Neuroprotection mediated through estrogen receptor-alpha in astrocytes. Proc Natl Acad Sci USA 108, 8867-8872.

Stander, V. A., Thomsen, C. J., Highfill-McRoy, R. M., 2014. Etiology of depression comorbidity in combat-related PTSD: a review of the literature. Clin Psychol Rev 34, 87-98.

Stobart, J. L., Anderson, C. M., 2013. Multifunctional role of astrocytes as gatekeepers of neuronal energy supply. Front Cell Neurosci 7, 38.

Szczepanik, J., Nugent, A. C., Drevets, W. C., Khanna, A., Zarate, C. A., Jr., Furey, M. L., 2016. Amygdala response to explicit sad face stimuli at baseline predicts antidepressant treatment response to scopolamine in major depressive disorder. Psychiatry Res 254, 67-73.

Terry, A. V., Jr., Callahan, P. M., Bertrand, D., 2015. R-(+) and s-(−) isomers of cotinine augment cholinergic responses in vitro and in vivo. J Pharmacol Exp Ther 352, 405-418.

Trevizol, A. P., Barros, M. D., Silva, P. O., Osuch, E., Cordeiro, Q., Shiozawa, P., 2016. Transcranial magnetic stimulation for posttraumatic stress disorder: an updated systematic review and meta-analysis. Trends Psychiatry Psychother 38, 50-55.

Ugbode, C., Hu, Y., Whalley, B., Peers, C., Rattray, M., Dallas, M. L., 2017. Astrocytic transporters in Alzheimer's disease. Biochem J 474, 333-355.

Verkhratsky, A., Rodriguez, J. J., Parpura, V., 2013. Astroglia in neurological diseases. Future Neurol 8, 149-158.

Villapol, S., Byrnes, K. R., Symes, A. J., 2014. Temporal dynamics of cerebral blood flow, cortical damage, apoptosis, astrocyte-vasculature interaction and astrogliosis in the pericontusional region after traumatic brain injury. Front Neurol 5, 82.

Wang, L., Almeida, L. E., Spornick, N. A., Kenyon, N., Kamimura, S., Khaibullina, A., Nouraie, M., Quezado, Z. M., 2015. Modulation of social deficits and repetitive behaviors in a mouse model of autism: the role of the nicotinic cholinergic system. Psychopharmacology (Berl) 232, 4303-4316.

Watanabe, Y., Gould, E., McEwen, B. S., 1992. Stress induces atrophy of apical dendrites of hippocampal CA3 pyramidal neurons. Brain Res 588, 341-345.

Webster, K. M., Sun, M., Crack, P., O'Brien, T. J., Shultz, S. R., Semple, B. D., 2017. Inflammation in epileptogenesis after traumatic brain injury. J Neuroinflammation 14, 10.

Webster, M. J., O'Grady, J., Kleinman, J. E., Weickert, C. S., 2005. Glial fibrillary acidic protein mRNA levels in the cingulate cortex of individuals with depression, bipolar disorder and schizophrenia. Neuroscience 133, 453-461.

Weinstein, D. E., Shelanski, M. L., Liem, R. K., 1991. Suppression by antisense mRNA demonstrates a requirement for the glial fibrillary acidic protein in the formation of stable astrocytic processes in response to neurons. J Cell Biol 112, 1205-1213.

Wildeboer-Andrud, K. M., Zheng, L., Choo, K. S., Stevens, K. E., 2014. Cotinine impacts sensory processing in DBA/2 mice through changes in the conditioning amplitude. Pharmacol Biochem Behav 117, 144-150.

Wilder Schaaf, K. P., Artman, L. K., Peberdy, M. A., Walker, W. C., Omato, J. P., Gossip, M. R., Kreutzer, J. S., Virginia Commonwealth University, A. I., 2013. Anxiety, depression, and PTSD following cardiac arrest: a systematic review of the literature. Resuscitation 84, 873-877.

Williams, S. G., Collen, J., On, N., Holley, A. B., Lettieri, C. J., 2015. Sleep disorders in combat-related PTSD. Sleep Breath 19, 175-182.

Winkler, E. A., Nishida, Y., Sagare, A. P., Rege, S. V., Bell, R. D., Perlmutter, D., Sengillo, J. D., Hillman, S., Kong, P., Nelson, A. R., Sullivan, J. S., Zhao, Z., Meiselman, H. J., Wenby, R. B., Soto, J., Abel, E. D., Makshanoff, J., Zuniga, E., De Vivo, D. C., Zlokovic, B. V., 2015. GLUT1 reductions exacerbate Alzheimer's disease vasculo-neuronal dysfunction and degeneration. Nat Neurosci 18, 521-530.

Xia, L., Zhai, M., Wang, L., Miao, D., Zhu, X., Wang, W., 2013. FGF2 blocks PTSD symptoms via an astrocyte-based mechanism. Behav Brain Res 256, 472-480.

Yamanaka, K., Chun, S. J., Boillee, S., Fujimori-Tonou, N., Yamashita, H., Gutmann, D. H., Takahashi, R., Misawa, H., Cleveland, D. W., 2008. Astrocytes as determinants of disease progression in inherited amyotrophic lateral sclerosis. Nat Neurosci 11, 251-253.

Yang, S. S., Huang, C. L., Chen, H. E., Tung, C. S., Shih, H. P., Liu, Y. P., 2015. Effects of SPAK knockout on sensorimotor gating, novelty exploration, and brain area-dependent expressions of NKCC1 and KCC2 in a mouse model of schizophrenia. Prog Neuropsychopharmacol Biol Psychiatry 61, 30-36.

Yoon, S., Kim, J. E., Hwang, J., Kang, I., Jeon, S., Im, J. J., Kim, B. R., Lee, S., Kim, G. H., Rhim, H., Lim, S. M., Lyoo, I. K., 2017. Recovery from Posttraumatic Stress Requires Dynamic and Sequential Shifts in Amygdalar Connectivities. Neuropsychopharmacology 42, 454-461.

Zeitlin, R., Patel, S., Solomon, R., Tran, J., Weeber, E. J., Echeverria, V., 2012. Cotinine enhances the extinction of contextual fear memory and reduces anxiety after fear conditioning. Behav Brain Res 228, 284-293.

Zhu, X., Helpman, L., Papini, S., Schneier, F., Markowitz, J. C., Van Meter, P. E., Lindquist, M. A., Wager, T. D., Neria, Y., 2016. Altered resting state functional connectivity of fear and reward circuitry in comorbid PTSD and major depression. Depress Anxiety.

Example 3

Materials and Methods
Animals

Two-month-old male C57BL/6J mice (obtained from the University of Chile), weighing 25-30 g were maintained on a 12-hours (h) light/dark cycle (light on at 07:00 h) with ad libitum access to food and water and at a regulated temperature ($25\pm1°$ C.). Upon arrival, mice were group housed and acclimated for 7 days before behavioral testing. Experiments were performed during the light period of the circadian cycle. Animal handling and care were performed according to protocols approved for the Universidad San Sebastian ethical committee and performed in compliance with the Guide for the care and use of laboratory animals adopted by the National Institute of Health (USA).

Drug Preparation

Cotinine ((5S)-1-methyl-5-(3-pyridyl) pyrrolidin-2-one) (Sigma-Aldrich Corporation, St. Louis, Mo., USA) was prepared by dissolving the powdered compound in sterile phosphate buffered saline (PBS). KO was purchased from Walgreens product KO omega-3, 300 mg capsules (Superba, USA). Soft gels contain 300 mg KO (omega-3 fatty acids 90 mg, eicosapentanoic acid 50 mg, docosahexaenoic acid 24 mg, phospholipids 130 mg).

Experimental Groups and Drug Treatments

Figure 17:
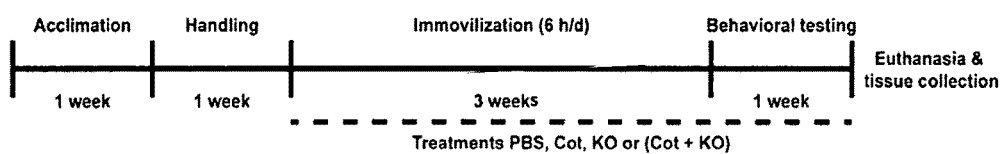
FIG. 17. Experimental design. Mice were subjected to restraint stress 6 h/day for 21 days and co-treated with PBS, krill oil (KO), Cotinine (Cot) or Cot plus KO. After restraint and under continue treatments, mice were tested for locomotor function, recognition memory using the novel object recognition test (NOR) and depressive-like behavior using the forced swim (FS) test.

Mice after acclimatization and one week of handling were randomly divided into five groups (n=8/condition) and orally treated as follow: 1) control non-restrained mice treated with vehicle (PBS, pH 7.4); 2) restrained mice treated with vehicle; 3), restrained mice treated with a cotinine solution (5 mg/kg in PBS, pH 7.4) via gavage; 4) restrained mice treated with KO (143 mg/kg); 5) restrained mice treated with cotinine plus KO solution. Mice were started with treatments, the first day of restraint and continuously until euthanasia. Treatments were administered at the same time of the day, 30 min before restraint. After 21 days into treatments, mice were behaviorally tested (FIG. 17).

Behavioral Procedures
Restraint Stress

Restraint stress (RS) was used as a model of chronic stress-induced depressive-like behavior and cognitive impairment. We used this task because is a reliable method that mimics the effects of chronic stress without causing physical pain or unnecessary discomfort to the mice [40, 41]. Mice were gently introduced into a 50-ml conical transparent plastic tubes (Corning Inc.). The tubes contain non-protruding perforations in both ends and in the walls to permit ventilation and only permitted slight movements. Mice were kept inside these tubes at 25° C., during 6 h a day for 21 days. After the daily restraint time, mice were returned to their home cages and permitted to move freely for the rest of the day. Following the three weeks of RS, mice were behaviorally tested as described below.

Open Field Test (OF)

The open field (OF) test [42] was conducted as previously described with minor modifications [43] to identify changes in locomotor activity in response to stress and/or drug treatments. Mice were individually placed in a corner and permitted to freely explore an uncovered square arena (40 cm×40 cm×35 cm) for 25 min (FIG. 18A). Total distance traveled, and time spent in the center zone were measured under moderate lighting using the video tracking software (ANY-Maze, Stoelting Co.).

Forced Swim Test

The forced swim (FS) is a broadly used task to assess depressive-like behavior in rodents [44]. The FS is performed introducing each mouse in the surface of a transparent and inescapable cylinder two-thirds filled with water at $26\pm1°$ C. (FIG. 19A). Mice engage in periods of intense movement followed for increasing periods of immobility. The immobility time during a 5-min trial is considered an expression of depressive-like behavior. Immobility time is defined as no longer exhibiting any escape behavior, motionless or moving only to keep floating. Immobility time was recorded and quantified by two investigators blind to the treatment groups.

Novel Object Recognition (NOR)

This task evaluates recognition memory and it is based on the natural preference of rodents for novel objects when exposed to new and previously encountered objects [45]. During the task, favored exploration of the novel object provides a measure of recognition memory. After a habituation step in a square arena (40 cm×40 cm×35 cm), each mouse was placed in the same arena but containing two identical transparent objects located equidistant to each other (familiarization phase) and led to explore the objects for 5 min (FIG. 20A). Then, mice were returned to their cages and permitted to rest for 30 min. After resting, mice were placed back in the arena containing one of the familiar objects and a new object (FIG. 20B). The time exploring the two objects is recorded during 5 min. Exploratory behavior was recorded and the time of exploration of each object was normalized for animal activity by calculating the exploration index (EI) that corresponds to the time spent by the mouse exploring one of the equal objects or the new object/total time spent exploring both objects×100%. The behavioral recording and analysis was performed using the (ANY-Maze, Stoelting Co.).

Morphological Analyses of Astrocytes in the Dentate Gyrus

Brain Tissue Preparation

For the protein analyses, mice were euthanized, and brains removed. Each brain was divided into two hemispheres. The left hemisphere of brains was dissected out to collect the regions of interest and quickly frozen for later analyses. For the immunohistochemistry (IHC) and fluorescent IHC (F-IHC) analysis the right hemisphere of each mouse brain was placed in 4% paraformaldehyde in PBS pH 7.4 at 4° C. for 24 h. The tissues were embedded in 2% agarose molds for vibratome sectioning. The region of interest was located using the Paxinos Atlas as a reference (Franklin and Paxinos, 2001), and serial sections of 20 μm (n≥2/mouse) were collected using the Vibratome Leica VT1000S and placed on positively charged slides (Biocare Medical, Concord, Calif.).

Immunofluorescence and Confocal Microscopy

For the F-IHC, samples were washes 3 times for 7 min with Tris-buffered saline (TBS), pH 7.8. The primary antibody anti-GFAP (1:50, BioSB) was diluted in diluent buffer, containing TBS supplemented with 1% bovine serum albumin (BSA) and 0.2% Triton X-100, and incubated with the tissue sections overnight (ON) at 4° C. After 3 washes with TBS for 10 min, sections were incubated with the secondary antibody, Cy2-conjugated rabbit anti-mouse IgG (1:200, Jackson Immuno Research, Pennsylvania, USA) diluted in TBS containing 1% BSA for 2 h at room temperature (RT). The samples were counterstained with Hoechst (1:1000) and mounted with fluorescence mounting medium (Prolong, Invitrogen). Confocal z-stacks were acquired using a LSM 780 confocal microscope (Zeiss, Oberkochen, Germany), z-stacks were normalized to maintain a consistent signal intensity through the depth of the sample, confocal z-stack image series were superposed in maximum intensity projections by ImageJ (National Institute of Health, Bethesda, Mass., USA) for the measurements.

Morphometric Analysis and Cell Counting

In each image, a region of interest (ROI) that represented the dentate gyrus was determined using free-hand drawing. For each ROI, the mean gray values (MGV), representing the area fraction with immunoreactivity for GFAP, were measured. To measure the fluorescence intensity of GFAP immunostaining in the dentate gyrus, maximum intensity projections of confocal z-stacks acquired from sagittal brain sections were converted into 8-bit greyscale images with 256 scales (pixel intensity 0 corresponding to no signal and 255 to maximal signal) by ImageJ software. To calculate the area fraction of GFAP+, binary image was converted using the threshold feature of ImageJ to keep IR area. The area of thresholded images were divided by the total area of the ROI. For the GFAP+ cell counting, cell to be counted must had at least half of the cell nucleus visible on the edge of the ROI and cells were not included in the analysis if they were adherent to blood vessel walls.

Statistical Analysis

To analyze the group and treatment effects, differences of the means between groups were analyzed using one-way analysis of variance (ANOVA), and post hoc Dunnet's test to assess difference significance between groups. Differences were considered significant with $P<0.05$.

Theory

Co-treatment with an oral formulation of cotinine plus KO during restraint stress will prevent the deficits in astrocytes in the DG of the hippocampus and this effect will also prevent the depressive-like behavior and cognitive impairment induced by chronic restraint stress.

Results

Effect of Krill Oil and Cotinine on Locomotor Activity

To determine changes in locomotor activity in the mice induced by co-treatments during immobilization stress an open field test was performed. A one-way ANOVA analysis revealed that in the restrained mice there were no statistically significant differences in distance traveled (a measure of locomotor activity) (FIG. 18B) or speed (FIG. 18C) between treatment groups. Similarly, no significant changes in locomotor activity were observed in the control non-stressed mice treatment groups (data not shown).

Effect of Krill Oil and Cotinine on Depressive-Like Behavior

To further investigate whether the anti-depressant effect of cotinine observed by pre-treatment with cotinine before restraint stress, the effect of cotinine during and after prolonged RS was measured. A two-way ANOVA analysis revealed a significant effect of chronic stress on the levels of depressive-like behavior ($F_{(1, 38)}=15.35$, $P=0.0004$) expressed as a general increase in the time spent immobile in the forced swim test by the restrained mice. Also, this analysis revealed a significant effect of treatments on depressive-like behavior ($F_{(3, 38)}=5.23$, $P=0.004$). A multiple comparison test showed no significant differences between restrained vehicle-treated mice and restrained mice treated either with cotinine ($P>0.05$) or KO ($P>0.05$) (FIG. 18). that between the mice subjected to RS, the mice co-treated with KO plus cotinine showed significantly lower levels of immobility that vehicle-treated restrained mice ($P<0.01$) (FIG. 19B).

Effect of Krill Oil and Cotinine on Recognition Memory

To determine whether the co-treatments during RS influence recognition memory mice were tested for new object preference in the novel object recognition test. Non-significant differences were found between non-stressed and restrained mice in the familiarization step of the task, with all mice explored the equal objects almost 50% of the time no showing a preference for any of the objects (FIG. 20C). However, one-way ANOVA analysis revealed significant differences between groups on recognition memory when mice were exposed to a new object in the arena ($F_{(4, 48)}=4.286$, $P=0.0049$). A multiple comparison test showed significant differences between the control non-restrained mice and the restrained mice treated with vehicle when compared to mice treated with cotinine alone ($P<0.05$) and KO alone ($P<0.01$). However, mice treated with cotinine plus KO showed non-significant differences in preference for the new object with the control non-stressed mice ($P>0.05$) (FIG. 20D).

Morphological and Cell Viability Analyses of Astrocytes

Cell Counting

Figure 21A:
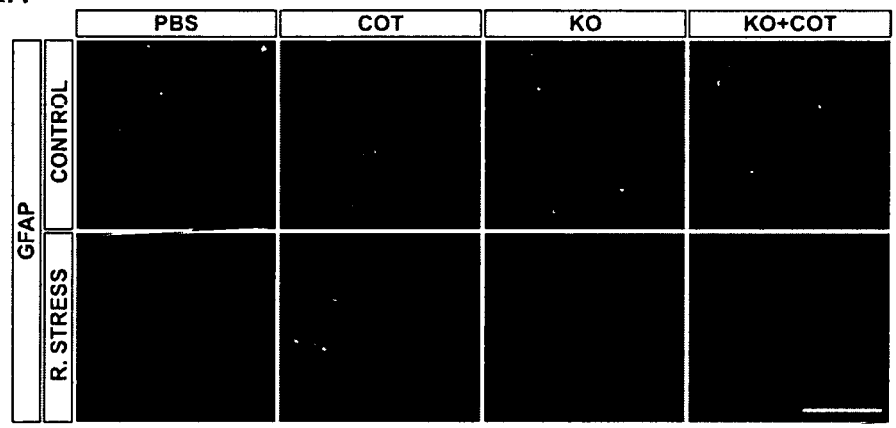
FIG. 21A-D. Analysis of the effect of cotinine plus krill oil on astrocytes in the dentate gyrus of the hippocampus. Figure representing the changes in cell GFAP+ cells numbers and morphology in the dentate gyrus region of the hippocampus in male mice subjected or not to restraint stress (R. Stress) (A). Graph depicting the changes in GFAP+ cells numbers (B); main grey values (MGV) (C); and area of immunoreactivity to GFAP (D), in the dentate gyrus of control mice or restrained (RS) mice treated with phosphate buffered saline (PBS), cotinine (Cot, 5 mg/kg) or krill oil (143 mg/kg) plus Cot (KO+Cot).
Figure 21B:
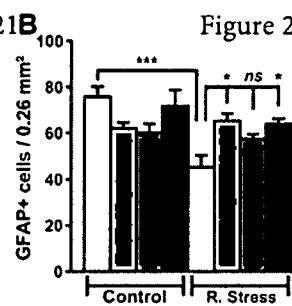

Cell count analyses of GFAP+ immunoreactivity of dentate gyrus was performed in two sections per mouse. One-way ANOVA analysis of cell counting of sections revealed significant effects of treatments on the number of GFAP+ cells in the dentate gyrus ($F_{(7, 46)}=4.883$, $P=0.0004$). A multiple comparison test revealed no significant effect of treatments between the control groups. Different results revealed the effects of treatments in the restrained mice. A significant reduction in cell density in the dentate gyrus region in the vehicle-treated restrained mice were observed when compared to control non-stressed mice ($P<0.001$). No significant effect of KO-treatment was observed on cell counting compared to vehicle-treated restrained mice. On the other hand, a significant increase of cell density was observed in the cotinine-treated and KO plus cotinine-treated restrained mice when compared to vehicle-treated restrained mice ($P<0.05$) (FIGS. 21A and B).

Mean Gray Value

Figure 21C:
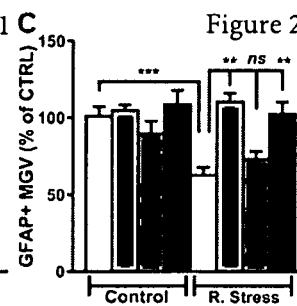

One-way ANOVA analyses of gray scale measurements were performed for GFAP+ cell in the dentate gyrus. The analysis shown significant effect of treatments in IR intensity in the dentate gyrus ($F_{(7,33)}=5.104$, $P=0.0005$). A multiple comparison test revealed no significant effect of treatments on mean gray value in the non-stressed mice. However, a significant decrease of the mean gray value intensity was found in the vehicle-treated restrained mice group when compared to vehicle treated control mice ($P<0.05$). No significant effect in IR intensity were revealed when the KO-treatment restrained mice were compared to vehicle-treated restrained mice. On the other hand, a significant increase of the IR intensity shown the cotinine-treated restrained mice when were compared to vehicle-treated restrained mice (P<0.01). Similar than the cotinine-treated mice, there was a significant increase of the IR intensity in the KO plus cotinine-treated restrained mice when were compared to vehicle-treated restrained mice (P<0.01) (FIG. 21C).

Area Fraction

Figure 21D:
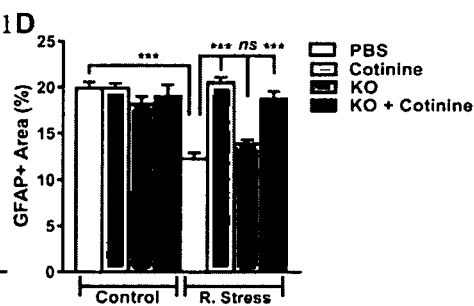

The analysis of the percent area fraction occupied by GFAP+ cells revealed significant effects of treatments in the dentate gyrus of the hippocampus (F (7, 34)=17.28, P<0.0001). A multiple comparison analysis showed that vehicle-treated restrained mice had a significant decrease of the GFAP+ area when were compared to control non-stressed and vehicle-treated mice (P<0.001). No significant changes were observed when KO-treated and restrained mice were compared to vehicle-treated restrained mice (P>0.05). Nevertheless, a significant increase in the GFAP+ fraction area was found in the cotinine-treated and KO plus cotinine-treated restrained mice in the dentate gyrus compared to vehicle-treated (P<0.001) (FIG. 21D).

Discussion

Chronic immobilization or reduced mobility stress can result from obesity, paralysis induced by vascular events such as stroke, spinal cord injury, advanced age, and many neurodegenerative conditions such as arthrosis, and ataxia. These events result in depression and cognitive impairment in the affected individuals.

RS is a broadly used model of stress-induced depressive-like behavior [46]. Prolonged RS results in morphological changes in the brain such as retraction of processes in hippocampal neurons and astrocytes [27, 47], neuroinflammation [1, 48, 49], cognitive deficits [50-54] and depressive-like behavior in rodents [46, 55]. It has been shown that cotinine administered before and after RS, reduces depressive-like behavior, synaptic deficits, astrocyte alterations and cognitive impairment compared to vehicle-treated mice [39, 56, 57]. In this study, we aimed to investigate the effect of co-treatment with cotinine alone or combined with KO, during and after chronic RS, on the development of depressive-like behavior and cognitive impairment induced by chronic stress in mice. RS provoked a decrease in recognition memory and depressive-like behavior in the mice, however, the combination of cotinine plus KO prevented the decrease in escape-oriented behavior in the forced swim test, and the loss of recognition memory in the novel recognition memory task. These results suggest that the mix potentiate the beneficial effects of both individual components in preserving mood stability and cognitive abilities under conditions of chronic immobilization stress.

It is well established that chronic stress induces a deficit in glutamatergic neurotransmission by mechanisms involving a decrease of NMDA (N-Methyl-D-aspartate) and AMPA (α-amino-3-hydroxy-5-methyl-4-isoxazolepropionic acid) receptors in the postsynaptic site in the prefrontal cortex and the hippocampus, two brain regions that are fundamental for mediating declarative and working memory abilities. This reduction in the number of synaptic glutamate receptors induces a decrease in the activity of brain networks controlling stress behavior including the prefrontal cortex-amygdala and prefrontal cortex-hippocampus pathways. Some evidence suggests that loss of glutamate receptors in neurons of the prefrontal cortex after repeated stress in rats, it is due to increased ubiquitin-proteasome-dependent degradation of these receptors [58, 59]. Previous studies, using rodent models of chronic stress, found a reduced proliferation of glial progenitor cells, and a decrease of GFAP+ cells in several brain regions, including the hippocampus and prefrontal cortex in rats. In rats, glucocorticoids can diminish the expression of GFAP in the PFC, resulting in >20% reduction in GFAP expression that was accompanied by a decrease of the GFAP mRNA [60]. In addition, chronic RS inhibits the glutamate uptake by astrocytes enhancing excitotoxicity and long-term depression [61]. Furthermore, some evidence show that rats exposed to early life stress have a decrease in astrocytes levels in the frontal cortex in adulthood, indicating a long-term effect of stress on glial cells development [62]. It is reasonable to propose that a deficit in astrocyte's function plays a role in the higher susceptibility to PTSD in persons with previous history of child abuse.

We have previously found a protective effect of cotinine administered alone via intranasal, against astrocytes decrease induced by RS. In this study, we found that co-treatment of mice with cotinine plus KO prevented the decrease in the number and complexity of astrocytes in the hippocampus of mice subjected to RS. In this study, we observed a beneficial effect of cotinine in and cotinine plus KO but not KO alone in preserving the number and arbor complexity of astrocytes under conditions of RS.

We have previously shown that in the absence of stress, long-term cotinine treatment for up to eight months did not induce significant differences in sensory motor abilities or anxiety in mice [63]. Like these results, no significant changes in locomotor activity in the mice treated with cotinine, KO or cotinine plus KO and subjected to RS were found. Thus, the superior effect of the combination of cotinine plus KO increasing the escape-oriented behavior in the FS test, cannot be explained by an increase in locomotor activity induced by the mix.

It is appealing that comparable results were obtained in the behavioral parameters tested, with a more significant effect of the mix cotinine plus KO than the individual components in the mix. The connection between changes in astrocytes and depressive-like behavior has been reported before. For example, a previous study reported that the diminution of astrocytes in the frontal cortex by using L-alpha-aminoadipic acid induced depressive-like behavior in rodents [64]. This evidence demonstrated that astroglia ablation in the PFC is sufficient to prompt depressive-like behaviors like the one induced by chronic stress. This data strongly suggests that loss of astroglia may be a key factor contributing to the development of long-lasting depression [64].

The effect of cotinine in the mix preventing the effect of stress on mood can be the result of the action of cotinine as an anti-inflammatory compound inhibiting microgliosis and neuroinflammation as well as promoting neuronal and astrocyte survival throughout the activation of pro-survival cell signaling pathways.

Figure 22:
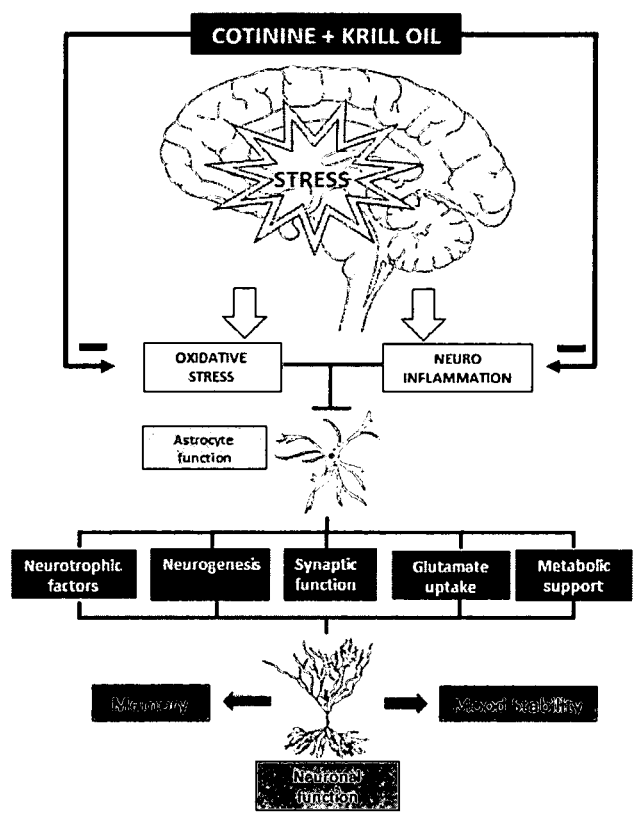
FIG. 22. Diagram representing the effect of cotinine and krill oil preventing the effects of chronic stress on astrocyte and neuronal function and behavior. The mix cotinine plus KO may counteract the neuroinflammatory and oxidative processes triggered by chronic stress in the brain. This protection may prevent the astrocyte reduction in numbers and functions including the support of neuronal plasticity including neurogenesis and that is required for memory and mood stability.

Increased levels of astrocytes will provide neurons with more energy substrates, glutamate precursors and neurotrophic factors. In addition, astrocytes can decrease the toxic effect of the abnormal increase in glutamate release induced by corticosteroids at the presynaptic level, by uptaking the glutamate from the synaptic space. On the other hand, KO components such as omega-3 and Astaxanthin can prevent oxidative stress and diminish the deleterious effects of stress on brain function [65, 66](FIG. 22).

Conclusions

In this work it was investigated whether the mix cotinine plus KO administered as an oral formulation could be useful to prevent the cognitive and affect disturbances induced by chronic restraint stress. The results show that the mix at the doses tested, prevented the depressive-like behavior, memory impairment and astrocytes disturbances induced by RS and suggests that this formulation may be useful in people and animals subjected to restraint stress due to aging and pathological and traumatic conditions.

References for Example 3

[1] M. E. Bauer, P. Perks, S. L. Lightman, N. Shanks, Restraint stress is associated with changes in glucocorticoid immunoregulation, Physiol Behav, 73 (2001) 525-532.
[2] T. Hayase, Depression-related anhedonic behaviors caused by immobilization stress: a comparison with nicotine-induced depression-like behavioral alterations and effects of nicotine and/or "antidepressant" drugs, J Toxicol Sci, 36 (2011) 31-41.
[3] R. Admon, D. Leykin, G. Lubin, V. Engert, J. Andrews, J. Pruessner, T. Hendler, Stress-induced reduction in hippocampal volume and connectivity with the ventromedial prefrontal cortex are related to maladaptive responses to stressful military service, Hum Brain Mapp, 34 (2013) 2808-2816.
[4] F. Ahmed-Leitao, G. Spies, L. van den Heuvel, S. Seedat, Hippocampal and amygdala volumes in adults with posttraumatic stress disorder secondary to childhood abuse or maltreatment: A systematic review, Psychiatry Res, 256 (2016) 33-43.
[5] B. A. Apfel, J. Ross, J. Hlavin, D. J. Meyerhoff, T. J. Metzler, C. R. Marmar, M. W. Weiner, N. Schuff, T. C. Neylan, Hippocampal volume differences in Gulf War veterans with current versus lifetime posttraumatic stress disorder symptoms, Biol Psychiatry, 69 (2011) 541-548.
[6] O. Bonne, D. Brandes, A. Gilboa, J. M. Gomori, M. E. Shenton, R. K. Pitman, A. Y. Shalev, Longitudinal MRI study of hippocampal volume in trauma survivors with PTSD, Am J Psychiatry, 158 (2001) 1248-1251.
[7] B. Czeh, T. Michaelis, T. Watanabe, J. Frahm, G. de Biurrun, M. van Kampen, A. Bartolomucci, E. Fuchs, Stress-induced changes in cerebral metabolites, hippocampal volume, and cell proliferation are prevented by antidepressant treatment with tianeptine, Proc Natl Acad Sci USA, 98 (2001) 12796-12801.
[8] W. C. Drevets, J. L. Price, M. L. Furey, Brain structural and functional abnormalities in mood disorders: implications for neurocircuitry models of depression, Brain Struct Funct, 213 (2008) 93-118.
[9] M. H. Teicher, C. M. Anderson, A. Polcari, Childhood maltreatment is associated with reduced volume in the hippocampal subfields CA3, dentate gyrus, and subiculum, Proc Natl Acad Sci USA, 109 (2012) E563-572.
[10] A. S. Gonul, O. Kitis, M. C. Eker, O. D. Eker, E. Ozan, K. Coburn, Association of the brain-derived neurotrophic factor Val66Met polymorphism with hippocampus volumes in drug-free depressed patients, World J Biol Psychiatry, 12 (2011) 110-118.
[11] B. R. Filipovic, B. Djurovic, S. Marinkovic, L. Stijak, M. Aksic, V. Nikolic, A. Starcevic, V. Radonjic, Volume changes of corpus striatum, thalamus, hippocampus and lateral ventricles in posttraumatic stress disorder (PTSD) patients suffering from headaches and without therapy, Cent Eur Neurosurg, 72 (2011) 133-137.
[12] K. Felmingham, L. M. Williams, T. J. Whitford, E. Falconer, A. H. Kemp, A. Peduto, R. A. Bryant, Duration of posttraumatic stress disorder predicts hippocampal grey matter loss, Neuroreport, 20 (2009) 1402-1406.
[13] G. Villarreal, D. A. Hamilton, H. Petropoulos, I. Driscoll, L. M. Rowland, J. A. Griego, P. W. Kodituwakku, B. L. Hart, R. Escalona, W. M. Brooks, Reduced hippocampal volume and total white matter volume in posttraumatic stress disorder, Biol Psychiatry, 52 (2002) 119-125.
[14] C. Schmitz, M. E. Rhodes, M. Bludau, S. Kaplan, P. Ong, I. Ueffing, J. Vehoff, H. Korr, C. A. Frye, Depression: reduced number of granule cells in the hippocampus of female, but not male, rats due to prenatal restraint stress, Mol Psychiatry, 7 (2002) 810-813.
[15] Y. I. Sheline, 3D MRI studies of neuroanatomic changes in unipolar major depression: the role of stress and medical comorbidity, Biol Psychiatry, 48 (2000) 791-800.
[16] P. S. Moreira, P. R. Almeida, H. Leite-Almeida, N. Sousa, P. Costa, Impact of Chronic Stress Protocols in Learning and Memory in Rodents: Systematic Review and Meta-Analysis, PLoS One, 11 (2016) e0163245.
[17] V. Luine, Estradiol: Mediator of memories, spine density and cognitive resilience to stress in female rodents, The Journal of steroid biochemistry and molecular biology, 160 (2016) 189-195.
[18] C. D. Conrad, H. A. Bimonte-Nelson, Impact of the hypothalamic-pituitary-adrenal/gonadal axes on trajectory of age-related cognitive decline, Prog Brain Res, 182 (2010) 31-76.
[19] G. E. Tafet, R. Bernardini, Psychoneuroendocrinological links between chronic stress and depression, Prog Neuropsychopharmacol Biol Psychiatry, 27 (2003) 893-903.
[20] L. P. Reagan, C. A. Grillo, G. G. Piroli, The As and Ds of stress: metabolic, morphological and behavioral consequences, Eur J Pharmacol, 585 (2008) 64-75.
[21] H. E. Scharfman, N. J. MacLusky, Differential regulation of BDNF, synaptic plasticity and sprouting in the hippocampal mossy fiber pathway of male and female rats, Neuropharmacology, 76 Pt C (2014) 696-708.
[22] M. R. Bennett, J. Lagopoulos, Stress and trauma: BDNF control of dendritic-spine formation and regression, Prog Neurobiol, 112 (2014) 80-99.
[23] M. S. Kassem, J. Lagopoulos, T. Stait-Gardner, W. S. Price, T. W. Chohan, J. C. Arnold, S. N. Hatton, M. R. Bennett, Stress-induced grey matter loss determined by MRI is primarily due to loss of dendrites and their synapses, Mol Neurobiol, 47 (2013) 645-661.
[24] R. E. Bowman, D. Ferguson, V. N. Luine, Effects of chronic restraint stress and estradiol on open field activity, spatial memory, and monoaminergic neurotransmitters in ovariectomized rats, Neuroscience, 113 (2002) 401-410.
[25] J. K. Kleen, M. T. Sitomer, P. R. Killeen, C. D. Conrad, Chronic stress impairs spatial memory and motivation for reward without disrupting motor ability and motivation to explore, Behav Neurosci, 120 (2006) 842-851.
[26] C. Pavlides, L. G. Nivon, B. S. McEwen, Effects of chronic stress on hippocampal long-term potentiation, Hippocampus, 12 (2002) 245-257.
[27] B. S. McEwen, C. D. Conrad, Y. Kuroda, M. Frankfurt, A. M. Magarinos, C. McKittrick, Prevention of stress-induced morphological and cognitive consequences, Eur Neuropsychopharmacol, 7 Suppl 3 (1997) S323-328.
[28] A. M. Magarinos, C. J. Li, J. Gal Toth, K. G. Bath, D. Jing, F. S. Lee, B. S. McEwen, Effect of brain-derived neurotrophic factor haploinsufficiency on stress-induced remodeling of hippocampal neurons, Hippocampus, 21 (2011) 253-264.

[29] J. L. Stobart, C. M. Anderson, Multifunctional role of astrocytes as gatekeepers of neuronal energy supply, Front Cell Neurosci, 7 (2013) 38.

[30] A. Schousboe, N. Westergaard, U. Sonnewald, S. B. Petersen, A. C. Yu, L. Hertz, Regulatory role of astrocytes for neuronal biosynthesis and homeostasis of glutamate and GABA, Prog Brain Res, 94 (1992) 199-211.

[31] P. G. Haydon, M. Nedergaard, How do astrocytes participate in neural plasticity?, Cold Spring Harb Perspect Biol, 7 (2014) a020438.

[32] Y. Bernardinelli, D. Muller, I. Nikonenko, Astrocyte-synapse structural plasticity, Neural Plast, 2014 (2014) 232105.

[33] S. D. Honsek, C. Walz, K. W. Kafitz, C. R. Rose, Astrocyte calcium signals at Schaffer collateral to CA1 pyramidal cell synapses correlate with the number of activated synapses but not with synaptic strength, Hippocampus, 22 (2012) 29-42.

[34] D. Garzon, R. Cabezas, N. Vega, M. Avila-Rodriguez, J. Gonzalez, R. M. Gomez, V. Echeverria, G. Aliev, G. E. Barreto, Novel Approaches in Astrocyte Protection: from Experimental Methods to Computational Approaches, J Mol Neurosci, 58 (2016) 483-492.

[35] Y. Gonzalez-Giraldo, L. M. Garcia-Segura, V. Echeverria, G. E. Barreto, Tibolone Preserves Mitochondrial Functionality and Cell Morphology in Astrocytic Cells Treated with Palmitic Acid, Mol Neurobiol, DOI 10.1007/s12035-017-0667-3(2017).

[36] M. V. Sofroniew, H. V. Vinters, Astrocytes: biology and pathology, Acta Neuropathol, 119 (2010) 7-35.

[37] L. de Filippis, Neural stem cell-mediated therapy for rare brain diseases: perspectives in the near future for LSDs and MNDs, Histol Histopathol, 26 (2011) 1093-1109.

[38] L. Saur, P. P. Baptista, P. B. Bagatini, L. T. Neves, R. M. de Oliveira, S. P. Vaz, K. Ferreira, S. A. Machado, R. G. Mestriner, L. L. Xavier, Experimental Post-traumatic Stress Disorder Decreases Astrocyte Density and Changes Astrocytic Polarity in the CA1 Hippocampus of Male Rats, Neurochem Res, 41 (2016) 892-904.

[39] N. Perez-Urrutia, C. Mendoza, N. Alvarez-Ricartes, P. Oliveros-Matus, F. Echeverria, J. A. Grizzell, G. E. Barreto, A. Iarkov, V. Echeverria, Intranasal cotinine improves memory, and reduces depressive-like behavior, and GFAP+ cells loss induced by restraint stress in mice, Exp Neurol, 295 (2017) 211-221.

[40] A. S. Jaggi, N. Bhatia, N. Kumar, N. Singh, P. Anand, R. Dhawan, A review on animal models for screening potential anti-stress agents, Neurol Sci, 32 (2011) 993-1005.

[41] W. P. Pare, G. B. Glavin, Restraint stress in biomedical research: a review, Neurosci Biobehav Rev, 10 (1986) 339-370.

[42] C. Belzung, G. Griebel, Measuring normal and pathological anxiety-like behaviour in mice: a review, Behav Brain Res, 125 (2001) 141-149.

[43] M. Norcross, P. Mathur, A. J. Enoch, R. M. Karlsson, J. L. Brigman, H. A. Cameron, J. Harvey-White, A. Holmes, Effects of adolescent fluoxetine treatment on fear-, anxiety- or stress-related behaviors in C57BL/6J or BALB/cJ mice, Psychopharmacology (Berl), 200 (2008) 413-424.

[44] C. Dalla, P. M. Pitychoutis, N. Kokras, Z. Papadopoulou-Daifoti, Sex differences in animal models of depression and antidepressant response, Basic Clin Pharmacol Toxicol, 106 (2010) 226-233.

[45] N. de Bruin, B. Pouzet, Beneficial effects of galantamine on performance in the object recognition task in Swiss mice: deficits induced by scopolamine and by prolonging the retention interval, Pharmacol Biochem Behav, 85 (2006) 253-260.

[46] T. Buynitsky, D. I. Mostofsky, Restraint stress in biobehavioral research: Recent developments, Neurosci Biobehav Rev, 33 (2009) 1089-1098.

[47] A. M. Magarinos, J. M. Verdugo, B. S. McEwen, Chronic stress alters synaptic terminal structure in hippocampus, Proc Natl Acad Sci USA, 94 (1997) 14002-14008.

[48] S. D. Tymen, I. G. Rojas, X. Zhou, Z. J. Fang, Y. Zhao, P. T. Marucha, Restraint stress alters neutrophil and macrophage phenotypes during wound healing, Brain Behav Immun, DOI.

[49] J. S. de Andrade, R. O. Abrao, I. C. Cespedes, M. C. Garcia, J. O. Nascimento, R. C. Spadari-Bratfisch, L. L. Melo, R. C. da Silva, M. B. Viana, Acute restraint differently alters defensive responses and fos immunoreactivity in the rat brain, Behav Brain Res, 232 (2012) 20-29.

[50] A. Mika, G. J. Mazur, A. N. Hoffman, J. S. Talboom, H. A. Bimonte-Nelson, F. Sanabria, C. D. Conrad, Chronic Stress Impairs Prefrontal Cortex-Dependent Response Inhibition and Spatial Working Memory, Behav Neurosci, DOI (2012).

[51] A. Thorsell, M. Michalkiewicz, Y. Dumont, R. Quirion, L. Caberlotto, R. Rimondini, A. A. Mathe, M. Heilig, Behavioral insensitivity to restraint stress, absent fear suppression of behavior and impaired spatial learning in transgenic rats with hippocampal neuropeptide Y overexpression, Proc Natl Acad Sci USA, 97 (2000) 12852-12857.

[52] I. Abidin, P. Yargicoglu, A. Agar, S. Gumuslu, S. Aydin, O. Ozturk, E. Sahin, The effect of chronic restraint stress on spatial learning and memory: relation to oxidant stress, Int J Neurosci, 114 (2004) 683-699.

[53] C. D. Conrad, J. L. Jackson, L. Wieczorek, S. E. Baran, J. S. Harman, R. L. Wright, D. L. Korol, Acute stress impairs spatial memory in male but not female rats: influence of estrous cycle, Pharmacol Biochem Behav, 78 (2004) 569-579.

[54] S. B. Cherian, K. L. Bairy, M. S. Rao, Chronic prenatal restraint stress induced memory impairment in passive avoidance task in post weaned male and female Wistar rats, Indian J Exp Biol, 47 (2009) 893-899.

[55] S. Chiba, T. Numakawa, M. Ninomiya, M. C. Richards, C. Wakabayashi, H. Kunugi, Chronic restraint stress causes anxiety- and depression-like behaviors, downregulates glucocorticoid receptor expression, and attenuates glutamate release induced by brain-derived neurotrophic factor in the prefrontal cortex, Prog Neuropsychopharmacol Biol Psychiatry, 39 (2012) 112-119.

[56] J. A. Grizzell, V. Echeverria, New Insights into the Mechanisms of Action of Cotinine and its Distinctive Effects from Nicotine, Neurochem Res, 40 (2015) 2032-2046.

[57] J. A. Grizzell, A. Iarkov, R. Holmes, T. Mori, V. Echeverria, Cotinine reduces depressive-like behavior, working memory deficits, and synaptic loss associated with chronic stress in mice, Behav Brain Res, 268 (2014) 55-65.

[58] E. Y. Yuen, J. Wei, W. Liu, P. Zhong, X. Li, Z. Yan, Repeated stress causes cognitive impairment by suppressing glutamate receptor expression and function in prefrontal cortex, Neuron, 73 (2012) 962-977.

[59] M. Joels, H. Karst, D. Alfarez, V. M. Heine, Y. Qin, E. van Riel, M. Verkuyl, P. J. Lucassen, H. J. Krugers, Effects of chronic stress on structure and cell function in rat hippocampus and hypothalamus, Stress, 7 (2004) 221-231.

[60] J. Zschocke, N. Bayatti, A. M. Clement, H. Witan, M. Figiel, J. Engele, C. Behl, Differential promotion of glutamate transporter expression and function by glucocorticoids in astrocytes from various brain regions, J Biol Chem, 280 (2005) 34924-34932.

[61] C. H. Yang, C. C. Huang, K. S. Hsu, Behavioral stress enhances hippocampal CA1 long-term depression through the blockade of the glutamate uptake, J Neurosci, 25 (2005) 4288-4293.

[62] M. Leventopoulos, D. Ruedi-Bettschen, I. Knuesel, J. Feldon, C. R. Pryce, J. Opacka-Juffry, Long-term effects of early life deprivation on brain glia in Fischer rats, Brain Res, 1142 (2007) 119-126.

[63] R. Zeitlin, S. Patel, R. Solomon, J. Tran, E. J. Weeber, V. Echeverria, Cotinine enhances the extinction of contextual fear memory and reduces anxiety after fear conditioning, Behav Brain Res, 228 (2012) 284-293.

[64] Y. Lee, H. Son, G. Kim, S. Kim, D. H. Lee, G. S. Roh, S. S. Kang, G. J. Cho, W. S. Choi, H. J. Kim, Glutamine deficiency in the prefrontal cortex increases depressive-like behaviours in male mice, J Psychiatry Neurosci, 38 (2013) 183-191.

[65] M. P. Barros, S. C. Poppe, E. F. Bondan, Neuroprotective properties of the marine carotenoid astaxanthin and omega-3 fatty acids, and perspectives for the natural combination of both in krill oil, Nutrients, 6 (2014) 1293-1317.

[66] T. G. Polotow, S. C. Poppe, C. V. Vardaris, D. Ganini, M. Guariroba, R. Maffei, E. Hatanaka, M. F. Martins, E. F. Bondan, M. P. Barros, Redox Status and Neuro Inflammation Indexes in Cerebellum and Motor Cortex of Wistar Rats Supplemented with Natural Sources of Omega-3 Fatty Acids and Astaxanthin: Fish Oil, Krill Oil, and Algal Biomass, Mar Drugs, 13 (2015) 6117-6137.

Example 4

Materials and Methods
Drugs

Cotinine (5S-1-methyl-5-(3-pyridyl) pyrrolidine-2-ona) was obtained from Sigma-Aldrich (Saint Louis, Mo.). Sertraline hydrochloride (1S,4S)-4-(3, 4-dichlorophenyl)-1,2,3, 4-tetrahydro-N-methyl-1-naphthalenamine hydrochloride), was obtained from Sigma-Aldrich. 300 mg soft gels capsules of krill oil omega-3, were purchased from Walgreens (Superba, USA). Capsules contained in 300 mg krill oil (90 mg omega-3 fatty acids, 50 mg EPA, 24 mg DHA (docosahexaenoic acid), 130 mg Phospholipids).

Animals

Mice C57BL/6 were obtained from the University of Chile (Santiago, Chile) and maintained on a 12 h light-dark cycle with ad libitum access to food and water. Mice were maintained grouped (2-3 mice by cage) in a controlled environment with average temperatures between 21-23° C. and 50-70% humidity. Mice were kept according to the mandate of the Guide of Animal care and use of laboratory animals of the National Institute of Health (NIH publication 80-23/96). All efforts were made to minimize animal suffering and to reduce the number of animals used. Protocols were performed with the approval of the Institutional animal care and use committees of the University of San Sebastián, Chile.

Experimental Design

Figure 23:
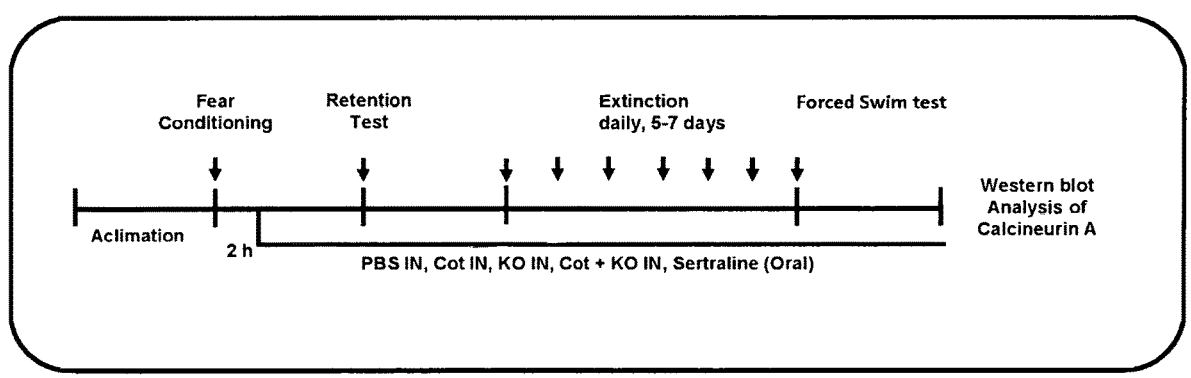
FIG. 23. Diagram representing the experimental design. Male mice (n=5-8/condition) were housed and habituated to their cages before FC. After this period mice were fear conditioned, treated, behaviorally tested for fear retention and extinction, and depressive-like behavior and euthanized. Calcineurin analysis was then performed in hippocampal extracts of mice by Western blot.

This study investigated the effect of intranasal cotinine formulations, krill oil and oral sertraline on depressive-like behavior, fear consolidation and extinction as well as the expression of calcineurin A in the hippocampus of mice (FIG. 23).

Drug Treatments

Three-month-old mice (n=5-6/condition) were weighed and assigned to treatment groups. Mice were treated with vehicle or drugs, starting two h after fear conditioning and daily after behavioral testing until euthanasia. Mice received daily treatments with 1. PBS (phosphate buffer saline, pH 7.4) via intranasal; 2. Cotinine (10 mg/ml) dissolved in PBS via intranasal (IN Cot, 24 µl); 3. Krill oil dissolved in PBS, via intranasal (48 mg/ml, 24 µl); 4. Cotinine (10 mg/ml) plus krill oil dissolved in PBS, via intranasal (48 mg/ml, 24 µl); 5. Sertraline, via oral in PBS (3 mg/kg, 50 µl). The dose of sertraline was chosen to be equivalent to a 200 mg/day in humans. The dose of cotinine was ten times lower than the dose of oral cotinine promoting fear extinction in C57BL/6 mice.

Intranasal Delivery

The intranasal delivery was performed according to the protocol of awaken intranasal drug delivery [95]. First mice were subjected to simulated delivery for one week before treatments to reduce the stress due to the procedure.

For intranasal delivery, mice were hand-restrained, placed in a supine position, and given two 12 µl drops of cotinine solutions, or PBS, into both nares consecutively. Mice were given an extra 12 µl treatment drop if the subject forcibly ejected or sneezed out the solution. Mice were held supine for 5-10 seconds after delivery to ensure that all fluid was inhaled. These volumes have shown to deliver drugs mostly to the brain without passage to the pulmonary regions [95].

Behavioral Analysis

Mice were conditioned and, subjected to fear retention test and extinction trials until extinction was attained. After extinction, mice were tested for depressive-like behavior, using the forced swim test.

Fear Conditioning

Contextual fear conditioning was performed as described [18]. The conditioning chamber used (33 cm×20 cm×22 cm) is surrounded by a sound-attenuating box with a camera connected to freeze frame software (MED Associates Inc.) and equipped to provide a background white noise (72 dB). The conditioning chamber contains in one side a speaker and in the opposite side has a 24V light, and a 36-bar insulated shock grid floor. To perform this test, each mouse was placed in the conditioning chamber for 2 min before the onset of a discrete tone (a sound that will last 30 seconds (sec) at 2,800 Hz and 85 dB). In the last two seconds of this tone, mice received a foot shock of 1 mA, kept in the conditioning chamber for 2 min and returned to their home cages. Between trials, the chamber was sanitized with 70% ethanol and dried. Freezing behavior was defined as the absence of all movement except the one needed for breathing was assessed using the FreezeView Software (MED Associates Inc.).

Fear Retention and Extinction Tests

Fear retention and extinction experiments were performed as described [18], using the same cohorts of mice and reproduced in two separate experiments. To assess fear retention and mice underwent re-exposure to the conditioning chamber in the absence of an unconditioned stimulus (shock or auditory cues) for 3 minutes (min) in daily extinction trials. Freezing behavior was measured using the ANY-Maze® software (Stoelting CO, USA). The extinction trials were continued until the decrease in freezing behavior reached a stable level.

Forced Swim Test (FS)

The forced swim test is broadly used to assess depressive-like behavior [96.97]. Each mouse was placed in a transparent cylinder (60 cm×20 cm) filled with water at 25° C. for 5 min. Two investigators blind to all treatment levels scored immobility during the complete time of the assay. A mouse was considered immobile when it remained floating motionless or moved only that which was necessary to keep its head above the water. The time immobile is considered a measure of depressive-like behavior in rodents and antidepressants decrease the time of immobility in this test [96.97].

Western Blot Analysis

After the behavioral testing, mice from all treatment groups were euthanized via cervical dislocation by a well-trained investigator. Brain regions of interest were dissected and stored at −20° C. for protein analyses. Each brain was divided into two parts, left and right hemispheres. The frontal cortex and hippocampus were dissected from left hemisphere on ice and disrupted by sonication in cold cell lysis buffer containing phosphatase and protein inhibitors (Cell Signaling Technology, Danver, Mass., USA), 1 mM PMSF (Sigma-Aldrich Corporation, St. Louis, Mo., USA). After sonication, brain extracts were incubated on ice for 30 min and centrifuged at 20,000×g for 30 min at 4° C. The protein concentration of the supernatants was measured using the Bio-Rad protein assay (Bio-Rad, Hercules, Calif., USA). Equal amounts of protein were separated by gradient 4-20% SDS-PAGE then transferred to nitrocellulose membranes (BA83 0.2 μm; Bio-Rad). The membranes were blocked in Tris-buffered saline (TBS) with 0.05% Tween 20 (TBST) containing 10% dry skim milk for 45 min. Membranes were incubated with primary antibodies in TBST overnight at 4° C., and with secondary antibodies for 1-3 h at RT in blocking buffer. A rabbit polyclonal antibody directed against calcineurin (PP2B), was obtained from Cell Signaling Technology. A monoclonal antibody directed against total Akt (Cell Signaling) was used to control protein sample loading and transfer efficiency. Membranes were washed with TBST and incubated with HRP-conjugated secondary antibodies (Bio-Rad) for 1 h at RT, washed with TBST and TBS, and images were acquired using My ECL imaging system and analyzed using the NIH Image J software.

Statistical Analysis

All values expressed as mean±standard error of the mean. The behavioral and immunoreactivity differences between sample and treatment groups were determined by One-way or two-way analysis of variance (ANOVA) with Post hoc Tukey analysis. $p<0.05$ was considered as statistically significant. All statistical analyses were performed with the software GraphPad Prism 6 (GraphPad Software Inc., San Diego, Calif., USA)

Results

Figure 24:
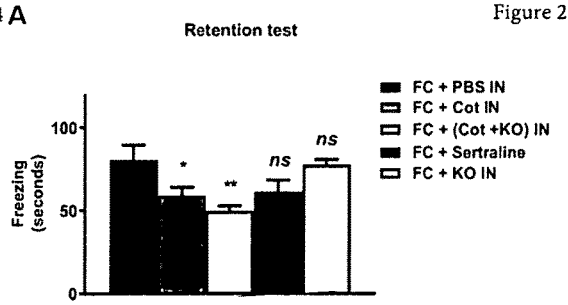
FIG. 24A-D. Effect of early Posttreatment with cotinine, sertraline and krill oil on the retention and extinction of fear memory. Two hours after fear conditioning (FC) mice (n=5-8 mice/group) received intranasal (IN) PBS, krill oil (KO), (IN) Cotinine (Cot) IN or Cot+KO IN, oral sertraline (2 mg/day). next day after, mice were and tested for contextual fear memory (retention test) and subjected to daily trials of fear extinction until a minimum and stable freezing behavior was reached. The graphs depict the freezing behavior during the retention test (A), and during the extinction trials in mice treated with PBS IN, Cot IN, KO IN (B); PBS IN, Cot IN, Cot+KO (C); and PBS IN, Cot IN, oral sertraline (D). Data was analyzed using one-way ANOVA and tukey Post hoc test. ns, non-significant change; *, $p<0.05$; **, $p<0.01$.

Effect of the Combination of Cotinine and Krill Oil on Fear Retention after Fear Conditioning Fear conditioning (FC) was used to assess the effect of post-treatment with IN cotinine on fear memory acquisition and consolidation in mice. Each mouse was conditioned, and 2 h later started on treatments. One-way ANOVA analysis revealed a significant effect of treatments on fear retention (F (4,22)=4.964, p=0.005). A multiple comparison post hoc Tukey's analysis revealed that compared to non-stressed (NS) mice, mice treated with intranasal cotinine (p<0.05) and cotinine plus krill oil (p<0.01) showed a significant decrease in the fear reaction in the retention test. On the contrary, no significant effects of krill oil alone or oral sertraline were observed (FIG. 24A).

Cotinine and Cotinine Plus Krill Oil Enhanced Contextual Fear Extinction

Figure 24B:
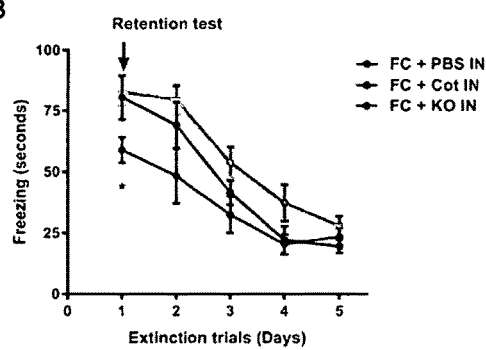
Figure 24:
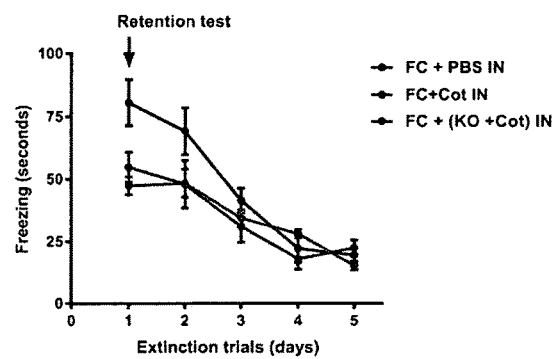
Figure 24D:
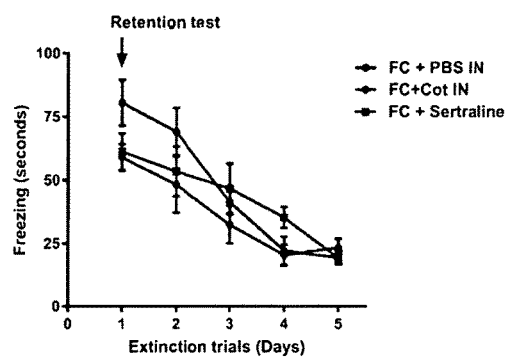

The effect of cotinine and krill oil on the extinction of contextual fear memory was assessed by measuring freezing behavior during the daily extinction trials, all groups of mice showed a decrease in freezing that reached a steady decrease by day 5. However, a repeated measure ANOVA throughout the 5 days of extinction revealed a significant difference induced by treatments (F (1.762, 7.046)=6.001, p=0.0324) and days (F (4, 16)=42.19, p<0.0001) on the freezing behavior. Cotinine- and cotinine plus krill oil-treated mice showed a faster extinction of fear, but they reached a maximal decrease at the same time than mice treated with PBS, on day 4 (FIG. 24C). Separately, mice treated with sertraline or krill oil alone showed an overall slower extinction of fear than controls, reaching a decrease that was comparable to control PBS-treated mice only on day 5 (FIGS. 24B and 24D).

Figure 25:
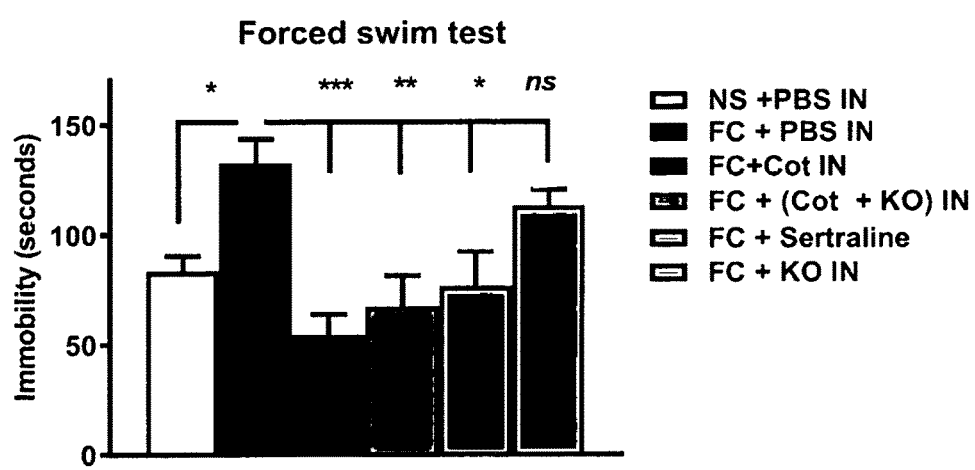
FIG. 25. Effect of cotinine and krill oil on depressive-like behavior in the forced swim tests. Two hours after fear conditioning (FC) mice (n=5-8 mice/group) received oral sertraline (2 mg/day), intranasal (IN) krill oil (KO), IN Cotinine (Cot) (24 μl, 10 mg/ml), or IN Cot plus KO and subjected to fear extinction. The graphs depict the effect of treatments on freezing behavior a measure of depressive-like behavior. Data was analyzed using one-way ANOVA. ns, non-significant change; *, $p<0.05$; , $p<0.01$; *, $p<0.001$.
Figure 27:
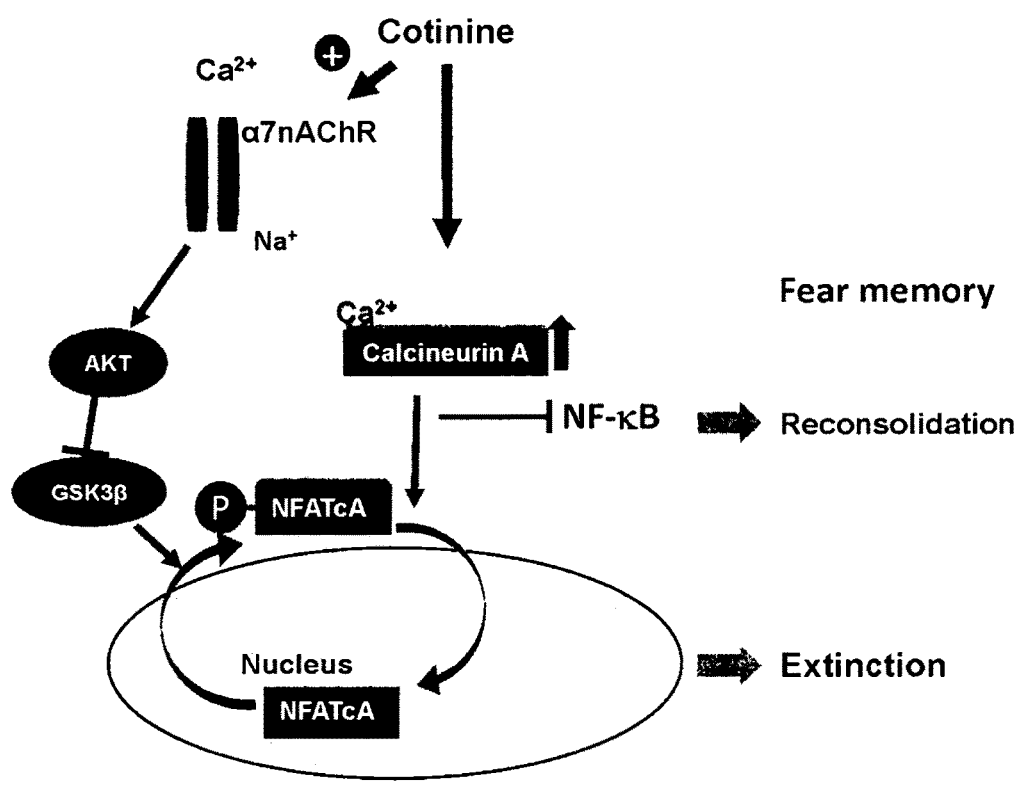
FIG. 27. Potential effects of cotinine on calcineurin A activity during extinction. The diagram despict the activation of Cotinine enhancing the activation of the α7nAChR and the consequent activation of Akt and calcineurin and the inactivation of GSK3β and NFκB. Calpain may by dephosphorylation of NFAT and inhibition of GSK3β will stimulate the expression of genes involved in extinction and will inhibit transcription factors involved in consolidation of fear memory such as NFκB.

Effect of Cotinine, Sertraline and Krill Oil on Depressive-Like Behavior in Conditioned Mice The data revealed that the conditioned mice subjected to fear extinction presented a significant decrease. The analysis of depressive-like behavior data in the forced swim test revealed a significant difference between treatment groups (One-way ANOVA, F (5,38)=6.32, p=0.0002). Mice subjected to FC with a single shock showed higher levels of depressive-like behavior than NS mice treated with PBS (p<0.01). FC mice post-treated with intranasal cotinine and sertraline showed a significant decrease in depressive-like behavior (p<0.05) expressed as a higher immobility times in the forced swim test. A Tukey's post hoc analysis showed that intranasal cotinine (p<0.001), the combination of cotinine plus krill oil (p<0.005), and sertraline (p<0.05) significantly decreased depressive-like behavior expressed as a decrease of immobility values in the forced swim test (FIG. 25). Krill oil showed an antidepressant effect, but this did not show significance.

Effect of Cotinine on Calcineurin a in the Hippocampus of Conditioned Mice

Previous studies showed that calcineurin A is involved in the neuronal changes associated with fear extinction [40,98, 99] and that antidepressants increase its expression [100]. Thus, based on the anti-depressant activity of cotinine, the effect of intranasal cotinine on the hippocampal expression of calcineurin A in NS and conditioned mice was investigated. The conditioned mice showed a significant decrease in the levels of calcineurin A (Student's t-test, t=2.597 df=7, p=0.036) when compared to NS mice in the hippocampus (60% decrease) (FIG. 26A). However, significant changes in the expression of calcineurin A between treatment groups were found (One-way ANOVA, F (2,13)=6, 26, p=0.013). Mice post-treated with intranasal cotinine showed calcineurin A levels in the hippocampus significantly different from PBS-treated conditioned mice (p<0.001) (FIG. 26B). No significant differences were observed between PBS-treated conditioned mice and krill oil or krill oil plus cotinine-treated mice (p>0.05).

Discussion

An optimal drug to prevent or treat PTSD may target the main aspects of the disease in a rapid, inexpensive, and targeted manner. Current evidence showed beneficial effects of cotinine on working memory, anxiety, depression, and the extinction of fear in mouse models of PTSD [14,101,18,102]. In here, it was investigated the effect of intranasal cotinine alone or combined with krill oil on depressive behavior and the consolidation and extinction of contextual fear memory in mice. Intranasal cotinine preparations when administered 2 h after conditioning efficiently reduced the consolidation or retrieval of contextual fear memory, enhanced the extinction of the fear responses and diminished depressive-like behavior in mice. The mix cotinine plus krill oil, was superior to cotinine alone in preventing the consolidation of fear memory and in diminishing depressive/like behavior after fear conditioning. Intranasal krill oil alone delayed the extinction of the fear memory. When the effect of conditioning and extinction on calcineurin A expression was determined, it was found that after extinction there was a reduced expression of calcineurin A in the hippocampus of conditioned mice treated with PBS, while cotinine increased its levels.

No previous studies have investigated the effect of intranasal cotinine preparations on the extinction of contextual memory. The fact that cotinine was effective by intranasal delivery, using a technique probed to deliver drugs to the brain mainly (about >90%), suggests that cotinine and not a liver-derived metabolite of this alkaloid is responsible for its beneficial effects. On the other hand, IN delivery probed to be effective at doses of cotinine ten times lower than previously reported doses enhancing fear extinction [18].

Overall, cotinine preparations were superior to sertraline in diminishing fear responses, while having similar effect diminishing the consolidation of fear memory and the ensuing depressive-like behavior in mice. In rodents, sertraline is [103] more effective in females than its male counterparts [104]. Only a few studies have investigated the effects of antidepressants on the extinction of aversive memories, and the conclusions derived from them are no very consistent [105,106]. It has been reported that in male rodents, sertraline did not diminish anxiety. Furthermore, during extinction, sertraline increased the time spent defensive that declined during the consecutive sessions [104]. The present study shows that cotinine plus krill oil is effective in decreasing fear memory consolidation and diminishing depressive-like behavior. To our actual knowledge, the only probed targets of cotinine are the nAChRs, which stimulation or stabilization is thought to enhance synaptic plasticity, to decrease neuronal and astrocytes damage and to reduce neuroinflammation [107,27]. Interestingly, krill oil contains phosphatidylcholine, that may be used to synthesize acetylcholine, as a ligand to bind nAChRs [74]. This effect may further potentiate the beneficial effects of cotinine stabilizing the receptor in the plasma membrane and positively modulating its function.

Previous studies showed evidence suggesting that krill oil improves cognitive abilities, decreases depressive-like behavior, and reduces inflammation in rodents [76,68,71]. One of these studies found increased brain cell generation in the dentate gyrus of the hippocampal formation, and a decrease of reactive oxygen species in the cerebral cortex and hippocampus of krill oil-treated rats [68]. Furthermore, rats subjected to forced swim stress, and treated with krill oil or imipramine showed reduced immobility times in the forced swim test and an improvement in memory functions than control animals [68]. This evidence suggests an improvement in cognitive abilities and mood induced by krill oil supported by a decrease in oxidative stress. Recent studies have shown that components of the krill oil, n-3 long-chain polyunsaturated fatty acid (PUFA) and n-6 PUFA (3:6) ratio influences fear memory. They examined several dietary 3:6 ratios on fear memory in mice subjected to contextual fear conditioning and showed that fear memory expression correlated negatively with dietary, serum, and brain 3:6 ratios in mice. A pharmacodynamic analysis in mice fed a high 3:6 ratio diet revealed that the PUFA acted through the CB1 receptor (CB1R) and increased short-term synaptic plasticity in the pyramidal neurons of the BLA. The authors suggest that the ratio n-3 to n-6 PUFA regulates fear memory via cannabinoid CB1 receptors (Yamada, 2014). PUFA seems to control the levels of endogenous agonist of CB receptors (Watkins, 2010). In the present study, a positive effect of krill oil alone in diminishing fear memory consolidation or enhancing its extinction was not found. On the contrary, a delay in the extinction of contextual fear memory response was observed. The different outcome may be related to the length of the administration and the sex of the subjects. In this study, mice were treated short-time after the conditioning to investigate the potential of intranasal krill oil as a standalone treatment or adjuvant treatment for cotinine in preventing the consolidation of fear memory and its extinction. The superior effect of cotinine in combination with krill oil attained in mice, it is encouraging and suggests a similar enhancement of the beneficial effects also in humans. The synergic effect of cotinine plus krill oil, in the absence of an effect of krill oil alone, suggests that the potentiation of cotinine effects by krill oil may be responsible for the improved effect of the mix.

Calcineurin has been implicated in the consolidation and stability of newly acquired memories [108]. Previous reports stated psychological stress inhibits the expression of calcineurin A, and that it can be later restored by antidepressants [100]. This evidence agrees with our results showing that fear conditioning decreased the expression of calcineurin A in the hippocampus and that the antidepressant effect of intranasal calcineurin treatment corrected this decrease. Also, it has been shown that the over-expression of calcineurin in the forebrain decreased the rate of learning in fear conditioning tasks [46,45]. Coincidentally, we found that cotinine preparations that increased calcineurin A expression inhibited the consolidation of contextual fear memory. Furthermore, it has been defined an essential role of calcineurin in memory extinction or behaviors requiring behavioral inhibition [108]. The authors suggested that calcineurin is involved in behavioral flexibility [108].

Overall, the results suggest that short-term treatment with intranasal cotinine plus krill oil is superior to sertraline and krill oil alone in enhancing fear extinction. Despite krill oil plus cotinine is only slightly superior to cotinine alone in decreasing fear responses, the use of the mix with krill oil has the added advantage that krill oil has beneficial effects over the vascular health.

Thus, cotinine plus krill oil delivered intranasally, represents a right combination for the treatment of people with PTSD that have a higher incidence of vascular diseases. Further clinical studies would be required to fully confirm the therapeutic value of intranasal cotinine alone and combined with krill oil for facilitating the recovery of people with PTSD. The evidence shows that cotinine intranasal alone or in combination with krill oil facilitate the extinction of contextual fear memory and diminish depressive behavior at a dose ten times lower that the previously active oral dose of cotinine in mice. The pro-cholinergic, anti-oxidant and anti-inflammatory effects of both compounds may explain their synergic positive effects on depression. The effect of cotinine on calcineurin A seems to be another critical mechanism of action of cotinine against PTSD pathology.

References for Example 4

1. Garfinkel S N, Abelson J L, King A P, Sripada R K, Wang X, Gaines L M, Liberzon I (2014) Impaired contextual modulation of memories in PTSD: an fMRI and psychophysiological study of extinction retention and fear renewal. J Neurosci 34 (40):13435-13443. doi:10.1523/JNEUROSCI.4287-13.2014.
2. Maren S, Phan K L, Liberzon I (2013) The contextual brain: implications for fear conditioning, extinction and psychopathology. Nat Rev Neurosci 14 (6):417-428. doi:10.1038/nrn3492
3. Rauch S L, Whalen P J, Shin L M, McInerney S C, Macklin M L, Lasko N B, On S P, Pitman R K (2000) Exaggerated amygdala response to masked facial stimuli in posttraumatic stress disorder: a functional MRI study. Biol Psychiatry 47 (9):769-776.
4. Liberzon I, Martis B (2006) Neuroimaging studies of emotional responses in PTSD. Ann N Y Acad Sci 1071:87-109. doi:10.1196/annals.1364.009.
5. De Bellis M D, Keshavan M S, Shifflett H, Iyengar S, Beers S R, Hall J, Moritz G (2002) Brain structures in pediatric maltreatment-related posttraumatic stress disorder: a sociodemographically matched study. Biol Psychiatry 52 (11):1066-1078.
6. Koenen K C, Sumner J A, Gilsanz P, Glymour M M, Ratanatharathorn A, Rimm E B, Roberts A L, Winning A, Kubzansky L D (2017) Post-traumatic stress disorder and cardiometabolic disease: improving causal inference to inform practice. Psychol Med 47 (2):209-225. doi:10.1017/S0033291716002294.
7. Cordova M J, Riba M B, Spiegel D (2017) Post-traumatic stress disorder and cancer. Lancet Psychiatry. doi:10.1016/S2215-0366(17)30014-7.
8. Arnson Y, Amital D, Fostick L, Silberman A, Polliack M L, Zohar J, Rubinow A, Amital H (2007) Physical activity protects male patients with post-traumatic stress disorder from developing severe fibromyalgia. Clin Exp Rheumatol 25 (4):529-533.
9. Brown A D, Barton D A, Lambert G W (2009) Cardiovascular abnormalities in patients with major depressive disorder: autonomic mechanisms and implications for treatment. CNS Drugs 23 (7):583-602.
10. Stein D J, Ipser J C, Seedat S (2006) Pharmacotherapy for post traumatic stress disorder (PTSD). Cochrane Database Syst Rev (1):CD002795. doi:10.1002/14651858.CD002795.pub2
11. Philip N S, Carpenter L L, Tyrka A R, Price L H (2010) Pharmacologic approaches to treatment resistant depression: a re-examination for the modern era. Expert Opin Pharmacother 11 (5):709-722.
12. Ahearn E P, Juergens T, Cordes T, Becker T, Krahn D (2011) A review of atypical antipsychotic medications for posttraumatic stress disorder. Int Clin Psychopharmacol 26 (4):193-200. doi:10.1097/YIC.0b013e3283473738.
13. Mahan A L, Ressler K J (2012) Fear conditioning, synaptic plasticity and the amygdala: implications for posttraumatic stress disorder. Trends Neurosci 35 (1):24-35. doi:10.1016/j.tins.2011.06.007.
14. Barreto G E, Yarkov A, Avila-Rodriguez M, Aliev G, Echeverria V (2015) Nicotine-Derived Compounds as Therapeutic Tools Against Post-Traumatic Stress Disorder. Curr Pharm Des 21 (25):3589-3595.
15. Echeverria V, Grizzell J A, Barreto G E (2016) Neuroinflammation: A Therapeutic Target of Cotinine for the Treatment of Psychiatric Disorders? Curr Pharm Des 22 (10):1324-1333
16. Mendoza C, Barreto G E, Avila-Rodriguez M, Echeverria V (2016) Role of neuroinflammation and sex hormones in war-related PTSD. Mol Cell Endocrinol 434:266-277. doi:10.1016/j.mce.2016.05.016.
17. Perez-Urrutia N, Mendoza C, Alvarez-Ricartes N, Oliveros-Matus P, Echeverria F, Grizzell J A, Barreto G E, Iarkov A, Echeverria V (2017) Intranasal cotinine improves memory, and reduces depressive-like behavior, and GFAP+ cells loss induced by restraint stress in mice. Exp Neurol 295:211-221. doi:10.1016/j.expneurol.2017.06.016.
18. Zeitlin R, Patel S, Solomon R, Tran J, Weeber E J, Echeverria V (2012) Cotinine enhances the extinction of contextual fear memory and reduces anxiety after fear conditioning. Behav Brain Res 228 (2):284-293. doi:10.1016/j.bbr.2011.11.023.
19. Benowitz N L, Sharp D S (1989) Inverse relation between serum cotinine concentration and blood pressure in cigarette smokers. Circulation 80 (5):1309-1312.
20. Bowman E R, Mc K H, Jr. (1962) Studies on the metabolism of (−)-cotinine in the human. J Pharmacol Exp Ther 135:306-311.
21. Hatsukami D, Anton D, Keenan R, Callies A (1992) Smokeless tobacco abstinence effects and nicotine gum dose. Psychopharmacology (Berl) 106 (1):60-66.
22. Hatsukami D, Lexau B, Nelson D, Pentel P R, Sofuoglu M, Goldman A (1998) Effects of cotinine on cigarette self-administration. Psychopharmacology (Berl) 138 (2):184-189.
23. Hatsukami D, Pentel P R, Jensen J, Nelson D, Allen S S, Goldman A, Rafael D (1998) Cotinine: effects with and without nicotine. Psychopharmacology (Berl) 135 (2):141-150.
24. Hatsukami D K, Grillo M, Pentel P R, Oncken C, Bliss R (1997) Safety of cotinine in humans: physiologic, subjective, and cognitive effects. Pharmacol Biochem Behav 57 (4):643-650.
25. Rehani K, Scott D A, Renaud D, Hamza H, Williams L R, Wang H, Martin M (2008) Cotinine-induced convergence of the cholinergic and PI3 kinase-dependent anti-inflammatory pathways in innate immune cells. Biochim Biophys Acta 1783 (3):375-382.
26. Echeverria V, Yarkov A, Aliev G (2016) Positive modulators of the alpha7 nicotinic receptor against neuroinflammation and cognitive impairment in Alzheimer's disease. Prog Neurobiol 144:142-157. doi:10.1016/j.pneurobio.2016.01.002.
27. Terry A V, Jr., Callahan P M, Bertrand D (2015) R-(+) and S-(−) isomers of cotinine augment cholinergic responses in vitro and in vivo. J Pharmacol Exp Ther 352 (2):405-418. doi:10.1124/jpet.114.219881.
28. Grizzell J A, Iarkov A, Holmes R, Mori T, Echeverria V (2014) Cotinine reduces depressive-like behavior, working memory deficits, and synaptic loss associated with chronic stress in mice. Behav Brain Res 268:55-65. doi:10.1016/j.bbr.2014.03.047.
29. Femenia T, Gomez-Galan M, Lindskog M, Magara S (2012) Dysfunctional hippocampal activity affects emotion and cognition in mood disorders. Brain Res 1476:58-70. doi:10.1016/j.brainres.2012.03.053.
30. Fernandes B S, Gama C S, Cereser K M, Yatham L N, Fries G R, Colpo G, de Lucena D, Kunz M, Gomes F A, Kapczinski F (2011) Brain-derived neurotrophic factor as a state-marker of mood episodes in bipolar disorders: a systematic review and meta-regression analysis. J Psychiatr Res 45 (8):995-1004. doi:10.1016/j.jpsychires.2011.03.002.
31. Jun H, Mohammed Qasim Hussaini S, Rigby M J, Jang M H (2012) Functional role of adult hippocampal neurogenesis as a therapeutic strategy for mental disorders. Neural Plast 2012:854285. doi:10.1155/2012/854285.
32. Sairanen M, O'Leary O F, Knuuttila J E, Castren E (2007) Chronic antidepressant treatment selectively increases expression of plasticity-related proteins in the hippocampus and medial prefrontal cortex of the rat. Neuroscience 144 (1):368-374. doi:10.1016/j.neuroscience.2006.08.069.
33. Gu Z, Lamb P W, Yakel J L (2012) Cholinergic coordination of presynaptic and postsynaptic activity induces timing-dependent hippocampal synaptic plasticity. J Neurosci 32 (36):12337-12348.
34. Echeverria V, Zeitlin R, Burgess S, Patel S, Barman A, Thakur G, Mamcarz M, Wang L, Sattelle D B, Kirschner D A, Mori T, Leblanc R M, Prabhakar R, Arendash G W (2011) Cotinine reduces amyloid-beta aggregation and improves memory in Alzheimer's disease mice. J Alzheimers Dis 24 (4):817-835. doi:10.3233/JAD-2011-102136.
35. Grizzell J A, Patel S, Barreto G E, Echeverria V (2017) Cotinine improves visual recognition memory and decreases cortical Tau phosphorylation in the Tg6799 mice. Prog Neuropsychopharmacol Biol Psychiatry 78:75-81. doi:10.1016/j.pnpbp.2017.05.010.
36. Patel S, Grizzell J A, Holmes R, Zeitlin R, Solomon R, Sutton T L, Rohani A, Charry L C, Iarkov A, Mori T, Echeverria Moran V (2014) Cotinine halts the advance of Alzheimer's disease-like pathology and associated depressive-like behavior in Tg6799 mice. Front Aging Neurosci 6:162. doi:10.3389/fnagi.2014.00162.
37. Eisenberg M, Dudai Y (2004) Reconsolidation of fresh, remote, and extinguished fear memory in Medaka: old fears don't die. Eur J Neurosci 20 (12):3397-3403. doi:10.1111/j.1460-9568.2004.03818.x.
38. Cannich A, Wotjak C T, Kamprath K, Hermann H, Lutz B, Marsicano G (2004) CB1 cannabinoid receptors modulate kinase and phosphatase activity during extinction of conditioned fear in mice. Learn Mem 11 (5):625-632.
39. Hall J, Thomas K L, Everitt B J (2001) Fear memory retrieval induces CREB phosphorylation and Fos expression within the amygdala. Eur J Neurosci 13 (7):1453-1458.
40. de la Fuente V, Freudenthal R, Romano A (2012) Reconsolidation or extinction: transcription factor switch in the determination of memory course after retrieval. J Neurosci 31 (15):5562-5573.
41. de la Fuente V, Freudenthal R, Romano A (2011) Reconsolidation or extinction: transcription factor switch in the determination of memory course after retrieval. J Neurosci 31 (15):5562-5573. doi:10.1523/JNEUROSCI.6066-10.2011.
42. de la Fuente V, Federman N, Fustñana M S, Zalcman G, Romano A (2014) Calcineurin phosphatase as a negative regulator of fear memory in hippocampus: control on nuclear factor-κB signaling in consolidation and reconsolidation. Hippocampus 24 (12):1549-1561. doi:10.1002/hipo.22334.
43. Bozon B, Davis S, Laroche S (2003) A requirement for the immediate early gene zif268 in reconsolidation of recognition memory after retrieval. Neuron 40 (4):695-701. doi:S0896627303006743 [pii].
44. Bozon B, Kelly A, Josselyn S A, Silva A J, Davis S, Laroche S (2003) MAPK, CREB and zif268 are all required for the consolidation of recognition memory. Philos Trans R Soc Lond B Biol Sci 358 (1432):805-814.
45. Sachser R M, Santana F, Crestani A P, Lunardi P, Pedraza L K, Quillfeldt J A, Hardt O, Alvares Lde O (2016) Forgetting of long-term memory requires activation of NMDA receptors, L-type voltage-dependent Ca2+ channels, and calcineurin. Sci Rep 6:22771. doi:10.1038/srep22771.
46. Mansuy I M (2003) Calcineurin in memory and bidirectional plasticity. Biochem Biophys Res Commun 311 (4):1195-1208.
47. Lin C H, Lee C C, Gean P W (2003) Involvement of a calcineurin cascade in amygdala depotentiation and quenching of fear memory. Mol Pharmacol 63 (1):44-52.
48. Wang J, Liu S, Haditsch U, Tu W, Cochrane K, Ahmadian G, Tran L, Paw J, Wang Y, Mansuy I, Salter M M, Lu Y M (2003) Interaction of calcineurin and type-A GABA receptor gamma 2 subunits produces long-term depression at CA1 inhibitory synapses. J Neurosci 23 (3):826-836.
49. Polli J W, Billingsley M L, Kincaid R L (1991) Expression of the calmodulin-dependent protein phosphatase, calcineurin, in rat brain: developmental patterns and the role of nigrostriatal innervation. Brain Res Dev Brain Res 63 (1-2):105-119.
50. Kirtley A, Thomas K L (2010) The exclusive induction of extinction is gated by BDNF. Learn Mem 17 (12):612-619. doi:10.1101/lm.1877010.
51. Graef I A, Wang F, Charron F, Chen L, Neilson J, Tessier-Lavigne M, Crabtree G R (2003) Neurotrophins and netrins require calcineurin/NFAT signaling to stimulate outgrowth of embryonic axons. Cell 113 (5):657-670.
52. Groth R D, Mermelstein P G (2003) Brain-derived neurotrophic factor activation of NFAT (nuclear factor of activated T-cells)-dependent transcription: a role for the transcription factor NFATc4 in neurotrophin-mediated gene expression. J Neurosci 23 (22):8125-8134.
53. Sen B, Styner M, Xie Z, Case N, Rubin C T, Rubin J (2009) Mechanical loading regulates NFATc1 and beta-catenin signaling through a GSK3beta control node. J Biol Chem 284 (50):34607-34617. doi:10.1074/jbc.M109.039453.
54. Kim M S, Shutov L P, Gnanasekaran A, Lin Z, Rysted J E, Ulrich J D, Usachev Y M (2014) Nerve growth factor (NGF) regulates activity of nuclear factor of activated T-cells (NFAT) in neurons via the phosphatidylinositol 3-kinase (PI3K)-Akt-glycogen synthase kinase 313 (GSK3(3)) pathway. J Biol Chem 289 (45):31349-31360. doi:10.1074/jbc.M114.587188.
55. Foster T C, Sharrow K M, Masse J R, Norris C M, Kumar A (2001) Calcineurin links Ca2+ dysregulation with brain aging. J Neurosci 21 (11):4066-4073.
56. Zhu W L, Shi H S, Wang S J, Wu P, Ding Z B, Lu L (2011) Hippocampal CA3 calcineurin activity participates in depressive-like behavior in rats. J Neurochem 117 (6):1075-1086.
57. Ahi J, Radulovic J, Spiess J (2004) The role of hippocampal signaling cascades in consolidation of fear memory. Behav Brain Res 149 (1):17-31.
58. Silva A J, Kogan J H, Frankland P W, Kida S (1998) CREB and memory. Annu Rev Neurosci 21:127-148.
59. Gundersen B B, Briand L A, Onksen J L, Lelay J, Kaestner K H, Blendy J A (2013) Increased Hippocampal Neurogenesis and Accelerated Response to Antidepressants in Mice with Specific Deletion of CREB in the Hippocampus: Role of cAMP Response-Element Modulator tau. J Neurosci 33 (34):13673-13685. doi:10.1523/JNEUROSCI.1669-13.2013.
60. Kingsbury T J, Bambrick L L, Roby C D, Krueger B K (2007) Calcineurin activity is required for depolarization-induced, CREB-dependent gene transcription in cortical neurons. J Neurochem 103 (2):761-770. doi:10.1111/j.1471-4159.2007.04801.x.
61. Seo J S, Lee K W, Kim T K, Baek I S, Im J Y, Han P L (2011) Behavioral stress causes mitochondrial dysfunction via ABAD up-regulation and aggravates plaque pathology in the brain of a mouse model of Alzheimer disease. Free Radic Biol Med 50 (11):1526-1535.
62. Rammal H, Bouayed J, Younos C, Soulimani R (2008) Evidence that oxidative stress is linked to anxiety-related behaviour in mice. Brain Behav Immun 22 (8):1156-1159.
63. Hensley K, Mhatre M, Mou S, Pye Q N, Stewart C, West M, Williamson K S (2006) On the relation of oxidative stress to neuroinflammation: lessons learned from the G93A-SOD1 mouse model of amyotrophic lateral sclerosis. Antioxid Redox Signal 8 (11-12):2075-2087.
64. Bewernick B H, Schlaepfer T E (2013) Chronic depression as a model disease for cerebral aging. Dialogues Clin Neurosci 15 (1):77-85.
65. Ong W Y, Farooqui T, Kokotos G, Farooqui A A (2015) Synthetic and Natural Inhibitors of Phospholipases A2: Their Importance for Understanding and Treatment of Neurological Disorders. ACS Chem Neurosci.
66. Hovatta I, Juhila J, Donner J (2010) Oxidative stress in anxiety and comorbid disorders. Neurosci Res 68 (4):261-275. doi:10.1016/j.neures.2010.08.007.
67. Chaturvedi R K, Beal M F (2008) Mitochondrial approaches for neuroprotection. Ann N Y Acad Sci 1147: 395-412. doi:10.1196/annals.1427.027.
68. Wibrand K, Berge K, Messaoudi M, Duffaud A, Panja D, Bramham C R, Burri L (2013) Enhanced cognitive function and antidepressant-like effects after krill oil supplementation in rats. Lipids Health Dis 12:6. doi:10.1186/1476-511X-12-6.
69. Barros M P, Poppe S C, Bondan E F (2014) Neuroprotective properties of the marine carotenoid astaxanthin and omega-3 fatty acids, and perspectives for the natural combination of both in krill oil. Nutrients 6 (3):1293-1317. doi:10.3390/nu6031293.
70. Kidd P M (2007) Omega-3 DHA and EPA for cognition, behavior, and mood: clinical findings and structural-functional synergies with cell membrane phospholipids. Altern Med Rev 12 (3):207-227.
71. Burri L, Johnsen L (2015) Krill products: an overview of animal studies. Nutrients 7 (5):3300-3321. doi:10.3390/nu7053300.
72. Kwantes J M, Grundmann O (2015) A brief review of krill oil history, research, and the commercial market. J Diet Suppl 12 (1):23-35. doi:10.3109/19390211.2014.902000.
73. Bunea R, El Farrah K, Deutsch L (2004) Evaluation of the effects of Neptune Krill Oil on the clinical course of hyperlipidemia. Altern Med Rev 9 (4):420-428.
74. Winther B, Hoem N, Berge K, Reubsaet L (2011) Elucidation of phosphatidylcholine composition in krill oil extracted from Euphausia superba. Lipids 46 (1):25-36. doi:10.1007/s11745-010-3472-6.
75. Wijendran V, Huang M C, Diau G Y, Boehm G, Nathanielsz P W, Brenna J T (2002) Efficacy of dietary arachidonic acid provided as triglyceride or phospholipid as substrates for brain arachidonic acid accretion in baboon neonates. Pediatr Res 51 (3):265-272. doi:10.1203/00006450-200203000-00002.
76. Vigerust N F, Bjorndal B, Bohov P, Brattelid T, Svardal A, Berge R K (2013) Krill oil versus fish oil in modulation of inflammation and lipid metabolism in mice transgenic for TNF-alpha. Eur J Nutr 52 (4):1315-1325. doi:10.1007/s00394-012-0441-2.
77. Sublette M E, Ellis S P, Geant A L, Mann J J (2011) Meta-analysis of the effects of eicosapentaenoic acid (EPA) in clinical trials in depression. J Clin Psychiatry 72 (12):1577-1584. doi:10.4088/JCP.10m06634.
78. Alcala-Barraza S R, Lee M S, Hanson L R, McDonald A A, Frey W H, 2nd, McLoon L K (2010) Intranasal delivery of neurotrophic factors BDNF, CNTF, EPO, and NT-4 to the CNS. J Drug Target 18 (3):179-190.
79. Benedict C, Frey W H, 2nd, Schioth H B, Schultes B, Born J, Hallschmid M (2011) Intranasal insulin as a therapeutic option in the treatment of cognitive impairments. Exp Gerontol 46 (2-3):112-115. doi:10.1016/j.exger.2010.08.026.
80. Dhuria S V, Hanson L R, Frey W H, 2nd (2010) Intranasal delivery to the central nervous system: mechanisms and experimental considerations. J Pharm Sci 99 (4):1654-1673.
81. Chapman C D, Frey W H, 2nd, Craft S, Danielyan L, Hallschmid M, Schioth H B, Benedict C (2013) Intranasal treatment of central nervous system dysfunction in humans. Pharm Res 30 (10):2475-2484.
82. Ross T M, Zuckermann R N, Reinhard C, Frey W H, 2nd (2008) Intranasal administration delivers peptoids to the rat central nervous system. Neurosci Lett 439 (1):30-33.
83. Yang Y, Ma D, Wang Y, Jiang T, Hu S, Zhang M, Yu X, Gong C X (2013) Intranasal insulin ameliorates tau hyperphosphorylation in a rat model of type 2 diabetes. J Alzheimers Dis 33 (2):329-338. doi:10.3233/JAD-2012-121294.
84. Ott V, Benedict C, Schultes B, Born J, Hallschmid M (2012) Intranasal administration of insulin to the brain impacts cognitive function and peripheral metabolism. Diabetes Obes Metab 14 (3):214-221. doi:10.1111/j.1463-1326.2011.01490.x.
85. Meneses G, Gevorkian G, Florentino A, Bautista M A, Espinosa A, Acero G, Diaz G, Fleury A, Perez Osorio I N, Del Rey A, Fragoso G, Sciutto E, Besedovsky H (2017) Intranasal delivery of dexamethasone efficiently controls LPS-induced murine neuroinflammation. Clin Exp Immunol 190 (3):304-314. doi:10.1111/cei.13018.
86. Koch S B, van Zuiden M, Nawijn L, Frijling J L, Veltman D J, Olff M (2016) Intranasal Oxytocin Administration Dampens Amygdala Reactivity towards Emotional Faces in Male and Female PTSD Patients. Neuropsychopharmacology 41 (6):1495-1504. doi:10.1038/npp.2015.299.
87. Palgi S, Klein E, Shamay-Tsoory S G (2016) Oxytocin improves compassion toward women among patients with PTSD. Psychoneuroendocrinology 64:143-149. doi:10.1016/j.psyneuen.2015.11.008.
88. Costantino H R, Leonard A K, Brandt G, Johnson P H, Quay S C (2008) Intranasal administration of acetylcholinesterase inhibitors. BMC Neurosci 9 Suppl 3:S6.
89. Blecharz-Klin K, Piechal A, Joniec-Maciejak I, Pyrzanowska J, Widy-Tyszkiewicz E (2012) Effect of intranasal manganese administration on neurotransmission and spatial learning in rats. Toxicol Appl Pharmacol 265 (1):1-9. doi:10.1016/j.taap.2012.09.015.
90. Ruigrok M J, de Lange E C (2015) Emerging Insights for Translational Pharmacokinetic and Pharmacokinetic- Pharmacodynamic Studies: Towards Prediction of Nose-to-Brain Transport in Humans. Aaps J 17 (3):493-505.
91. Davidson J, Pearlstein T, Londborg P, Brady K T, Rothbaum B, Bell J, Maddock R, Hegel M T, Farfel G (2001) Efficacy of sertraline in preventing relapse of posttraumatic stress disorder: results of a 28-week double-blind, placebo-controlled study. Am J Psychiatry 158 (12):1974-1981.
92. Hien D A, Levin F R, Ruglass L M, Lopez-Castro T, Papini S, Hu M C, Cohen L R, Herron A (2015) Combining seeking safety with sertraline for PTSD and alcohol use disorders: A randomized controlled trial. J Consult Clin Psychol 83 (2):359-369. doi:10.1037/a0038719.
93. Buhmann C B, Nordentoft M, Ekstroem M, Carlsson J, Mortensen E L (2016) The effect of flexible cognitive-behavioural therapy and medical treatment, including antidepressants on post-traumatic stress disorder and depression in traumatised refugees: pragmatic randomised controlled clinical trial. Br J Psychiatry 208 (3):252-259. doi:10.1192/bjp.bp.114.150961.
94. Kamo T, Maeda M, Oe M, Kato H, Shigemura J, Kuribayashi K, Hoshino Y (2016) Dosage, effectiveness, and safety of sertraline treatment for posttraumatic stress disorder in a Japanese clinical setting: a retrospective study. BMC Psychiatry 16 (1):434. doi:10.1186/s12888-016-1138-5.
95. Hanson L R, Fine J M, Hoekman J D, Nguyen T M, Burns R B, Martinez P M, Pohl J, Frey W H, 2nd (2012) Intranasal delivery of growth differentiation factor 5 to the central nervous system. Drug Deliv 19 (3):149-154.
96. Castagne V, Moser P, Roux S, Porsolt R D (2011) Rodent models of depression: forced swim and tail suspension behavioral despair tests in rats and mice. Curr. Protoc Neurosci Chapter 8:Unit 8 10A.
97. Dunn A J, Swiergiel A H (2008) Effects of acute and chronic stressors and CRF in rat and mouse tests for depression. Ann N Y Acad Sci 1148:118-126. doi: 10.1196/annals.1410.022.
98. Lin C H, Yeh S H, Leu T H, Chang W C, Wang S T, Gean P W (2003) Identification of calcineurin as a key signal in the extinction of fear memory. J Neurosci 23 (5):1574-1579.
99. Lin C H, Yeh S H, Lu H Y, Gean P W (2003) The similarities and diversities of signal pathways leading to consolidation of conditioning and consolidation of extinction of fear memory. J Neurosci 23 (23):8310-8317.
100. Crozatier C, Farley S, Mansuy I M, Dumas S, Giros B, Tzavara E T (2007) Calcineurin (protein phosphatase 2B) is involved in the mechanisms of action of antidepressants. Neuroscience 144 (4):1470-1476.
101. de Aguiar R B, Parfitt G M, Jaboinski J, Barros D M (2013) Neuroactive effects of cotinine on the hippocampus: behavioral and biochemical parameters. Neuropharmacology 71:292-298.
102. Moran V E (2012) Cotinine: Beyond that Expected, More than a Biomarker of Tobacco Consumption. Front Pharmacol 3:173.
103. Koek R J, Schwartz H N, Scully S, Langevin J P, Spangler S, Korotinsky A, Jou K, Leuchter A (2016) Treatment-refractory posttraumatic stress disorder (TRPTSD): a review and framework for the future. Prog Neuropsychopharmacol Biol Psychiatry 70:170-218. doi: 10.1016/j.pnpbp.2016.01.015.
104. Pereira-Figueiredo I, Castellano O, Riolobos A S, Ferreira-Dias G, Lopez D E, Sancho C (2017) Long-Term Sertraline Intake Reverses the Behavioral Changes Induced by Prenatal Stress in Rats in a Sex-Dependent Way. Front Behav Neurosci 11:99. doi:10.3389/fnbeh.2017.00099.
105. Burghardt N S, Bauer E P (2013) Acute and chronic effects of selective serotonin reuptake inhibitor treatment on fear conditioning: implications for underlying fear circuits. Neuroscience 247:253-272. doi:10.1016/j.neuroscience.2013.05.050.
106. Yang C H, Shi H S, Zhu W L, Wu P, Sun L L, Si J J, Liu M M, Zhang Y, Suo L, Yang J L (2012) Venlafaxine facilitates between-session extinction and prevents reinstatement of auditory-cue conditioned fear. Behav Brain Res 230 (1):268-273.
107. Echeverria V, Alex Grizzell J, Barreto G E (2016) Neuroinflammation: A Therapeutic Target of Cotinine for the Treatment of Psychiatric Disorders? Curr Pharm Des 22 (10):1324-1333.
108. Shaw J A, Matlovich N, Rushlow W, Cain P, Rajakumar N (2012) Role of calcineurin in inhibiting disadvantageous associations. Neuroscience 203:144-152.

What is claimed is:

1. A method for treating a disorder induced by chronic stress in a subject, the method comprising administering to the subject a therapeutically effective amount of cotinine, or a pharmaceutically acceptable salt thereof, and krill oil, thereby treating the disorder in the subject, wherein the disorder is depression or anxiety.

2. The method of claim 1, wherein the disorder is depression.

3. The method of claim 1, wherein the subject was diagnosed as having post-traumatic stress disorder (PTSD) prior to the administering step.

4. The method of claim 1, wherein the krill oil comprises omega-3 fatty acid, phospholipid, and/or astaxanthin.

5. The method of claim 4, wherein the omega-3 fatty acid is or comprises an omega-3 polyunsaturated fatty acid (PUFA).

6. The method of claim 5, wherein the omega-3 polyunsaturated fatty acid (PUFA) is selected from the group consisting of eicosapentanoic acid (EPA), docosahexaenoic acid (DHA) and combination thereof.

7. The method of claim 1, wherein the depression is selected from the group consisting of long-lasting depression, major depressive disorder (MDD), and stress-induced treatment resistant depression.

8. The method of claim 1, wherein the krill oil and the cotinine are administered simultaneously.

9. The method of claim 1, wherein the krill oil and the cotinine are not administered simultaneously.

10. The method of claim 1, wherein administering the cotinine and the krill oil additionally treats contextual fear memory dysfunction.

11. The method of claim 1, wherein the cotinine and the krill oil are co-formulated.

12. The method of claim 1, wherein the cotinine and the krill oil are not co-formulated.

13. The method of claim 1, wherein administering is via intranasal administration.

14. The method of claim 1, wherein cotinine is administered at a dosage of from about 100 mg/day to about 200 mg/day.

15. The method of claim 1, wherein the disorder is anxiety.

16. A method for treating a disorder induced by chronic stress in a subject, the method comprising intranasally administering to the subject a composition comprising a therapeutically effective amount of cotinine, or a pharmaceutically acceptable salt thereof, and krill oil, thereby treating the disorder in the subject, wherein the disorder is depression or anxiety.

17. The method of claim 16, wherein cotinine is administered at a dosage of from about 100 mg/day to about 200 mg/day.

18. A method for treating a disorder induced by chronic stress in a subject, the method comprising administering to the subject a therapeutically effective amount of exactly two active agents, wherein the two active agents are krill oil and cotinine, or a pharmaceutically acceptable salt thereof, and wherein the disorder is depression or anxiety.

19. The method of claim 18, wherein the krill oil and the cotinine are co-formulated.

20. The method of claim 18, wherein administering is via intranasal administration.

* * * * *